(12) United States Patent
Le Grand et al.

(10) Patent No.: US 7,288,537 B2
(45) Date of Patent: Oct. 30, 2007

(54) AZETIDINE DERIVATIVES AS CCR-3 RECEPTOR ANTAGONISTS

(75) Inventors: Darren Mark Le Grand, Horsham (GB); Clive McCarthy, Basel (CH); Clive Victor Walker, Horsham (GB); John James Woods, Horsham (GB)

(73) Assignee: Novartis AG, Basil (CH)

( * ) Notice: Subject to any disclaimer, the term of this patent is extended or adjusted under 35 U.S.C. 154(b) by 138 days.

(21) Appl. No.: 10/507,139

(22) PCT Filed: Mar. 14, 2003

(86) PCT No.: PCT/EP03/02715

§ 371 (c)(1),
(2), (4) Date: Sep. 9, 2004

(87) PCT Pub. No.: WO03/077907

PCT Pub. Date: Sep. 25, 2003

(65) Prior Publication Data

US 2005/0222118 A1 Oct. 6, 2005

(30) Foreign Application Priority Data

Mar. 15, 2002 (GB) .................. 0206218.0
Dec. 19, 2002 (GB) .................. 0229627.5

(51) Int. Cl.
*A61K 31/397* (2006.01)
*C07D 205/00* (2006.01)

(52) U.S. Cl. .................. 514/210.01; 548/952

(58) Field of Classification Search ................ 514/210; 548/952

See application file for complete search history.

(56) References Cited

U.S. PATENT DOCUMENTS 5,095,014 A * 3/1992 Taylor et al. .......... 514/210.17

FOREIGN PATENT DOCUMENTS

| EP | 0 903 349 | 3/1999 |
|---|---|---|
| GB | 2 093 456 | 9/1982 |
| WO | 99/04794 | 2/1999 |
| WO | 03/007939 | 1/2003 |

* cited by examiner

*Primary Examiner*—Joseph K. McKane
*Assistant Examiner*—Susannah Chung
(74) *Attorney, Agent, or Firm*—John B. Alexander

(57) ABSTRACT

Compounds of formula I

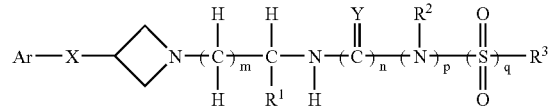

in free or salt form, wherein Ar, X, Y, $R^1$, $R^2$, $R^3$, $R^5$, m, n, p and q have the meanings as indicated in the specification, are useful for treating conditions mediated by CCR3. Pharmaceutical compositions that contain the compounds and processes for preparing the compounds are also described.

19 Claims, No Drawings

AZETIDINE DERIVATIVES AS CCR-3 RECEPTOR ANTAGONISTS

This invention relates to organic compounds, their preparation and their use as pharmaceuticals.

In one aspect the invention provides compounds of formula I

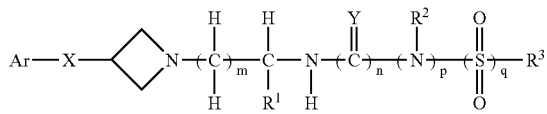

in free or salt form, where

Ar is phenyl optionally substituted by one or more substituents selected from halogen, $C_1$-$C_8$-alkyl, cyano or nitro;

$R^1$ is hydrogen or $C_1$-$C_8$-alkyl optionally substituted by hydroxy, $C_1$-$C_8$-alkoxy, acyloxy, halogen, carboxy, $C_1$-$C_8$-alkoxycarbonyl, —N($R^4$)$R^5$, —CON($R^6$)$R^7$ or by a monovalent cyclic organic group having 3 to 15 atoms in the ring system;

$R^2$ is hydrogen, $C_1$-$C_8$-alkyl or $C_3$-$C_{10}$-cycloalkyl and $R^3$ is $C_1$-$C_8$-alkyl substituted by phenyl, phenoxy, acyloxy or naphthyl, or $R^3$ is $C_3$-$C_{10}$-cycloalkyl optionally having a benzo group fused thereto, a heterocyclic group having 5 to 11 ring atoms of which 1 to 4 are hetero atoms, phenyl or naphthyl, said phenyl, phenoxy or naphthyl groups being optionally substituted by one or more substituents selected from halogen, cyano, hydroxy, acyl, nitro, —$SO_2NH_2$, $C_1$-$C_8$-alkyl optionally substituted by $C_1$-$C_8$-alkoxy, $C_1$-$C_8$-haloalkyl, $C_1$-$C_8$-alkoxy, $C_1$-$C_8$-haloalkoxy, $C_1$-$C_8$-alkylthio, —$SO_2$—$C_1$-$C_8$-alkyl, $C_1$-$C_8$-alkoxycarbonyl, $C_1$-$C_8$-acylamino optionally substituted on the nitrogen atom by $C_1$-$C_8$-alkyl, $C_1$-$C_8$-alkylamino, aminocarbonyl, $C_1$-$C_8$-alkylamino-carbonyl, di($C_1$-$C_8$-alkyl)amino, di($C_1$-$C_8$-alkyl)aminocarbonyl, di($C_1$-$C_8$-alkyl)aminocarbonyl-methoxy, or $R^2$ and $R^3$ together with the nitrogen atom to which they are attached denote a heterocyclic group having 5 to 10 ring atoms of which 1, 2 or 3 are hetero atoms;

$R^4$ and $R^5$ are each independently hydrogen or $C_1$-$C_8$-alkyl, or $R^4$ is hydrogen and $R^5$ is hydroxy-$C_1$-$C_8$-alkyl, acyl, —$SO_2R^8$ or —CON($R^6$)$R^7$, or $R^4$ and $R^5$ together with the nitrogen atom to which they are attached denote a 5-or 6-membered heterocyclic group;

$R^6$ and $R^7$ are each independently hydrogen or $C_1$-$C_8$-alkyl, or $R^6$ and $R^7$ together with the nitrogen atom to which they are attached denote a 5- or 6-membered heterocyclic group;

$R^8$ is $C_1$-$C_8$-alkyl, $C_1$-$C_8$-haloalkyl, or phenyl optionally substituted by $C_1$-$C_8$-alkyl;

X is —C(=O)—, —O—, —$CH_2$—, or CH(OH);

Y is oxygen or sulfur;

m is 1, 2, 3 or 4; and n, p and q are each 0 or 1, n+p+q=1 or 2, n+q=1, p+q=1, and when n is 0, p is 0.

Terms used in the specification have the following meanings:

"$C_1$-$C_8$-alkyl" as used herein denotes straight chain or branched $C_1$-$C_8$-alkyl, which may be, for example, methyl, ethyl, n-propyl, isopropyl, n-butyl, isobutyl, sec-butyl, tert-butyl, straight or branched pentyl, straight or branched hexyl, straight or branched heptyl, or straight or branched octyl. Preferably, $C_1$-$C_8$-alkyl is $C_1$-$C_4$-alkyl.

"$C_3$-$C_{10}$-cycloalkyl" as used herein may be, for example, cyclopropyl, cyclobutyl, cyclopentyl, methylcyclopentyl, cyclohexyl, methylcyclohexyl, dimethylcyclohexyl, cycloheptyl, bicycloheptyl, cyclooctyl, bicyclooctyl, bicyclononyl, tricyclononyl or tricyclodecyl.

"$C_1$-$C_8$-alkoxy" as used herein denotes straight chain or branched $C_1$-$C_8$-alkoxy which may be, for example, methoxy, ethoxy, n-propoxy, isopropoxy, n-butoxy, isobutoxy, sec-butoxy, tert-butoxy, straight or branched pentoxy, straight or branched hexyloxy, straight or branched heptyloxy, or straight or branched octyloxy. Preferably, $C_1$-$C_8$-alkoxy is $C_1$-$C_4$-alkoxy.

"$C_1$-$C_8$-haloalkyl" as used herein denotes $C_1$-$C_8$-alkyl as hereinbefore defined substituted by one or more halogen atoms, preferably one, two or three halogen atoms.

"$C_1$-$C_8$-haloalkoxy" as used herein denotes $C_1$-$C_8$-alkoxy as hereinbefore defined substituted by one or more halogen atoms, preferably one, two or three halogen atoms.

"Aminocarbonyl" as used herein denotes amino attached through the nitrogen atom to a carbonyl group.

"$C_1$-$C_8$-alkylamino" and "di($C_1$-$C_8$-alkyl)amino" as used herein denote amino substituted respectively by one or two $C_1$-$C_8$-alkyl groups as hereinbefore defined, which may be the same or different. Preferably $C_1$-$C_8$-alkylamino and di($C_1$-$C_8$-alkyl)amino are respectively $C_1$-$C_4$-alkylamino and di($C_1$-$C_4$-alkyl)amino.

"$C_1$-$C_8$-alkylaminocarbonyl" and "di($C_1$-$C_8$-alkyl)aminocarbonyl" as used herein denote aminocarbonyl as hereinbefore defined substituted respectively on the nitrogen atom by one or two $C_1$-$C_8$-alkyl groups as hereinbefore defined, which may be the same or different. Preferably $C_1$-$C_8$-alkylaminocarbonyl and di($C_1$-$C_8$-alkyl)aminocarbonyl are respectively $C_1$-$C_4$-alkylaminocarbonyl and di($C_1$-$C_4$-alkyl)aminocarbonyl.

"$C_1$-$C_8$-alkylthio" as used herein denotes $C_1$-$C_8$-alkyl as hereinbefore defined linked to —S—.

"Acyl" as used herein denotes alkylcarbonyl, for example $C_1$-$C_8$-alkylcarbonyl where $C_1$-$C_8$-alkyl may be one of the $C_1$-$C_8$-alkyl groups hereinbefore mentioned, optionally substituted by one or more halogen atoms; cycloalkylcarbonyl, for example $C_3$-$C_8$-cycloalkylcarbonyl where $C_3$-$C_8$-cycloalkyl may be, for example, cyclopropyl, cyclobutyl, cyclopentyl, cyclohexyl, cycloheptyl or cyclooctyl; 5- or 6-membered heterocyclylcarbonyl having one or two hetero atoms selected from nitrogen, oxygen and sulfur in the ring, such as furylcarbonyl or pyridylcarbonyl; arylcarbonyl, for example $C_6$-$C_{10}$-arylcarbonyl such as benzoyl; or aralkylcarbonyl, for example $C_6$ to $C_{10}$-aryl-$C_1$-$C_4$-alkylcarbonyl such as benzylcarbonyl or phenylethylcarbonyl. Preferably acyl is $C_1$-$C_4$-alkylcarbonyl.

"Acyloxy" as used herein denotes alkylcarbonyloxy, for example $C_1$-$C_8$-alkylcarbonyloxy where $C_1$-$C_8$-alkyl may be one of the $C_1$-$C_8$-alkyl groups hereinbefore mentioned, optionally substituted by one or more halogen atoms; cycloalkylcarbonyloxy, for example $C_3$-$C_8$-cycloalkylcarbonyloxy where $C_3$-$C_8$-cycloalkyl may be, for example, cyclopropyl, cyclobutyl, cyclopentyl, cyclohexyl, cycloheptyl or cyclooctyl; 5- or 6-membered heterocyclylcarbonyloxy having one or two hetero atoms selected from nitrogen, oxygen and sulfur in the ring, such as furylcarbonyloxy or pyridylcarbonyloxy; arylcarbonyloxy, for example $C_6$-$C_{10}$-arylcarbonyloxy such as benzoyloxy; or aralkylcarbonyloxy, for example $C_6$ to $C_{10}$-aryl-$C_1$-$C_4$-alkylcarbonyloxy such as benzylcarbonyloxy or phenylethylcarbonyloxy, or aryloxyalkylcarbonyloxy, for example, $C_6$-$C_{10}$-aryloxy-$C_1$-$C_8$-alkylcarbonyloxy, any of which is optionally substituted in the aryl moiety by at least one substituent selected from $C_1$-$C_8$-alkoxy, halogen, $C_1$-$C_8$-alkylcarbonyl, aminosulfonyl, $C_1$-$C_8$-alkylaminosulfonyl and di($C_1$-$C_8$-alkyl)aminosulfonyl. Preferably acyloxy is $C_1$-$C_4$-alkylcarbonyloxy, or benzoyloxy or phenoxy-$C_1$-$C_4$-alkylcarbonyloxy optionally substituted in the benzene ring thereof by at least one substituent selected from $C_1$-$C_4$-alkoxy, $C_1$-$C_4$-alkylcarbonyl or aminosulfonyl.

"Acylamino" as used herein denotes amino substituted by acyl as hereinbefore defined.

"Halogen" as used herein may be fluorine, chlorine, bromine or iodine; preferably it is fluorine, chlorine or bromine.

"$C_1$-$C_8$-alkoxycarbonyl" as used herein denotes $C_1$-$C_8$-alkoxy as hereinbefore defined attached through the oxygen atom to a carbonyl group.

"Di-($C_1$-$C_8$-alkyl)aminocarbonylmethoxy" as used herein denotes aminocarbonylmethoxy disubstituted on the amino nitrogen atom by $C_1$-$C_8$-alkyl as hereinbefore defined, the two $C_1$-$C_8$-alkyl groups being the same or different.

"Optionally substituted" means the group referred to can be substituted at one or more positions by any one or any combination of the radicals listed thereafter.

In Ar, the phenyl group may be substituted, for example by one, two or three, preferably one or two halogen atoms, preferably selected from fluorine and chlorine atoms, or by one or two $C_1$-$C_8$-alkyl, cyano or nitro groups, or by $C_1$-$C_8$-alkyl and one or two halogen, preferably fluorine or chlorine, atoms. When there is one halogen substituent, it is preferably para to the indicated group X. When there are two or three halogen substituents, preferably one is para to the indicated group X and at least one of the others is ortho to the para-halogen substituent.

$R^3$ as substituted phenyl may, for example, be substituted by one, two, three, four or five, preferably by one, two or three, of the abovementioned substituents. $R^3$ may be, for example, phenyl substituted by one, two or three substituents selected from halogen, cyano, hydroxy, nitro, $C_1$-$C_4$-alkoxy, $C_1$-$C_4$-alkoxycarbonyl, $C_1$-$C_4$-haloalkoxy, —CO—NH$_2$, di($C_1$-$C_4$-alkyl)aminocarbonylmethoxy, $C_1$-$C_4$-alkyl optionally substituted by $C_1$-$C_4$-alkoxy, $C_1$-$C_4$-haloalkyl, $C_1$-$C_4$-alkylcarbonyl, $C_1$-$C_4$-alkylthio, —SO$_2$—NH$_2$, —SO$_2$-$C_1$-$C_4$-alkyl, di($C_1$-$C_4$-alkyl)amino, $C_1$-$C_4$-alkylaminocarbonyl or $C_1$-$C_4$-alkyl-carbonylamino. $R^3$ as substituted phenyl is preferably phenyl substituted by one or more substituents selected from cyano, halogen, $C_1$-$C_4$-alkyl optionally substituted by $C_1$-$C_4$-alkoxy, $C_1$-$C_4$-alkylcarbonyl, $C_1$-$C_4$-alkoxy, $C_1$-$C_4$-alkoxycarbonyl, —CO—NH$_2$, —SO$_2$—NH$_2$, —SO$_2$—$C_1$-$C_4$-alkyl, $C_1$-$C_4$-alkyl-aminocarbonyl, di($C_1$-$C_4$-alkyl)aminocarbonyl-methoxy or $C_1$-$C_4$-alkyl-carbonylamino, especially cyanophenyl, particularly meta-cyanophenyl, and disubstituted phenyl where one substituent is $C_1$-$C_4$-alkoxy or di($C_1$-$C_4$-alkyl)aminocarbonyl-methoxy, preferably ortho to the bond linking $R^3$ to the remainder of the molecule shown in formula I, and the other, preferably para to the $C_1$-$C_4$-alkoxy group, is $C_1$-$C_4$-alkoxy, halogen, cyano or $C_1$-$C_4$-alkyl.

When $R^3$ is $C_1$-$C_4$-alkyl substituted by optionally substituted phenoxy, the substituent(s) on phenoxy may be, for example, one, two or three substituents selected from halogen, cyano, $C_1$-$C_8$-alkyl, $C_1$-$C_8$-alkoxy or $C_1$-$C_8$-alkylcarbonyl.

$R^3$ as a heterocyclic group may be, for example, a group having 5 to 11 ring atoms of which one, two, three or four, preferably one or two, are hetero atoms selected from nitrogen, oxygen or sulfur, such as pyrrolyl, furyl, thienyl, imidazolyl, oxazolyl, thiazolyl, triazolyl, tetrazolyl, pyridyl, pyranyl, pyrazinyl, or a 5-, 6- or 7-membered heterocyclic, ring preferably having one or two oxygen or nitrogen ring atoms, fused to a benzene ring, said heterocyclic group being optionally substituted by substituents including halogen, $C_1$-$C_4$-alkyl optionally substituted by $C_1$-$C_4$-alkoxy, $C_1$-$C_4$-alkoxy, —SO$_2$—$C_1$-$C_8$-alkyl, $C_3$-$C_{10}$-cycloalkyl, phenyl, phenyl-$C_1$-$C_4$-alkyl and $C_2$-$C_4$-alkynyl.

$R^2$ and $R^3$ together with the nitrogen atom to which they are attached as a heterocyclic group may be, for example, a group having a 5- or 6-membered ring of which one, two or three are heteroatoms, optionally fused to a benzene ring, such as piperidyl, piperazinyl, morpholino, or benzopiperidyl, optionally substituted by one or more substituents including $C_1$-$C_8$-alkyl, $C_1$-$C_8$-alkoxy, $C_3$-$C_{10}$-cycloalkyl and halogen.

$R^1$ as optionally substituted $C_1$-$C_8$-alkyl is preferably optionally substituted $C_1$-$C_4$-alkyl, especially $C_1$-$C_4$-alkyl or substituted methyl or ethyl. When $R^1$ is substituted by a cyclic organic group, the latter may be a carbocyclic or heterocyclic group, for example a $C_3$-$C_{15}$-carbocyclic group or a 5- to 7-membered heterocyclic group having one or more, preferably one, two or three, ring hetero atoms selected from nitrogen, oxygen and sulfur. The $C_3$-$C_{15}$-carbocyclic group may be, for example, a cycloaliphatic group having 3 to 8 carbon atoms, preferably $C_5$- or $C_6$-cycloalkyl such as cyclopentyl, methylcyclopentyl or cyclohexyl. The $C_3$-$C_{15}$-carbocyclic group may alternatively be, for example, a $C_6$-$C_{15}$ aromatic group, such as phenyl, which is unsubstituted or substituted by $C_1$-$C_8$-alkyl, $C_1$-$C_8$-alkoxy, halogen, cyano, —CON($R^4$)$R^5$, —SO$_2$N($R^4$)$R^5$ or $C_1$-$C_8$-alkylsulfonylamino where $R^4$ and $R^5$ are as hereinbefore defined. The heterocyclic group may have one nitrogen, oxygen or sulfur atom in the ring or it may have two nitrogens, or one oxygen and one or two nitrogens, or one sulfur and one or two nitrogens in the ring. The heterocyclic group is preferably a heterocyclic aromatic group, especially a 5- or 6-membered heterocyclic group such as furyl, imidazolyl, thiazolyl or pyridyl. Preferred embodiments include those in which $R^1$ is hydrogen or $C_1$-$C_4$-alkyl substituted by hydroxy or $C_1$-$C_4$-alkoxy.

Throughout this specification and in the claims that follow, unless the context requires otherwise, the word "comprise", or variations such as "comprises" or "comprising", will be understood to imply the inclusion of a stated integer or step or group of integers or steps but not the exclusion of any other integer or step or group of integers or steps.

Preferred compounds include those of formula I in free or salt form, where Ar is phenyl substituted by one or two substituents selected from halogen and $C_1$-$C_8$-alkyl;

$R^1$ is hydrogen, $C_1$-$C_4$-alkyl optionally substituted by hydroxy or $C_1$-$C_8$-alkoxy, acyloxy, $C_1$-$C_8$-alkyl substituted by benzoyloxy or phenoxy-$C_1$-$C_4$-alkylcarbonyloxy which are optionally substituted in the benzene ring by at least one substituent selected from $C_1$-$C_8$-alkoxy, $C_1$-$C_8$-alkylcarbonyl and aminosulfonyl, or $C_1$-$C_8$-alkyl substituted by naphthyl;

$R^2$ is hydrogen or $C_1$-$C_8$-alkyl, and $R^3$ is $C_1$-$C_8$-alkyl substituted by phenyl or phenoxy, or $C_1$-$C_8$-alkyl substituted by benzoyloxy or phenoxy-$C_1$-$C_8$-alkylcarbonyloxy which are optionally substituted in the benzene ring by at least one substituent selected from $C_1$-$C_8$-alkoxy, $C_1$-$C_8$-alkylcarbonyl and aminosulfonyl, or $C_1$-$C_8$-alkyl substituted by naphthyl, or $R^3$ is $C_3$-$C_8$-cycloalkyl optionally having a benzo group fused thereto, a heterocyclic group having 5 to 11 ring atoms of which one or two are hetero atoms, selected from nitrogen, oxygen or sulfur, or phenyl, benzyl or naphthyl, said phenyl, phenoxy and naphthyl groups being optionally substituted by one, two or three substituents selected from halogen, cyano, nitro, hydroxy, $C_1$-$C_8$-alkoxy, $C_1$-$C_8$-haloalkoxy, $C_1$-$C_8$-alkyl, $C_1$-$C_8$-alkylcarbonyl, $C_1$-$C_8$-alkylthio, di($C_1$-$C_8$-alkyl)amino or $C_1$-$C_8$-alkylcarbonylamino, or $R^2$ and $R^3$, together with the nitrogen atom to which they are attached, denote a heterocyclic group having a N-heterocyclic ring optionally fused to a benzene ring;

X is —O—, —C(=O)— or —CH$_2$—;

Y is oxygen or sulfur; and m is 1, 2, 3 or 4.

Especially preferred compounds include those of formula I in free or salt form, where Ar is phenyl substituted by one or two substituents selected from halogen and $C_1$-$C_4$-alkyl;

$R^1$ is hydrogen, $C_1$-$C_4$-alkyl optionally substituted by hydroxy or $C_1$-$C_4$-alkoxy, acyloxy, $C_1$-$C_4$-alkyl substituted by benzoyloxy or phenoxy-$C_1$-$C_4$-alkylcarbonyloxy which are optionally substituted in the benzene ring by at least one substituent selected from $C_1$-$C_4$-alkoxy, $C_1$-$C_4$-alkylcarbonyl and aminosulfonyl, or $C_1$-$C_4$-alkyl substituted by naphthyl;

$R^2$ is hydrogen or $C_1$-$C_4$-alkyl, and $R^3$ is $C_1$-$C_4$-alkyl substituted by phenyl or phenoxy, or $C_1$-$C_4$-alkyl substituted by benzoyloxy or phenoxy-$C_1$-$C_4$-alkylcarbonyloxy which are optionally substituted in the benzene ring by at least one substituent selected from $C_1$-$C_4$-alkoxy, $C_1$-$C_4$-alkylcarbonyl and aminosulfonyl, or $C_1$-$C_4$-alkyl substituted by naphthyl, or $R^3$ is $C_5$-$C_8$-cycloalkyl optionally having a benzo group fused thereto, a heterocyclic group having 5 to 11 ring atoms of which one or two are hetero atoms, selected from nitrogen, oxygen or sulfur, or phenyl, benzyl or naphthyl, said phenyl, phenoxy and naphthyl groups being optionally substituted by one, two or three substituents selected from halogen, cyano, nitro, hydroxy, $C_1$-$C_4$-alkoxy, $C_1$-$C_4$-haloalkoxy, $C_1$-$C_4$-alkyl, $C_1$-$C_4$-alkylcarbonyl, $C_1$-$C_4$-alkylthio, di($C_1$-$C_4$-alkyl)amino or $C_1$-$C_4$-alkylcarbonylamino, or $R^2$ and $R^3$, together with the nitrogen atom to which they are attached, denote a heterocyclic group having a N-heterocyclic ring optionally fused to a benzene ring;

X is —O—, —C(=O)— or —CH$_2$—;

Y is oxygen or sulfur; and m is 1, 2, 3 or 4.

In a second aspect the present invention provides compounds of formula I in free or salt form, where Ar is phenyl optionally substituted by one or more substituents selected from halogen, $C_1$-$C_8$-alkyl, cyano or nitro;

$R^1$ is hydrogen or $C_1$-$C_8$-alkyl optionally substituted by hydroxy, $C_1$-$C_8$-alkoxy, acyloxy, halogen, carboxy, $C_1$-$C_8$-alkoxycarbonyl, —N($R^4$)$R^5$, —CON($R^6$)$R^7$ or by a monovalent cyclic organic group having 3 to 15 atoms in the ring system;

$R^2$ is hydrogen or $C_1$-$C_8$-alkyl and $R^3$ is $C_1$-$C_8$-alkyl substituted by phenyl, phenoxy, acyloxy or naphthyl, or $R^3$ is $C_3$-$C_{10}$-cycloalkyl optionally having a benzo group fused thereto, a heterocyclic group having 5 to 11 ring atoms of which 1 to 4 are hetero atoms, phenyl or naphthyl, said phenyl, phenoxy or naphthyl groups being optionally substituted by one or more substituents selected from halogen, cyano, hydroxy, acyl, nitro, —SO$_2$NH$_2$, $C_1$-$C_8$-alkyl optionally substituted by $C_1$-$C_8$-alkoxy, $C_1$-$C_8$-haloalkyl, $C_1$-$C_8$-alkoxy, $C_1$-$C_8$-haloalkoxy, $C_1$-$C_8$-alkylthio, —SO$_2$-$C_1$-$C_8$-alkyl, $C_1$-$C_8$-alkoxycarbonyl, $C_1$-$C_8$-acylamino optionally substituted on the nitrogen atom by $C_1$-$C_8$-alkyl, $C_1$-$C_8$-alkylamino, aminocarbonyl, $C_1$-$C_8$-alkylamino-carbonyl, di($C_1$-$C_8$-alkyl)amino, di($C_1$-$C_8$-alkyl)aminocarbonyl, di($C_1$-$C_8$-alkyl)aminocarbonyl-methoxy, or $R^2$ and $R^3$ together with the nitrogen atom to which they are attached denote a heterocyclic group having 5 to 10 ring atoms of which 1, 2 or 3 are hetero atoms;

$R^4$ and $R^5$ are each independently hydrogen or $C_{1-8}$-alkyl, or $R^4$ is hydrogen and $R^5$ is hydroxy-$C_1$-$C_8$-alkyl, acyl, —SO$^2$R$^8$ or —CON($R^6$)$R^7$, or $R^4$ and $R^5$ together with the nitrogen atom to which they are attached denote a 5-or 6-membered heterocyclic group;

$R^6$ and $R^7$ are each independently hydrogen or $C_1$-$C_8$-alkyl, or $R^6$ and $R^7$ together with the nitrogen atom to which they are attached denote a 5- or 6-membered heterocyclic group;

$R^8$ is $C_1$-$C_8$-alkyl, $C_1$-$C_8$-haloalkyl, or phenyl optionally substituted by $C_1$-$C_8$-alkyl;

X is —C(=O)—, —O—, —CH$_2$—, or CH(OH);

Y is oxygen or sulfur;

m is 1, 2, 3 or 4, and n, p and q are each 0 or 1, n+p+q=1 or 2, n+q=1, p+q=1, and when n is 0, p is 0.

Preferred compounds of formula I in free or salt form include those in which Ar is phenyl substituted by one or two substituents selected from fluorine and chlorine; $R^1$ is hydrogen, $C_1$-$C_4$-alkyl substituted by hydroxy or $C_1$-$C_4$-alkoxy, acyloxy, $C_1$-$C_4$-alkyl substituted by benzoyloxy or phenoxy-$C_1$-$C_4$-alkylcarbonyloxy which are optionally substituted in the benzene ring by at least one substituent selected from $C_1$-$C_4$-alkoxy, $C_1$-$C_4$-alkylcarbonyl and aminosulfonyl, or $C_1$-$C_4$-alkyl substituted by naphthyl;

$R^2$ is hydrogen or $C_1$-$C_4$-alkyl, and $R^3$ is $C_1$-$C_4$-alkyl substituted by phenyl or phenoxy, or $C_1$-$C_4$-alkyl substituted by benzoyloxy or phenoxy-$C_1$-$C_4$-alkylcarbonyloxy which are optionally substituted in the benzene ring by at least one substituent selected from $C_1$-$C_4$-alkoxy, $C_1$-$C_4$-alkylcarbonyl and aminosulfonyl, or $C_1$-$C_4$-alkyl substituted by naphthyl, or $R^3$ is $C_5$-$C_8$-cycloalkyl optionally having a benzo group fused thereto, a heterocyclic group having 5 to 11 ring atoms of which one or two are hetero atoms, selected from nitrogen, oxygen or sulfur, or phenyl, benzyl or naphthyl, said phenyl, phenoxy and naphthyl groups being optionally substituted by one, two or three substituents selected from halogen, cyano, nitro, hydroxy, $C_1$-$C_4$-alkoxy, $C_1$-$C_4$-haloalkoxy, $C_1$-$C_4$-alkyl, $C_1$-$C_4$-alkylcarbonyl, $C_1$-$C_4$-alkylthio, di($C_1$-$C_4$-alkyl)amino or $C_1$-$C_4$-alkylcarbonylamino, or $R^2$ and $R^3$, together with the nitrogen atom to which they are attached, denote a heterocyclic group having a N-heterocyclic ring optionally fused to a benzene ring;

X is —O—, —C(=O)— or —CH$_2$—;

Y is oxygen; and m is 2, 3 or 4.

In a third aspect the present invention provides compounds of formula I in free or salt form, where Ar is phenyl optionally substituted by one or more substituents selected from halogen, $C_1$-$C_8$-alkyl, cyano or nitro;

$R^1$ is hydrogen or $C_1$-$C_8$-alkyl optionally substituted by hydroxy, $C_1$-$C_8$-alkoxy, acyloxy, halogen, carboxy, $C_1$-$C_8$-alkoxycarbonyl, —N($R^4$)$R^5$, —CON($R^6$)$R^7$ or by a monovalent cyclic organic group having 3 to 15 atoms in the ring system;

$R^2$ is hydrogen or $C_1$-$C_8$-alkyl and $R^3$ is $C_1$-$C_8$-alkyl substituted by phenyl, phenoxy, acyloxy or naphthyl, or $R^3$ is $C_3$-$C_{10}$-cycloalkyl optionally having a benzo group fused thereto, a heterocyclic group having 5 to 11 ring atoms of which 1 to 4 are hetero atoms, phenyl or naphthyl, said phenyl, phenoxy or naphthyl groups being optionally substituted by one or more substituents selected from halogen, cyano, hydroxy, acyl, nitro, $C_1$-$C_8$-alkyl, $C_1$-$C_8$-haloalkyl, $C_1$-$C_8$-alkoxy, $C_1$-$C_8$-haloalkoxy, $C_1$-$C_8$-alkylthio, $C_1$-$C_8$-alkoxycarbonyl, acylamino, $C_1$-$C_8$-alkylamino, di($C_1$-$C_8$-alkyl)amino or di($C_1$-$C_8$-alkyl)aminocarbonylmethoxy, or $R^2$ and $R^3$ together with the nitrogen atom to which they are attached denote a heterocyclic group having 5 to 10 ring atoms of which 1, 2 or 3 are hetero atoms;

$R^4$ and $R^5$ are each independently hydrogen or $C_1$-$C_8$-alkyl, or $R^4$ is hydrogen and $R^5$ is hydroxy-$C_1$-$C_8$-alkyl, acyl, —$SO_2R^8$ or —$CON(R^6)R^7$, or $R^4$ and $R^5$ together with the nitrogen atom to which they are attached denote a 5-or 6-membered heterocyclic group;

$R^6$ and $R^7$ are each independently hydrogen or $C_1$-$C_8$-alkyl, or $R^6$ and $R^7$ together with the nitrogen atom to which they are attached denote a 5- or 6-membered heterocyclic group;

$R^8$ is $C_1$-$C_8$-alkyl, $C_1$-$C_8$-haloalkyl, or phenyl optionally substituted by $C_1$-$C_8$-alkyl;

X is —C(=O)—, —O—, —$CH_2$—, or CH(OH);

Y is oxygen or sulfur;

m is 1, 2, 3 or 4; and n, p and q are each 0 or 1, n+p+q=1 or 2, n+q=1, p+q=1, and when n is 0, p is 0.

Preferred compounds of formula I in free or salt form include those in which

Ar is phenyl substituted by one or two substituents selected from fluorine and chlorine;

$R^1$ is hydrogen, $C_1$-$C_4$-alkyl substituted by hydroxy or $C_1$-$C_4$-alkoxy, $C_1$-$C_4$-alkyl substituted by benzoyloxy or phenoxy-$C_1$-$C_4$-alkylcarbonyloxy which are optionally substituted in the benzene ring by at least one substituent selected from $C_1$-$C_4$-alkoxy, $C_1$-$C_4$-alkylcarbonyl and aminosulfonyl, or $C_1$-$C_4$-alkyl substituted by naphthyl;

$R^2$ is hydrogen or $C_1$-$C_4$-alkyl, and $R^3$ is $C_1$-$C_4$-alkyl substituted by phenyl or phenoxy, or $C_1$-$C_4$-alkyl substituted by benzoyloxy or phenoxy-$C_1$-$C_4$-alkylcarbonyloxy which are optionally substituted in the benzene ring by at least one substituent selected from $C_1$-$C_4$-alkoxy, $C_1$-$C_4$-alkylcarbonyl and aminosulfonyl, or $C_1$-$C_4$-alkyl substituted by naphthyl, or $R^3$ is $C_5$-$C_8$-cycloalkyl optionally having a benzo group fused thereto, a heterocyclic group having 5 to 11 ring atoms of which one or two are hetero atoms, selected from nitrogen, oxygen or sulfur, or phenyl, benzyl or naphthyl, said phenyl, phenoxy and naphthyl groups being optionally substituted by one, two or three substituents selected from halogen, cyano, nitro, hydroxy, $C_1$-$C_4$-alkoxy, $C_1$-$C_4$-haloalkoxy, $C_1$-$C_4$-alkyl, $C_1$-$C_4$-alkylcarbonyl, $C_1$-$C_4$-alkylthio, di($C_1$-$C_4$-alkyl)amino or $C_1$-$C_4$-alkylcarbonylamino, or $R^2$ and $R^3$, together with the nitrogen atom to which they are attached, denote a heterocyclic group having a N-heterocyclic ring optionally fused to a benzene ring;

X is —O—, —C(=O)— or —$CH_2$—;

Y is oxygen; and m is 2, 3 or 4.

Especially preferred compounds of formula I in free or salt form include:

(1) Compounds of Formula II

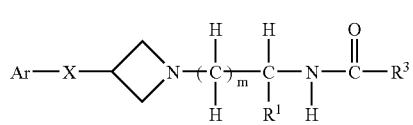

where

Ar is phenyl substituted by one or two substituents selected from fluorine and chlorine, one of said substituents being para to the indicated group X;

$R^1$ is hydrogen, $C_1$-$C_4$-alkyl substituted by hydroxy or $C_1$-$C_4$-alkoxy, $C_1$-$C_4$-alkyl substituted by benzoyloxy or phenoxy-$C_1$-$C_4$-alkylcarbonyloxy which are optionally substituted in the benzene ring by at least one substituent selected from $C_1$-$C_4$-alkoxy, $C_1$-$C_4$-alkylcarbonyl and aminosulfonyl, or $C_1$-$C_4$-alkyl substituted by naphthyl;

$R^3$ is phenyl substituted by one, two or three substituents selected from halogen, cyano, di($C_1$-$C_4$-alkyl)amino, $C_1$-$C_4$-alkylcarbonylamino or $C_1$-$C_4$-alkoxy, or $R^3$ is naphthyl optionally substituted by fluorine, or $R^3$ is $C_1$-$C_4$-alkyl substituted by phenoxy which is optionally substituted by one or two substituents selected from halogen, cyano, $C_1$-$C_4$-alkyl, $C_1$-$C_4$-alkoxy or $C_1$-$C_4$-alkylcarbonyl, or $R^3$ is $C_1$-$C_4$-alkyl substituted by benzoyloxy or phenoxy-$C_1$-$C_4$-alkylcarbonyloxy which are optionally substituted in the benzene ring by at least one substituent selected from $C_1$-$C_4$-alkoxy, $C_1$-$C_4$-alkylcarbonyl and aminosulfonyl, or $R^3$ is a heterocyclic group having a 5- or 6-membered heterocyclic ring in which one or two ring atoms are hetero atoms selected from nitrogen, oxygen and sulfur optionally fused to a benzene ring which is optionally substituted by one or two substituents selected from halogen, $C_1$-$C_4$-alkoxy and $C_1$-$C_4$-alkylcarbonyl;

X is —O—; and m is 2 or 3.

(2) Compounds of Formula III

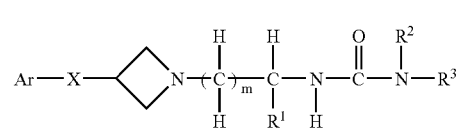

where

Ar is phenyl substituted by one or two substituents selected from fluorine and chlorine, one of said substituents being para to the indicated group X;

$R^1$ is hydrogen, $C_1$-$C_4$-alkyl substituted by hydroxy or $C_1$-$C_4$-alkoxy;

$R^2$ is hydrogen or $C_1$-$C_4$-alkyl and $R^3$ is $C_5$-$C_9$-cycloalkyl, a heterocyclic group having 5 to 11 ring atoms of which one or two are nitrogen or oxygen atoms, phenyl optionally substituted by one, two or three substituents selected from fluorine, chlorine, hydroxy, nitro, $C_1$-$C_4$-alkyl, $C_1$-$C_4$-alkylcarbonyl or $C_1$-$C_4$-alkoxy, phenyl-$C_1$-$C_4$-alkyl substituted in the phenyl group by one or two substituents selected from halogen and $C_1$-$C_4$-alkyl, $C_1$-$C_4$-alkyl substituted by naphthyl, or $C_5$-$C_6$-cycloalkyl having a benzo group fused thereto, or $R^2$ and $R^3$ together with the nitrogen atom to which they are attached denote a heterocyclic group having a 6-membered N-heterocyclic ring fused to a benzene ring which is optionally substituted by up to 2 $C_1$-$C_4$-alkoxy groups;

X is —O— or —C(=O)—; and m is 2 or 3.

(3) Compounds of Formula III Where

Ar is phenyl substituted by chlorine para to the indicated group X and optionally also substituted by chlorine meta to the indicated group X;

$R^1$ is hydrogen or $C_1$-$C_4$-alkyl substituted by hydroxy, $C_1$-$C_4$-alkoxy or $C_1$-$C_4$-acyloxy;

$R^2$ is hydrogen;

$R^3$ is a heterocyclic group having 5 to 11 ring atoms of which 1 to 4 are hetero atoms selected from nitrogen, oxygen and sulphur or atoms, preferably a heterocyclic ring having 5 atoms of which 1 to 4 are heteroatoms selected from nitrogen, oxygen and sulphur substituted by one or two substituents selected from $C_1$-$C_4$-alkyl, $C_3$-$C_6$-cycloalkyl and —$SO_2$—$C_1$-$C_4$-alkyl, or $R^3$ is phenyl optionally substituted by one, two or three substituents selected from halogen, cyano, $C_1$-$C_4$-alkyl optionally substituted by $C_1$-$C_4$-alkoxy, $C_3$-$C_6$-cycloalkyl, $C_1$-$C_4$-alkoxy, $C_1$-$C_4$-alkoxycarbonyl, ($C_1$-$C_4$-alkyl)aminocarbonyl, di($C_1$-$C_4$-alkyl)aminocarbonyl, aminocarbonyl, —$SO_2NH_2$, —$SO_2$—$C_1$-$C_4$-alkyl and $C_1$-$C_4$-acylamino optionally substituted on the nitrogen atom by $C_1$-$C_4$-alkyl;

X is —O—, —$CH_2$— or —C(=O)—; and m is 2.

(4) Compounds of Formula IIIa

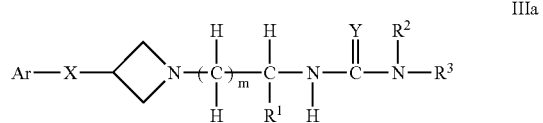

where

Ar is phenyl optionally substituted by fluoro or chloro para to the indicated group X and/or optionally substituted by fluoro, chloro or $C_1$-$C_4$-alkyl meta to the indicated group X;

$R^1$ is hydrogen or $C_1$-$C_4$-alkyl optionally substituted by hydroxy;

$R^2$ is hydrogen or $C_1$-$C_4$-alkyl;

$R^3$ is $C_3$-$C_6$-cycloalkyl, or $R^3$ is a heterocyclic group having 5 to 11 ring atoms of which 1 to 4 are hetero atoms selected from nitrogen, oxygen and sulphur or atoms, preferably a heterocyclic ring having 5 atoms of which 1 to 4 are heteroatoms selected from nitrogen, oxygen and sulphur substituted by one or two substituents selected from $C_1$-$C_4$-alkyl and $C_3$-$C_6$-cycloalkyl, or $R^3$ is phenyl substituted by $C_1$-$C_4$-alkoxy;

X is —O—, —$CH_2$— or —C(=O)—;

Y is O or S; and m is 1 or 2.

(5) Compounds of Formula IV

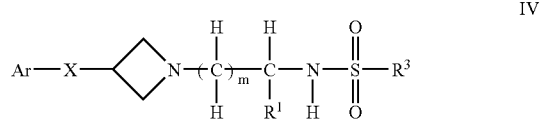

where

Ar is phenyl substituted by one or two substituents selected from fluorine and chlorine, one of said substituents being para to the indicated group X;

$R^1$ is hydrogen or $C_1$-$C_4$-alkyl substituted by hydroxy or $C_1$-$C_4$-alkoxy;

$R^3$ is phenyl optionally substituted by halogen, $C_1$-$C_4$-alkyl or cyano, or $R^3$ is an aromatic N- or S-heterocyclic group having 5 to 10 ring atoms, or $R^3$ is phenyl-$C_1$-$C_4$-alkyl;

X is —O—; and m is 2 or 3.

The compounds represented by formula I are capable of forming acid addition salts, particularly pharmaceutically acceptable acid addition salts. Pharmaceutically acceptable acid addition salts of the compound of formula I include those of inorganic acids, for example, hydrohalic acids such as hydrofluoric acid, hydrochloric acid, hydrobromic acid or hydroiodic acid, nitric acid, sulfuric acid, phosphoric acid; and organic acids, for example aliphatic monocarboxylic acids such as formic acid, acetic acid, trifluoroacetic acid, propionic acid and butyric acid, aliphatic hydroxy acids such as lactic acid, citric acid, tartaric acid or malic acid, dicarboxylic acids such as maleic acid or succinic acid, aromatic carboxylic acids such as benzoic acid, p-chlorobenzoic acid, diphenylacetic acid or triphenylacetic acid, aromatic hydroxy acids such as o-hydroxybenzoic acid, p-hydroxybenzoic acid, 1-hydroxynaphthalene-2-carboxylic acid or 3-hydroxynaphthalene-2-carboxylic acid, and sulfonic acids such as methanesulfonic acid or benzenesulfonic acid. These salts may be prepared from compounds of formula I by known salt-forming procedures.

Compounds of formula I which contain acidic, e.g. carboxyl, groups, are also capable of forming salts with bases, in particular pharmaceutically acceptable bases such as those well known in the art; suitable such salts include metal salts, particularly alkali metal or alkaline earth metal salts such as sodium, potassium, magnesium or calcium salts, or salts with ammonia or pharmaceutically acceptable organic amines or heterocyclic bases such as ethanolamines, benzylamines or pyridine. These salts may be prepared from compounds of formula I by known salt-forming procedures.

When $R^1$ is other than hydrogen, the carbon atom to which $R^1$ is attached in formula I is asymmetric, in which case the compounds exist in individual optically active isomeric forms or as mixtures thereof, e.g. as racemic or diastereomeric mixtures. The invention embraces both individual optically active R and S isomers as well as mixtures, e.g. racemic or diastereomeric mixtures, thereof.

Specific especially preferred compounds of the invention are those described hereinafter in the Examples.

The invention also provides a process for the preparation of compounds of formula I which comprises (i) (A) for the preparation of compounds of formula I where n is 1, p is 1, q is 0 and $R^2$ is hydrogen, reacting a compound of formula V

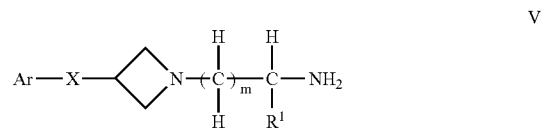

where Ar, X, m and $R^1$ are as hereinbefore defined, with a compound of formula VI

Y=C=N—$R^3$   VI where Y and $R^3$ are as hereinbefore defined, with the proviso that when $R^1$ contains a reactive functional group it may be in protected form, and, where $R^1$ in the product contains a protected functional group, replacing the protecting group by hydrogen;

(B) for the preparation of compounds of formula I where n is 1, p is 1, q is 0 and $R^2$ is hydrogen or $C_1$-$C_8$-alkyl, reacting a compound of formula VII

VII

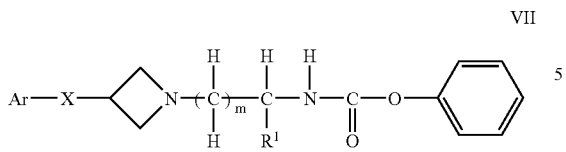

where Ar, X, m and $R^1$ are as hereinbefore defined, with a compound of formula VIII

VIII

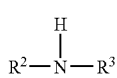

where $R^2$ and $R^3$ are as hereinbefore defined, or and, where $R^1$ in the product contains a protected functional group, replacing the protecting group by hydrogen;

(C) for the preparation of compounds of formula I where n is 1, p is 1, q is 0 and $R^2$ and $R^3$ together with the nitrogen atom to which they are attached denote a heterocyclic group, reacting a compound of formula IX

IX

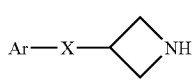

where Ar and X are as hereinbefore defined, with a compound of formula X

X

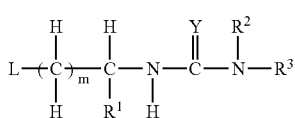

where m, $R^1$ and Y are as hereinbefore defined, $R^2$ and $R^3$ together with the nitrogen atom to which they are attached denote a heterocyclic group having 5 to 10 ring atoms of which one, two or three are hetero atoms, and L is halogen, preferably bromine;

(D) for the preparation of compounds of formula I when n is 1, p is 0, q is 0 and Y is oxygen, reacting a compound of formula IX where Ar and X are as hereinbefore defined, with a compound of formula XI

XI

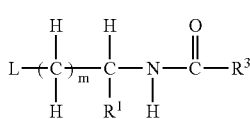

where L, m, $R^1$ and $R^3$ are as hereinbefore defined;

(E) for the preparation of compounds of formula I where n is 1, p is 0, q is 0 and Y is oxygen, reacting a compound of formula V where Ar, X, m and $R^1$ are as hereinbefore defined, with a compound of formula XII

XII

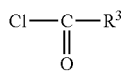

where $R^3$ is as hereinbefore defined, and, where $R^1$ in the product contains a protected functional group, replacing the protecting group by hydrogen;

(F) for the preparation of compounds of formula I where n is 1, p is 0, q is 0, $R^2$ is hydrogen and Y is oxygen, reacting a compound of formula V where Ar, X, m and $R^1$ are as hereinbefore defined, with a compound of formula XIII

XIII

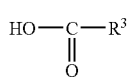

where $R^3$ is as hereinbefore defined, and, where $R^1$ in the product contains a protected functional group, replacing the protecting group by hydrogen;

(G) for the preparation of compounds of formula I where n is 0, p is 0, and q is 1, reacting a compound of formula IX where Ar and X are as hereinbefore defined in the form of a hydrohalide salt with a compound of formula XIV

XIV

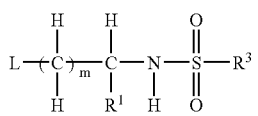

where L, m, $R^1$ and $R^3$ are as hereinbefore defined;

(H) for the preparation of compounds of formula I where n is 1, p is 1, q is 0 and Y is oxygen, reacting a compound of formula V where Ar, X, m and $R^1$ are as hereinbefore defined, with a compound of formula XV

XV

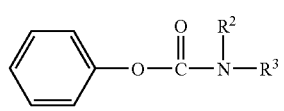

where $R^2$ and $R^3$ are as hereinbefore defined; or (I) for the preparation of compounds of formula I where n is 1, p is 0, q is 0, Y is oxygen and $R^2$ is $C_1$-$C_8$-alkyl or $C_3$-$C_{10}$-cycloalkyl, reacting a compound of formula V where Ar, X, m and $R^1$ are as hereinbefore defined, with a compound of formula XVI

XVI

where $R^2$ is $C_1$-$C_8$-alkyl or $C_3$-$C_{10}$-cycloalkyl, $R^3$ is as hereinbefore defined and Z is a halogen, with the proviso that when $R^1$ contains a reactive functional group it may be in protected form, and, where $R^1$ in the product contains a protected functional group, replacing the protecting group by hydrogen; and (ii) recovering the product in free or salt form.

Process variant (A) may be effected using known procedures for reaction of amines with isocyanates or analogously e.g. as hereinafter described in the Examples. The reaction is conveniently carried out in an organic solvent, for example a halohydrocarbon such as dichloromethane (DCM) or an ether such as dioxane. The reaction temperature may be e.g. from 0° C. to 100° C., conveniently ambient temperature.

Process variant (B) may be effected using known procedures for reaction of carbamic acid phenyl esters with amines or analogously e.g. as hereinafter described in the Examples. The reaction is conveniently carried out in an organic solvent such as dimethyl sulfoxide (DMSO). The reaction temperature may be e.g. from 0 to 100° C., conveniently ambient temperature.

Process variant (C) may be effected using known procedures for reaction of heterocyclic secondary amines with haloalkylureas or analogously e.g. as hereinafter described in the Examples. The reaction is usually effected between the hydrochloride salt of the compound of formula IX and the compound of formula X in the presence of a tertiary amine. The reaction is conveniently effected in an organic solvent, e.g. a halohydrocarbon such as DCM. The reaction temperature may be e.g. from 0 to 100° C., conveniently ambient temperature.

Process variant (D) may be effected using known procedures for reaction of heterocyclic secondary amines with N-(haloalkyl) amides or analogously e.g. as hereinafter described in the Examples. It is usually effected between the hydrochloride salt of the compound of formula IX and the compound of formula XI in the presence of a tertiary amine. Reaction is conveniently effected in an organic solvent such as acetonitrile. The reaction temperature may be e.g. from 0 to 100° C., conveniently ambient temperature.

Process variant (E) may be effected using known procedures for amide-forming reaction of amines with acid halides or analogously.

Process variant (F) may be effected using known procedures for amide formation, for example by reaction in the presence of a tertiary amine and a peptide coupling agent, conveniently in an organic solvent, e.g. a halohydrocarbon such as DCM. The reaction temperature may be e.g. from 0 to 40° C., conveniently ambient temperature.

Process variant (G) may be effected using known procedures for reaction of heterocyclic secondary amines with N-(haloalkyl) sulfonamides or analogously e.g. as hereinafter described in the Examples. It is usually effected in the presence of a tertiary amine, conveniently in an organic solvent such as acetonitrile. The reaction temperature may be e.g. from 0 to 100° C., conveniently ambient temperature.

Process variant (H) may be effected using known procedures for reaction of amines with carbamic acid phenyl esters or analogously e.g. as hereinafter described in the Examples. The reaction is conveniently carried out in an organic solvent such as dimethyl sulfoxide (DMSO). The reaction temperature may be e.g. from 20 to 100° C., conveniently ambient temperature.

Process variant (I) may be effected using known procedures for amide-forming reaction of amines with haloformamides or analogously e.g. as hereinafter described in the Examples. The reaction temperature may be e.g. from 0 to 40° C., conveniently ambient temperature.

Compounds of formula V may be prepared by reacting a compound of formula IX with a compound of formula XVII

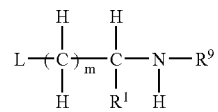

XVII where $R^1$, L and m are as hereinbefore defined, with the proviso that when $R^1$ contains a reactive functional group such as a hydroxy group, the reactive group may be in protected form, for example a hydroxy group protected as a tert-butoxy group, and $R^9$ is hydrogen or an amine-protective group, for example a tert-butoxycarbonyl group, and, where $R^9$ is a protective group, replacing $R^9$ in the product by hydrogen, and, where $R^1$ in the product contains a protected functional group, replacing the protecting group by hydrogen. When $R^9$ is hydrogen, reaction between a compound of formula XVII and a salt of a compound of formula IX may be effected by the procedures described in U.S. Pat. No. 4,559,349. When $R^9$ is a protective group, reaction between compounds of formulae XVII and IX may be effected using known methods, for example in the presence of a tertiary organic base such as triethylamine or 1,8-diaza-bicyclo [5.4.0]undec-7-ene (DBU), conveniently in an inert organic solvent, for example a polar solvent such as dimethylformamide, the reaction temperature suitably being from 0 to 40° C., preferably ambient temperature. Replacement of a protective group $R^9$ by hydrogen may be effected using known procedures; for example, where $R^9$ is tert-butoxycarbonyl, by treatment with a carboxylic acid such as trifluoroacetic acid. Replacement of a protecting group in $R^1$ may be affected using known procedures, for example, when $R^1$ contains a hydroxy group protected as an ether group, such as tert-butoxy, by treatment with HBr in a carboxylic acid such as acetic acid; when $R^9$ is a protective group, this treatment also replaces $R^9$ by hydrogen.

Where reference is made herein to protected functional groups or to protecting groups, the protecting groups may be chosen in accordance with the nature of the functional group, for example as described in Protective Groups in Organic Synthesis, T. W. Greene and P. G. M. Wuts, John Wiley & Sons Inc, Second Edition, 1991, which reference also describes procedures suitable for replacement of the protecting groups by hydrogen.

Compounds of formulae VI are commercially available or may be prepared by known methods.

Compounds of formula VII may be prepared by reacting a compound of formula V with phenyl chloroformate in the presence of a base such as a tertiary amine, for example as hereinafter described in the Examples.

Compounds of formulae VIII are commercially available or may be prepared by known methods.

Compounds of formula IX where X is —O— may be prepared by reacting a compound of formula XVIII

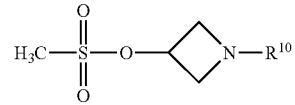

XVIII with a compound of formula Ar—OH in the presence of sodium hydride, where Ar is as hereinbefore defined and $R^{10}$ is a protecting group, and replacing $R^{10}$ in the product by hydrogen. The reaction may be carried out in an inert organic solvent such as DMF. Suitable reaction temperatures may be from 20° C. to 150° C., conveniently from 50 to 70° C. The replacement of $R^{10}$ by hydrogen may be affected using known procedures, for example where $R^{10}$ is benzhydryl by reacting the product of the reaction of the compound of formula XVII and $Ar^1$—OH with 1-chloroethyl chloroformate, a suitable reaction temperature being 10-30° C., conveniently at room temperature.

Compounds of formula IX where X is —C(=O)— may be prepared by reacting a compound of formula XIXa or formula XIXb

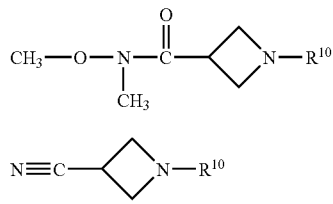

XIXa

XIXb with a compound of formula XX

Ar—MgBr    XX where Ar and $R^{10}$ are as hereinbefore defined, and replacing $R^{10}$ in the product by hydrogen. Reaction of compounds of formulae XIXa/b and XX may be effected in an inert organic solvent, e.g. an ether such as THF and/or diethyl ether; suitable reaction temperatures may be from −10° C. to 10° C., conveniently from −5 to 5° C. Replacement of $R^{10}$ in the product by hydrogen may be effected as hereinbefore described.

Compounds of formula IX where X is —CH$_2$— are novel and may be prepared by reduction of compounds of formula IX where X is —C(=O)—, for example using known reduction procedures. This preferably involves of reduction to the corresponding alcohol, conversion to the iodine and then reduction.

Compounds of formula X may be prepared by reaction of a compound of formula XXI

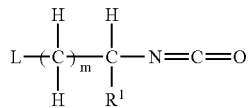

XXI with a compound of formula H—N(R$^2$)R$^3$ where L, R$^1$, R$^2$ and R$^3$ are as defined in formula X, for example as hereinafter described in the Examples.

Compounds of formula XI may be prepared by reaction of a compound of formula XXII

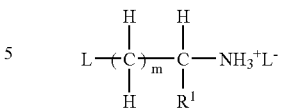

XXII with a compound of formula XIII, for example as hereinafter described in the Examples.

Compounds of formulae XII and XIII are known or may be prepared by known procedures.

Compounds of formula XIV may be prepared by reacting a compound of formula XXII with a compound of formula R$^3$SO$_2$Cl, for example as hereinafter described in the Examples.

Compounds of formulae XV, XVI, XVII, XVIII are known or may be prepared by known procedures.

Compounds of formula XIXa may be prepared by reacting a compound of formula XXIII

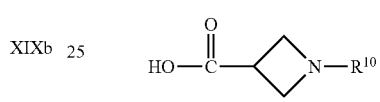

XXIII with O,N-dimethylhydroxylamine hydrochloride in the presence of a peptide coupling agent such as di-imidazol-1-yl-methanone, conveniently in an inert organic solvent such as THF, suitably at reflux temperature.

Compounds of formulae XIXb, XX, XX, XXII and XXII are known or may be prepared using known procedures.

Compounds of formula I in free form may be converted into salt form, and vice versa, in a conventional manner. The compounds in free or salt form can be obtained in the form of hydrates or solvates containing a solvent used for crystallization. Compounds of formula I can be recovered from reaction mixtures and purified in a conventional manner. Isomers, such as enantiomers, may be obtained in a conventional manner, e.g. by fractional crystallization or asymmetric synthesis from correspondingly asymmetrically substituted, e.g. optically active, starting materials.

Compounds of formula I in free or pharmaceutically acceptable salt form, hereinafter referred to alternatively as agents of the invention, are useful as pharmaceuticals. Accordingly the invention also provides a compound of formula I in free or pharmaceutically acceptable salt form for use as a pharmaceutical. The agents of the invention act as CCR-3 receptor antagonists, thereby inhibiting the infiltration and activation of inflammatory cells, particularly eosinophils, and inhibiting allergic response. The inhibitory properties of agents of the invention can be demonstrated in the following assay:

CCR-3 Binding Assay

In this assay the effect of agents of the invention on the binding of human eotaxin to human CCR-3 is determined. Recombinant cells expressing human CCR-3 are captured by wheatgerm agglutinin (WGA) polyvinyltoluidene (PVT) SPA beads (available from Amersham), through a specific interaction between the WGA and carbohydrate residues of glycoproteins on the surface of the cells. [$^{125}$I]-human eotaxin (available from Amersham) binds specifically to CCR-3 receptors bringing the [$^{125}$I]-human eotaxin in close proximity to the SPA beads. Emitted â-particles from the [$^{125}$I]-human eotaxin excite, by its proximity, the fluorophore in the beads and produce light. Free [$^{125}$I]-human eotaxin in solution is not in close proximity to the scintillant and hence does not produce light. The scintillation count is therefore a measure of the extent to which the test compound inhibits binding of the eotaxin to the CCR-3.

Preparation of Assay Buffer: 5.96 g HEPES and 7.0 g sodium chloride are dissolved in distilled water and 1M aqueous $CaCl_2$ (1 ml) and 1M aqueous $MgCl_2$ (5 ml) are added. The pH is adjusted to 7.6 with NaOH and the solution made to a final volume of 1 L using distilled water. 5 g bovine serum albumin and 0.1 g sodium azide are then dissolved in the solution and the resulting buffer stored at 4° C. A Complete™ protease inhibitor cocktail tablet (available from Boehringer) is added per 50 ml of the buffer on the day of use.

Preparation of Homogenisation Buffer: Tris-base (2.42 g) is dissolved in distilled water, the pH of the solution is adjusted to 7.6 with hydrochloric acid and the solution is diluted with distilled water to a final volume of 1 l. The resulting buffer is stored at 4° C. A Complete™ protease inhibitor cocktail tablet is added per 50 ml of the buffer on the day of use.

Preparation of membranes: Confluent rat basophil leukemia (RBL-2H3) cells stably expressing CCR3 are removed from tissue culture flasks using enzyme-free cell dissociation buffer and resuspended in phosphate-buffered saline. The cells are centrifuged (800 g, 5 minutes), the pellet resuspended in ice-cold homogenisation buffer using 1 ml homogenisation buffer per gram of cells and incubated on ice for 30 minutes. The cells are homogenised on ice with 10 strokes in a glass mortar and pestle. The homogenate is centrifuged (800 g, 5 minutes, 4° C.), the supernatant further centrifuged (48,000 g, 30 minutes, 4° C.) and the pellet redissolved in Homogenisation Buffer containing 10% (v/v) glycerol. The protein content of the membrane preparation is estimated by the method of Bradford (Anal. Biochem. (1976) 72:248) and aliquots are snap frozen and stored at −80° C.

The assay is performed in a final volume of 250 µl per well of an Optiplate™ microplate (ex Canberra Packard). To selected wells of the Optiplate™ are added 50 µl of solutions of a test compound in Assay Buffer containing 5% DMSO (concentrations from 0.01 nM to 10 µM). To determine total binding, 50 µl of the Assay Buffer containing 5% DMSO is added to other selected wells. To determine non-specific binding, 50 µl of 100 nM human eotaxin (ex R&D Systems) in Assay Buffer containing 5% DMSO is added to further selected wells. To all wells are added 50 µl [$^{125}$I]-Human eotaxin (ex Amersham) in Assay Buffer containing 5% DMSO at a concentration of 250 µM (to give a final concentration of 50 µM per well), 50 µl of WGA-PVT SPA beads in Assay Buffer (to give a final concentration of 1.0 mg beads per well) and 100 µl of the membrane preparation at a concentration of 100 µg protein in Assay Buffer (to give a final concentration of 10 µg protein per well). The plate is then incubated for 4 hours at room temperature. The plate is sealed using TopSeal-S™ sealing tape (ex Canberra Packard) according to the manufacturers instructions. The resulting scintillations are counted using a Canberra Packard TopCount™ scintillation counter, each well being counted for 1 minute. The concentration of test compound at which 50% inhibition occurs ($IC_{50}$) is determined from concentration-inhibition curves in a conventional manner.

The compounds of the Examples hereinbelow generally have $IC_{50}$ values below 1 µM in the above assay. For instance, the compounds of Examples 16, 26, 37, 45, 83, 88, 99, 122, 134, 190 and 195 have $IC_{50}$ values of 0.103 µM, 0.007 µM, 0.018 µM, 0.011 µM, 0.005 µM, 0.006 µM, 0.007 µM, 0.022 µM, 0.012 µM, 0.011 µM, and 0.002 µM respectively.

Most of the compounds of the Examples exhibit selectivity for inhibition of CCR-3 binding relative to inhibition of binding of the alpha-1 adrenergic receptor. Some of the compounds, e.g. that of Example 190, are also histamine H1 antagonists. The inhibitory properties of agents of the invention on binding of the alpha-1 adrenergic receptor can be determined in the following assay:

Cerebral cortices from male Sprague-Dawley rats (175-200 g) are dissected and homogenised in 10 volumes of ice cold 0.32 M sucrose (containing 1 mM $MgCl_2$ dihydrate and 1 mM $K_2HPO_4$) with a glass/teflon homogeniser. The membranes are centrifuged at 1000×g for 15 miN, the pellet discarded and the centrifugation repeated. The supernatants are pooled and centrifuged at 18,000×g for 15 minutes. The pellet is osmotically shocked in 10 volumes of water and kept on ice for 30 minutes. The suspension is centrifuged at 39,000×g for 20 minutes, resuspended in Krebs-Henseleit buffer pH 7.4 (1.17 mM $MgSO_4$ anhydrous, 4.69 mM KCl, 0.7 mM $K_2HPO_4$ anhydrous, 0.11 M NaCl, 11 mM D-glucose and 25 mM $NaHCO_3$) containing 20 mM Tris, and kept for 2 days at −20° C. The membranes are then thawed at 20-23° C., washed three times with Krebs-Henseleit buffer by centrifugation at 18,000×g for 15 minutes, left overnight at 4° C. and washed again three times. The final pellet is resuspended with a glass/teflon homogeniser in 125 ml/100 membranes in the same buffer. A sample is taken to determine the protein concentration (using the Bradford Assay with gamma globulin as the standard) and the remainder aliquoted and stored at −80° C.

The resulting membranes are subjected to a radioligand binding assay. The assay is conducted in triplicate using 96 well plates containing [$^{125}$I]-HEAT (Amersham) (40 pM, $K_d$: 58.9±18.7 pM), unlabelled test compound and membrane (57.1 µg/ml) to yield a final volume of 250 µl (assay buffer containing 50 mM Tris-base and 0.9% (w/v) NaCl, pH 7.4). The plates are incubated at 37° C. for 60 minutes, after which rapid vacuum filtration over Whatman™ GF/C 96 well filter plates is carried out. Each plate is then washed three times with 10 ml of ice cold assay buffer using a Brandel Cell harvester (Gaithersburg, Md.). Following drying of the plates for 3 h. at 50° C., 40 µl of Microscint 20 is added to each well, the plates incubated at room temperature for a further 20 minutes and the retained radioactivity quantified in a Packard TopCount NXT™ scintillation counter.

Stock solutions of test compounds are dissolved initially in 100% DMSO and diluted with assay buffer to the required concentrations to yield 1% (v/v) DMSO.

The concentration of test compound at which 50% inhibition occurs ($IC_{50}$) is determined from concentration-inhibition curves in a conventional manner.

Having regard to their inhibition of binding of CCR-3, agents of the invention are useful in the treatment of conditions mediated by CCR-3, particularly inflammatory or allergic conditions. Treatment in accordance with the invention may be symptomatic or prophylactic. Accordingly, agents of the invention are useful in the treatment of inflammatory or obstructive airways diseases, resulting, for example, in reduction of tissue damage, bronchial hyperreactivity, remodelling or disease progression. Inflammatory or obstructive airways diseases to which the present invention is applicable include asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial or viral infection. Treatment of asthma is also to be understood as embracing treatment of subjects, e.g. of less than 4 or 5 years of age, exhibiting wheezing symptoms and diagnosed or diagnosable as "wheezy infants", an established patient category of major medical concern and now often identified as incipient or early-phase asthmatics. (For convenience this particular asthmatic condition is referred to as "wheezy-infant syndrome".)

Prophylactic efficacy in the treatment of asthma will be evidenced by reduced frequency or severity of symptomatic attack, e.g. of acute asthmatic or bronchoconstrictor attack, improvement in lung function or improved airways hyperreactivity. It may further be evidenced by reduced requirement for other, symptomatic therapy, i.e. therapy for or intended to restrict or abort symptomatic attack when it occurs, for example anti-inflammatory (e.g. corticosteroid) or bronchodilatory. Prophylactic benefit in asthma may in particular be apparent in subjects prone to "morning dipping". "Morning dipping" is a recognised asthmatic syndrome, common to a substantial percentage of asthmatics and characterised by asthma attack, e.g. between the hours of about 4 to 6 am, i.e. at a time normally substantially distant form any previously administered symptomatic asthma therapy.

Other inflammatory or obstructive airways diseases and conditions to which the present invention is applicable include acute lung injury (ALI), acute/adult respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy. The invention is also applicable to the treatment of bronchitis of whatever type or genesis including, e.g., acute, arachidic, catarrhal, croupus, chronic or phthinoid bronchitis. Further inflammatory or obstructive airways diseases to which the present invention is applicable include pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis.

Having regard to their anti-inflammatory activity, in particular in relation to inhibition of eosinophil activation, agents of the invention are also useful in the treatment of eosinophil related disorders, e.g. eosinophilia, in particular eosinophil related disorders of the airways (e.g. involving morbid eosinophilic infiltration of pulmonary tissues) including hypereosinophilia as it effects the airways and/or lungs as well as, for example, eosinophil-related disorders of the airways consequential or concomitant to Löffler's syndrome, eosinophilic pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction.

Agents of the invention are also useful in the treatment of inflammatory or allergic conditions of the skin, for example psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, pemphisus, epidermolysis bullosa acquisita, and other inflammatory or allergic conditions of the skin. Agents of the invention may also be used for the treatment of other diseases or conditions, in particular diseases or conditions having an inflammatory component, for example, treatment of diseases and conditions of the eye such as conjunctivitis, keratoconjunctivitis sicca, and vernal conjunctivitis, diseases affecting the nose including allergic rhinitis, e.g. atrophic, chronic, or seasonal rhinitis, inflammatory conditions of the gastrointestinal tract, for example inflammatory bowel disease such as ulcerative colitis and Crohn's disease, diseases of the bone and joints including rheumatoid arthritis, psoriatic arthritis, ankylosing spondylitis and systemic sclerosis, and other diseases such as atherosclerosis, multiple sclerosis, diabetes (type I), myasthenia gravis, hyper IgE syndrome and acute and chronic allograft rejection, e.g. following transplantation of heart, kidney, liver, lung or bone marrow.

The effectiveness of an agent of the invention in inhibiting inflammatory conditions, for example in inflammatory airways diseases, may be demonstrated in an animal model, e.g. a mouse or rat model, of airways inflammation or other inflammatory conditions, for example as described by Szarka et al, J. Immunol. Methods (1997) 202:49-57; Renzi et al, Am. Rev. Respir. Dis. (1993) 148:932-939; Tsuyuki et al., J. CliN Invest. (1995) 96:2924-2931; and Cernadas et al (1999) Am. J. Respir. Cell Mol. Biol. 20:1-8.

The agents of the invention are also useful as co-therapeutic agents for use in combination with other drug substances such as anti-inflammatory, bronchodilatory or anti-histamine drug substances, particularly in the treatment of obstructive or inflammatory airways diseases such as those mentioned hereinbefore, for example as potentiators of therapeutic activity of such drugs or as a means of reducing required dosaging or potential side effects of such drugs. An agent of the invention may be mixed with the other drug substance in a fixed pharmaceutical composition or it may be administered separately, before, simultaneously with or after the other drug substance. Such anti-inflammatory drugs include steroids, in particular gluco-corticosteroids such as budesonide, beclamethasone, fluticasone, ciclesonide or mometasone, LTB4 antagonists such as those described in U.S. Pat. No. 5,451,700, LTD4 antagonists such as montelukast and zafirlukast, dopamine receptor agonists such as cabergoline, bromocriptine, ropinirole and 4-hydroxy-7-[2-[[2-[[3-(2-phenylethoxy)propyl]sulfonyl]ethyl]amino] ethyl]-2(3H)-benzothiazolone and pharmaceutically acceptable salts thereof (the hydrochloride being Viozan®-AstraZeneca), and PDE4 inhibitors such as Ariflo® (GlaxoSmith Kline), Roflumilast (Byk Gulden), V-11294A (Napp), BAY19-8004 (Bayer), SCH-351591 (Schering-Plough), Arofylline (Almirall Prodesfarma) and PD189659 (Parke-Davis). Such bronchodilatory drugs include anticholinergic or antimuscarinic agents, in particular ipratropium bromide, oxitropium bromide and tiotropium bromide, and beta-2 adrenoceptor agonists such as salbutamol, terbutaline, salmeterol and, especially, formoterol and pharmaceutically acceptable salts thereof, and compounds (in free or salt or solvate form) of formula I of PCT International Publication No. WO 00/75114, which document is incorporated herein by reference, preferably compounds of the Examples thereof, especially a compound of formula

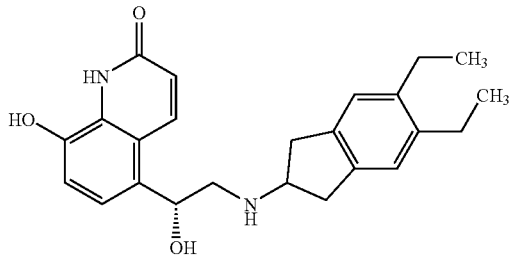

and pharmaceutically acceptable salts thereof. Co-therapeutic antihistamine drug substances include cetirizine hydrochloride, acetaminophen, clemastine fumarate, promethazine, loratidine, desloratidine, diphenhydramine and fexofenadine hydrochloride. Combinations of agents of the invention and steroids, beta-2 agonists, PDE4 inhibitors or LTD4 antagonists may be used, for example, in the treatment of COPD or, particularly, asthma. Combinations of agents of the invention and anticholinergic or antimuscarinic agents, PDE4 inhibitors, dopamine receptor agonists or LTB4 antagonists may be used, for example, in the treatment of asthma or, particularly, COPD.

Other useful combinations of agents of the invention with anti-inflammatory drugs are those with other antagonists of chemokine receptors, e.g. CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists such as Schering-Plough antagonists SC-351125, SCH-55700 and SCH-D, Takeda antagonists such as N-[[4-[[[6,7-dihydro-2-(4-methylphenyl)-5H-benzocyclohepten-8-yl]carbonyl]amino]phenyl]-methyl]tetrahydro-N,N-dimethyl-2H-pyran-4-aminium chloride (TAK-770), CCR-5 antagonists described in U.S. Pat. No. 6,166,037 (particularly claims 18 and 19), WO 00/66558 (particularly claim 8), and WO 00/66559 (particularly claim 9).

In accordance with the foregoing, the invention also provides a method for the treatment of a condition mediated by CCR-3, for example an inflammatory or allergic condition, particularly an inflammatory or obstructive airways disease, which comprises administering to a subject, particularly a human subject, in need thereof an effective amount of a compound of formula I in a free or pharmaceutically acceptable salt form as hereinbefore described. In another aspect the invention provides the use of a compound of formula I, in free or pharmaceutically acceptable salt form, as hereinbefore described for the manufacture of a medicament for the treatment of a condition mediated by CCR-3, for example an inflammatory or allergic condition, particularly an inflammatory or obstructive airways disease.

The agents of the invention may be administered by any appropriate route, e.g. orally, for example in the form of a tablet or capsule; parenterally, for example intravenously; by inhalation, for example in the treatment of inflammatory or obstructive airways disease; intranasally, for example in the treatment of allergic rhinitis; topically to the skin, for example in the treatment of atopic dermatitis; or rectally, for example in the treatment of inflammatory bowel disease.

In a further aspect, the invention also provides a pharmaceutical composition comprising as active ingredient a compound of formula I in free or pharmaceutically acceptable salt form, optionally together with a pharmaceutically acceptable diluent or carrier therefor. The composition may contain a co-therapeutic agent such as an anti-inflammatory bronchodilatory or antihistamine drug as hereinbefore described. Such compositions may be prepared using conventional diluents or excipients and techniques known in the galenic art. Thus oral dosage forms may include tablets and capsules. Formulations for topical administration may take the form of creams, ointments, gels or transdermal delivery systems, e.g. patches. Compositions for inhalation may comprise aerosol or other atomizable formulations or dry powder formulations.

When the composition comprises an aerosol formulation, it preferably contains, for example, a hydro-fluoro-alkane (HFA) propellant such as HFA134a or HFA227 or a mixture of these, and may contain one or more co-solvents known in the art such as ethanol (up to 20% by weight), and/or one or more surfactants such as oleic acid or sorbitan trioleate, and/or one or more bulking agents such as lactose. When the composition comprises a dry powder formulation, it preferably contains, for example, the compound of formula I having a particle diameter up to 10 microns, optionally together with a diluent or carrier, such as lactose, of the desired particle size distribution and a compound that helps to protect against product performance deterioration due to moisture. When the composition comprises a nebulised formulation, it preferably contains, for example, the compound of formula I either dissolved, or suspended, in a vehicle containing water, a co-solvent such as ethanol or propylene glycol and a stabiliser, which may be a surfactant.

The invention includes (A) an agent of the invention in inhalable form, e.g. in an aerosol or other atomisable composition or in inhalable particulate, e.g. micronised form, (B) an inhalable medicament comprising an agent of the invention in inhalable form; (C) a pharmaceutical product comprising such an agent of the invention in inhalable form in association with an inhalation device; and (D) an inhalation device containing an agent of the invention in inhalable form.

Dosages of agents of the invention employed in practising the present invention will of course vary depending, for example, on the particular condition to be treated, the effect desired and the mode of administration. In general, suitable daily dosages for administration by inhalation are of the order of 0.01 to 30 mg/kg while for oral administration suitable daily doses are of the order of 0.01 to 100 mg/kg.

The invention is illustrated by the following Examples.

EXAMPLES 1-19

Compounds of formula II are shown in the following table, the methods of preparation being described hereinafter. The table also shows characterising mass spectrometry data. X is O except in Example 7 where it is C=O. The value of m in formula II is 2. The compounds are all in free form.

| Ex. | Ar | R¹ | R³ | MS [M + H] |
|---|---|---|---|---|
| 1 | 4-F-C₆H₄- | -O-C(CH₃)₂-CH₂-O-CH₂CH₃ (tert-butyl ethyl ether group) | 3,4,5-trimethoxyphenyl | 505.3 |
| 2 | 4-F-C₆H₄- | -CH₂-OH | 3,4,5-trimethoxyphenyl | 449.1 |
| 3 | 4-F-C₆H₄- | -CH₂-OH | 3,4-difluorophenyl | |
| 4 | 4-F-C₆H₄- | H | 3-ethoxy-4-methoxy-5-cyanophenyl | 414.1 |
| 5 | 4-F-C₆H₄- | H | quinolin-3-yl | 380.1 |
| 6 | 4-F-C₆H₄- | H | 5-fluoro-2-methyl-1H-indol-3-yl | 386.1 |
| 7 | 4-F-C₆H₄- | H | 4-chloro-2-methoxy-3-methylphenyl (substituted) | 405.0 |
| 8 | 4-F-C₆H₄- | H | 7-methoxy-2-methylbenzofuran-3-yl | 399.1 |
| 9 | 4-F-C₆H₄- | H | 4-chloro-ethoxyphenyl | 393.1 |

-continued
| Ex. | Ar | R¹ | R³ | MS [M + H] |
|---|---|---|---|---|
| 10 | 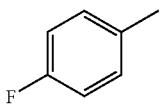 | H | 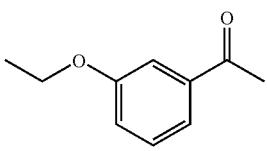 | 401.1 |
| 11 | 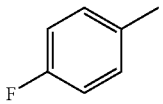 | H | 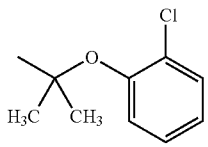 | 421.1 |
| 12 | 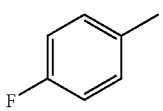 | H | 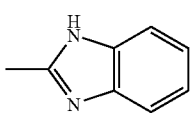 | 369.1 |
| 13 | 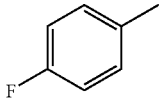 | H | 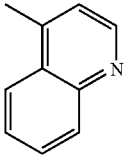 | 380.0 |
| 14 | 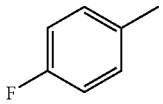 | 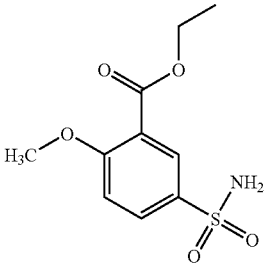 | 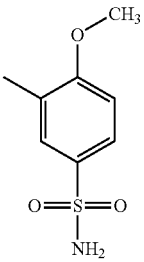 | 681.4 |
| 15 | 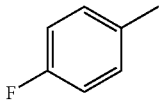 | 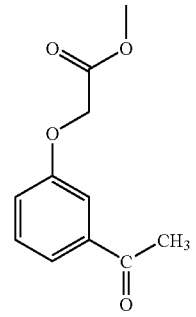 | 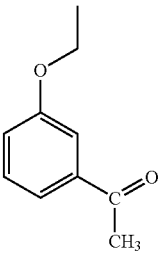 | 607.3 |
| 16 | 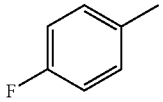 | H | 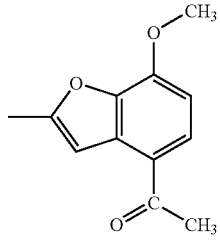 | 442.2 |

-continued

| Ex. | Ar | $R^1$ | $R^3$ | MS [M + H] |
|---|---|---|---|---|
| 17 | 4-F-phenyl | HO-CH2-CH(-)- | 3-ethoxyphenyl-C(=O)-CH3 (1-(3-ethoxyphenyl)ethanone linkage) | 431.2 |
| 18 | 4-F-phenyl | HO-CH2-CH(-)- | 7-methoxy-2-methylbenzofuran | 428.8 |
| 19 | 4-F-phenyl | H | 7-(1-ethoxy)-2-methylbenzofuran | 412.5 [M+] |

EXAMPLES 20-57

Compounds of formula III are shown in the following table, the methods of preparation being described hereinafter. The table also shows characterising mass spectrometry data. X is O except in Examples 34, 37 and 49, where it is C=O. $R^2$ is hydrogen except in Example 54 where it is $CH_3$, and in Example 55 where $R^2$ and $R^3$ together with the attached nitrogen atom denote the group shown in the $R^3$ column. The value of m in formula III is 2 for Examples 20-56 and 3 for Example 57. Examples 24-25, 27, 29-33 and 36 are in the form of the trifluoroacetate salt; the others are in free form.

| Ex. | Ar | $R^1$ | $R^3$ | MS [M + H] |
|---|---|---|---|---|
| 20 | 4-F-phenyl | H | 3,5-dimethoxyphenyl | 404.1 |
| 21 | 4-F-phenyl | CH2OH | 3,5-dimethoxyphenyl | 434.1 |
| 22 | 4-F-phenyl | H | 4-F-phenyl | 362.1 |
| 23 | 4-F-phenyl | H | 3,4-difluorophenyl | 380.1 |
| 24 | 4-F-phenyl | H | 1-(naphthalen-1-yl)ethyl | 422.1 |
| 25 | 4-F-phenyl | H | adamantyl | 402.2 |
| 26 | 4-Cl-phenyl | CH2OH | 3,5-dimethoxyphenyl | 450.0 |
| 27 | 4-F-phenyl | H | 3-ethylphenyl (via CH2 linker with CH3) | 372.2 |

-continued

| Ex. | Ar | R¹ | R³ | MS [M + H] |
|---|---|---|---|---|
| 28 | 4-Cl-phenyl | CH₂OH | 3,4-difluorophenyl | 426.2 |
| 29 | 4-Cl-phenyl | CH₂OH | 3-methoxyphenyl | 420.2 |
| 30 | 4-F-phenyl | H | 2,3-dimethylphenyl | 372.2 |
| 31 | 4-Cl-phenyl | CH₂OH | 2,3-dichlorophenyl | 458.2 |
| 32 | 4-Cl-phenyl | CH₂OH | 4-fluorophenyl | 408.2 |
| 33 | 4-Cl-phenyl | CH₂OH | 2-chloro-ethylphenyl | 438.2 |
| 34 | 4-F-phenyl | CH₂OH | 3,5-dimethoxyphenyl | 446.1 |
| 35 | 3,4-diCl-phenyl | CH₂OH | 3,5-dimethoxyphenyl | 484.0 |
| 36 | 4-F-phenyl | H | 2,3-dihydrobenzofuran-5-yl | 386.1 |
| 37 | 4-Cl-phenyl | CH₂OH | 3,5-dimethoxyphenyl | 461.8 |

-continued

| Ex. | Ar | R¹ | R³ | MS [M + H] |
|---|---|---|---|---|
| 38 | 4-Cl-phenyl | CH₂OH | 3-chlorophenyl | 423.6 |
| 39 | 4-Cl-phenyl | CH₂OH | 3-ethylphenyl | 417.5 |
| 40 | 4-Cl-phenyl | CH₂OH | 3-acetylphenyl | 431.7 |
| 41 | 4-Cl-phenyl | CH₂OH | 2,3-dimethylphenyl | 418.0 |
| 42 | 4-Cl-phenyl | CH₂OH | indan-2-yl | 429.9 |
| 43 | 4-F-phenyl | H | 3-hydroxyphenyl | 360.1 |
| 44 | 4-Cl-phenyl | CH₂OH | 2,4-dimethylphenyl | 418.0 |
| 45 | 4-Cl-phenyl | CH₂OH | 4-methylphenyl | 403.6 |
| 46 | 4-Cl-phenyl | CH₂OH | 4-methoxyphenyl | 419.8 |
| 47 | 4-Cl-phenyl | CH₂OH | 2,4-difluorophenyl | 425.5 |

-continued

| Ex. | Ar | R¹ | R³ | MS [M + H] |
|---|---|---|---|---|
| 48 | 4-Cl-phenyl | CH₂OH | 2-methyl-4-methoxy-phenyl with OCH₃ | 449.9 |
| 49 | 3,4-diCl-phenyl | CH₂OH | 3,5-dimethoxyphenyl | 495.6 |
| 50 | 4-Cl-phenyl | CH₂OH | 3,4-dimethylphenyl | 417.8 |
| 51 | 4-Cl-phenyl | CH₂OH | 3,5-difluorophenyl | 425.7 |
| 52 | 4-F-phenyl | CH₂OH | 3,4,5-trimethoxyphenyl | 464.2 |
| 53 | 4-Cl-phenyl | H | 3,5-dimethoxyphenyl | 420.1 |
| 54 | 4-F-phenyl | H | phenyl | 364.0 |
| 55 | 4-F-phenyl | H | N-methyl-1,2,3,4-tetrahydroquinolinyl | 384.1 |
| 56 | 4-F-phenyl | H | 3-methoxyphenyl | 374.0 |
| 57 | 4-F-phenyl | H | 3,5-dimethoxyphenyl | 417.5 |

EXAMPLES 58-65

Compounds of formula IV are shown in the following table, the methods of preparation being described hereinafter. The table also shows characterising melting point and/or mass spectrometry data. The value of m in formula IV is 2 in all of these Examples, R¹ is hydrogen and X is O. The compounds are all in free form.

| Ex. | Ar | R³ | MS [M + H] |
|---|---|---|---|
| 58 | 4-F-phenyl | 3-cyanophenyl | 390.0 |
| 59 | 4-F-phenyl | 4-F-phenyl | 383.0 |
| 60 | 4-F-phenyl | 2-ethylphenyl | 379.0 |
| 61 | 4-F-phenyl | 1-naphthyl | 415.1 |
| 62 | 4-F-phenyl | phenyl | 365.0 |
| 63 | 4-F-phenyl | 2,5-dichloro-3-methylthiophene | 440.7 |

-continued

| Ex. | Ar | R³ | MS [M + H] |
|---|---|---|---|
| 64 | 4-F-phenyl | 2-methyl-4-bromophenyl | 457.37 |
| 65 | 4-F-phenyl | 8-methylquinolin-? | 415.49 |

EXAMPLES 66 to 128

Compounds of formula III where $R^2$ is hydrogen and m is 2 are shown in the following table, the methods of preparation being described hereinafter. The table also shows characterising melting point and/or mass spectrometry data. Examples 77 and 92 are in the form of the trifluoroacetate salt, the others are in free form.

| Ex. | Ar | X | R¹ | R³ | MS [M + H] |
|---|---|---|---|---|---|
| 66 | 4-Cl-phenyl | —O— | HO- (stereo) | 1,5-dimethyl-3-cyclobutyl-pyrazol-yl | 448.4 |
| 67 | 4-Cl-phenyl | —O— | HO- (stereo) | 5-methyl-2-cyclopropyl-1,3,4-thiadiazol-yl | 438.3 |
| 68 | 4-Cl-phenyl | —O— | —H | 5-methyl-2-ethyl-1,3,4-thiadiazol-yl | 396.2 |
| 69 | 4-Cl-phenyl | —CH₂— | H₃CO- (stereo) | 1,5-dimethyl-3-cyclopropyl-pyrazol-yl | 446.34 |
| 70 | 4-Cl-phenyl | —CH₂— | H₃CO- (stereo) | 5-methyl-3-ethyl-isoxazol-yl | 421.3 |
| 71 | 4-Cl-phenyl | —CH₂— | HO- (stereo) | 5-methyl-2-ethyl-tetrazol-yl | 408.3 |

-continued
| Ex. | Ar | X | R¹ | R³ | MS [M + H] |
|---|---|---|---|---|---|
| 72 | 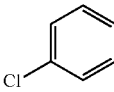 | —CH₂— |  | 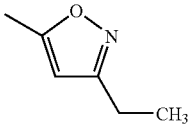 | 407.3 |
| 73 | 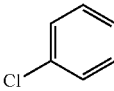 | —CH₂— |  | 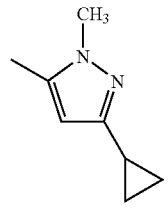 | 432.4 |
| 74 | 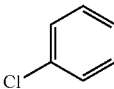 | —CH₂— |  | 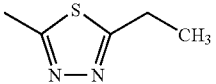 | 424.3 |
| 75 | 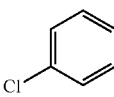 | —O— |  | 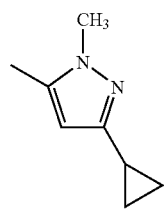 | 448.3 |
| 76 | 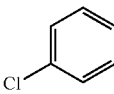 | —O— |  | 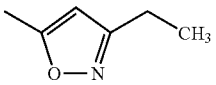 | 423.3 |
| 77 | 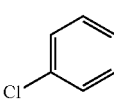 | —O— |  | 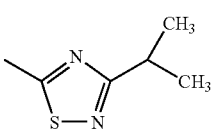 | 440.3 |
| 78 | 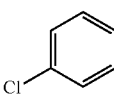 | —O— |  | 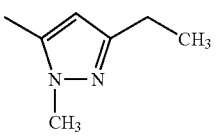 | 436.4 |
| 79 | 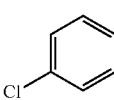 | —O— |  | 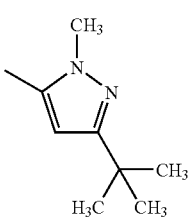 | 450.4 |
| 80 | 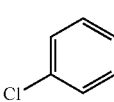 | —CH₂— |  | 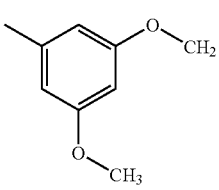 | 462.3 |

-continued

| Ex. | Ar | X | R¹ | R³ | MS [M + H] |
|---|---|---|---|---|---|
| 81 | 4-Cl-C₆H₄- | —O— | HO- (wedge) | 5-methyl-3-tert-butyl-isoxazole | 437.3 |
| 82 | 4-Cl-C₆H₄- | —O— | HO- (wedge) | 3,5-dimethyl-isoxazole | 395.2 |
| 83 | 4-Cl-C₆H₄- | —O— | HO- (wedge) | 1,5-dimethyl-3-cyclopropyl-pyrazole | 434.3 |
| 84 | 4-Cl-C₆H₄- | —O— | HO- (wedge) | 5-methyl-3-isopropyl-isoxazole | 423.3 |
| 85 | 4-Cl-C₆H₄- | —O— | HO- (wedge) | 3,5-dimethyl-1,2,4-thiadiazole | 412.3 |
| 86 | 4-Cl-C₆H₄- | —O— | HO- (wedge) | 5-methyl-2-propyl-1,3,4-thiadiazole | 440.3 |
| 87 | 4-Cl-C₆H₄- | —O— | HO- (wedge) | 5-methyl-2-methyl-tetrazole | 396.3 |
| 88 | 4-Cl-C₆H₄- | —O— | HO- (wedge) | 1-methyl-3-ethyl-5-methyl-pyrazole | 422.3 |
| 89 | 4-Cl-C₆H₄- | —O— | H₃CO- (wedge) | 5-methyl-2-ethyl-tetrazole | 424.3 |
| 90 | 4-Cl-C₆H₄- | —C(=O)— | HO- (wedge) | 5-methyl-2-ethyl-1,3,4-thiadiazole | 438.3 |

-continued

| Ex. | Ar | X | R¹ | R³ | MS [M + H] |
|---|---|---|---|---|---|
| 91 | 4-Cl-C₆H₄ | —O— | HO (stereo) | 5-methyl-2-ethyl-2H-tetrazol-yl | 410.3 |
| 92 | 4-Cl-C₆H₄ | —O— | HO (stereo) | 5-methyl-3-ethyl-isoxazol-yl | 409.3 |
| 93 | 4-Cl-C₆H₄ | —O— | HO (stereo) | 5-methyl-2-ethyl-1,3,4-thiadiazol-yl | 440.3 |
| 94 | 3,4-diCl-C₆H₃ | —O— | HO (stereo) | 5-methyl-2-ethyl-1,3,4-thiadiazol-yl | 460.2 |
| 95 | 4-Cl-C₆H₄ | —O— | HO (stereo) | 2,5-dimethyl-thiazol-yl | 411.2 |
| 96 | 4-Cl-C₆H₄ | —O— | HO (stereo) | 3-cyanophenyl | 415.3 |
| 97 | 4-Cl-C₆H₄ | —O— | HO (stereo) | 3-(N,N-dimethylcarbamoyl)phenyl | 461.2 |
| 98 | 4-Cl-C₆H₄ | —O— | HO (stereo) | 3-ethynylphenyl | 414.2 |
| 99 | 4-Cl-C₆H₄ | —O— | HO (stereo) | 5-methyl-2-ethyl-1,3,4-thiadiazol-yl | 426.2 |
| 100 | 4-Cl-C₆H₄ | —O— | HO (stereo) | 2,5-dimethyl-1,3,4-thiadiazol-yl | 412.2 |
| 101 | 4-Cl-C₆H₄ | —O— | HO (stereo) | phenyl | 390.2 |

-continued
| Ex. | Ar | X | R¹ | R³ | MS [M + H] |
|---|---|---|---|---|---|
| 102 | 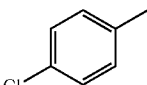 | —O— |  | 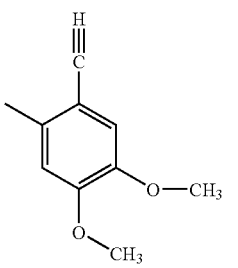 | 475.2 |
| 103 | 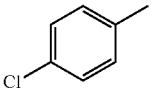 | —O— |  | 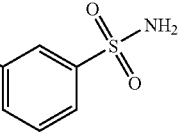 | 469.2 |
| 104 | 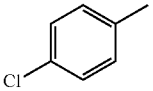 | —O— |  | 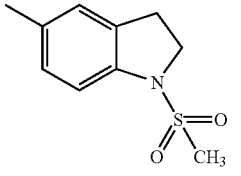 | 509.2 |
| 105 | 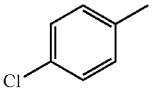 | —CH₂— |  | 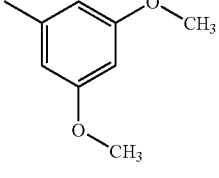 | 448.1 |
| 106 | 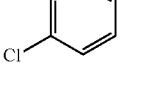 | —O— |  | 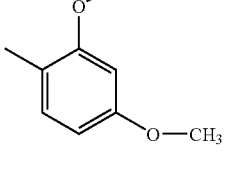 | 450.1 |
| 107 | 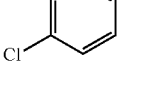 | —O— |  | 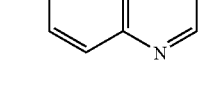 | 441.1 |
| 108 | 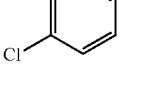 | —O— |  | 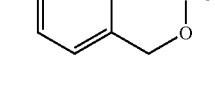 | 434.1 |
| 109 | 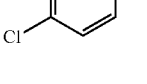 | —O— |  | 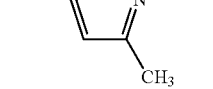 | 395.1 |
| 110 | 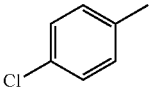 | —O— |  | 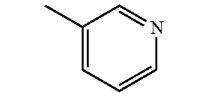 | 391.1 |

-continued
| Ex. | Ar | X | R¹ | R³ | MS [M + H] |
|---|---|---|---|---|---|
| 111 | 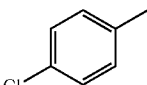 | —O— |  | 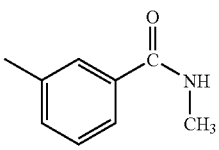 | 447.1 |
| 112 | 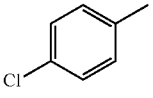 | —O— |  | 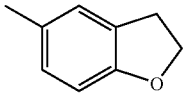 | 432.1 |
| 113 | 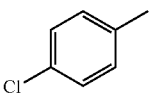 | —O— |  | 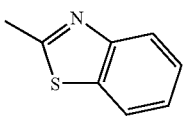 | 447.0 |
| 114 | 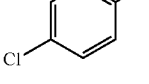 |  | 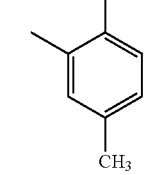 | 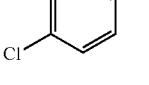 | 430.1 |
| 115 |  | —O— | 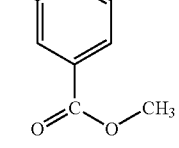 | 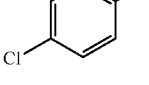 | 448.1 |
| 116 |  | —O— | 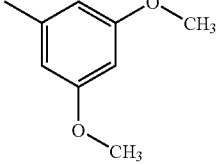 | 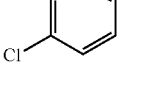 | 464.1 |
| 117 |  | —O— | 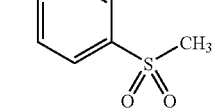 | 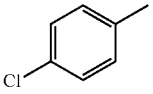 | 468.0 |
| 118 |  | —O— | 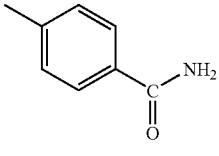 | 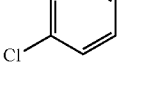 | 433.0 |
| 119 |  | —O— | 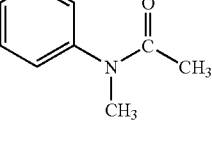 | | 461.1 |

-continued
| Ex. | Ar | X | R¹ | R³ | MS [M + H] |
|---|---|---|---|---|---|
| 120 | 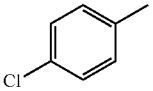 |  |  | 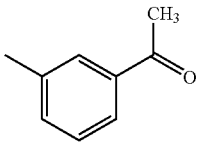 | 444.1 |
| 121 | 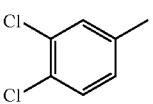 | —O— |  |  | 472.4 |
| 122 | 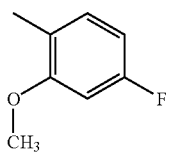 | —O— | 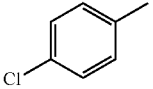 |  | 492.1 |
| 123 |  | —O— | 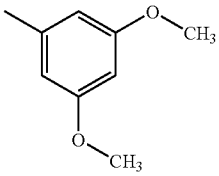 | 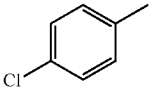 | 437.9 |
| 124 |  | —O— |  | 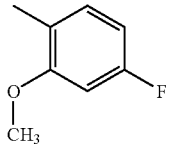 | 468.0 |
| 125 | 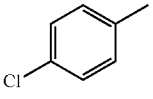 | —O— |  |  | 425.2 |
| 126 | 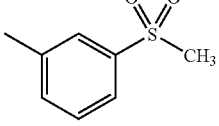 | —O— | 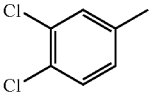 |  | 390.9 |
| 127 |  | —O— | 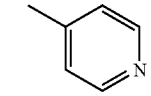 | 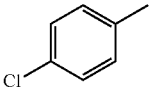 | 472.4 |
| 128 |  | —O— |  | 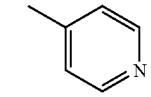 | 437.9 |

EXAMPLES 129 to 203

Compounds of Formula IIIa

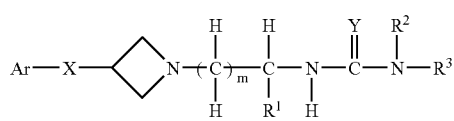

where m is 2 (except for Ex. 129 where m is 1) are shown in the following table, the methods of preparation being described hereinafter. The table also shows characterising melting point and/or mass spectrometry data. All compounds are in free form.

| Ex. | Ar | X | R¹ | Y | R² | R³ | MS [M + H] |
|---|---|---|---|---|---|---|---|
| 129 | 4-Cl-C₆H₄ | —O— | HO— | O | H | 2-methyl-5-methyl-1,3,4-thiadiazole | 412.3 |
| 130 | 4-Cl-C₆H₄ | —O— | HO— | O | —CH₃ | 3,5-dimethoxyphenyl | 463.5 |
| 131 | 4-Cl-C₆H₄ | —O— | HO— | S | H | 3-methoxyphenyl | 435.6 |
| 132 | 4-Cl-C₆H₄ | —O— | HO— | S | H | cyclohexyl | 411.5 |
| 133 | 4-Cl-C₆H₄ | —O— | HO— | S | H | 4-methoxyphenyl | 436.2 |
| 134 | 2,4-diCl-C₆H₃ | —O— | HO— | O | H | 1-methyl-3-cyclopropyl-pyrazol-5-yl | 468.2 |
| 135 | 3-F-4-Cl-C₆H₃ | —O— | HO— | O | H | 1-methyl-3-cyclopropyl-pyrazol-5-yl | — |

-continued
| Ex. | Ar | X | R¹ | Y | R² | R³ | MS [M + H] |
|---|---|---|---|---|---|---|---|
| 136 | 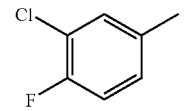 | —O— |  | O | H | 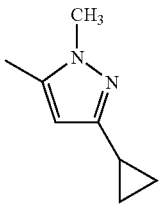 | — |
| 137 | 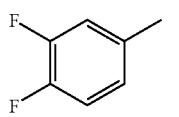 | —O— |  | O | H | 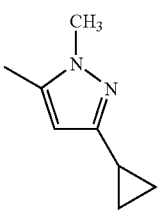 | — |
| 138 | 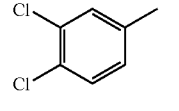 | —O— |  | O | H | 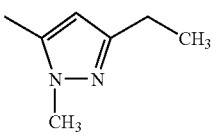 | 456.2 |
| 139 | 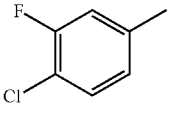 | —O— |  | O | H | 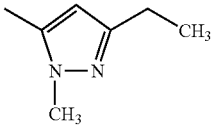 | — |
| 140 | 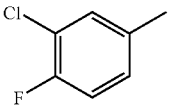 | —O— |  | O | H | 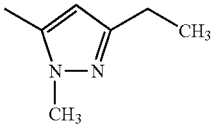 | — |
| 141 | 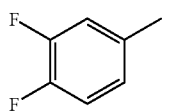 | —O— |  | O | H | 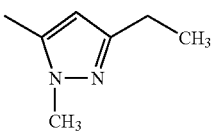 | — |
| 142 | 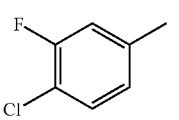 | —O— |  | O | H | 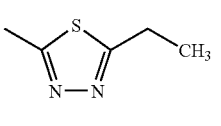 | — |
| 143 | 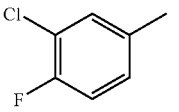 | —O— |  | O | H | 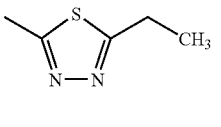 | — |
| 144 | 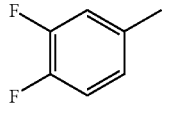 | —O— |  | O | H | 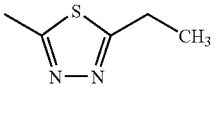 | — |

-continued

| Ex. | Ar | X | R¹ | Y | R² | R³ | MS [M + H] |
|---|---|---|---|---|---|---|---|
| 145 | 4-F-phenyl | —CH₂— | HO (wedge) | O | H | 1,5-dimethyl-3-cyclopropyl-pyrazole | — |
| 146 | 3-F,4-Cl-phenyl | —CH₂— | HO (wedge) | O | H | 1,5-dimethyl-3-cyclopropyl-pyrazole | — |
| 147 | 3-Cl,4-F-phenyl | —CH₂— | HO (wedge) | O | H | 1,5-dimethyl-3-cyclopropyl-pyrazole | — |
| 148 | 3,4-di-F-phenyl | —CH₂— | HO (wedge) | O | H | 1,5-dimethyl-3-cyclopropyl-pyrazole | — |
| 149 | 3,4-di-Cl-phenyl | —CH₂— | HO (wedge) | O | H | 1,5-dimethyl-3-cyclopropyl-pyrazole | — |
| 150 | 4-F-phenyl | —CH₂— | HO (wedge) | O | H | 1,5-dimethyl-3-ethyl-pyrazole | — |
| 151 | 3-F,4-Cl-phenyl | —CH₂— | HO (wedge) | O | H | 1,5-dimethyl-3-ethyl-pyrazole | — |
| 152 | 3-Cl,4-F-phenyl | —CH₂— | HO (wedge) | O | H | 1,5-dimethyl-3-ethyl-pyrazole | — |

-continued

| Ex. | Ar | X | R¹ | Y | R² | R³ | MS [M + H] |
|---|---|---|---|---|---|---|---|
| 153 | 3,4-difluorophenyl | —CH₂— | HO (stereo) | O | H | 5-methyl-3-ethyl-1-methyl-1H-pyrazole | — |
| 154 | 3,4-dichlorophenyl | —CH₂— | HO (stereo) | O | H | 5-methyl-3-ethyl-1-methyl-1H-pyrazole | — |
| 155 | 4-fluorophenyl | —CH₂— | HO (stereo) | O | H | 2-methyl-5-ethyl-1,3,4-thiadiazole | — |
| 156 | 3-fluoro-4-chlorophenyl | —CH₂— | HO (stereo) | O | H | 2-methyl-5-ethyl-1,3,4-thiadiazole | — |
| 157 | 3-chloro-4-fluorophenyl | —CH₂— | HO (stereo) | O | H | 2-methyl-5-ethyl-1,3,4-thiadiazole | — |
| 158 | 3,4-difluorophenyl | —CH₂— | HO (stereo) | O | H | 2-methyl-5-ethyl-1,3,4-thiadiazole | — |
| 159 | 3,4-dichlorophenyl | —CH₂— | HO (stereo) | O | H | 2-methyl-5-ethyl-1,3,4-thiadiazole | — |
| 160 | 3-fluoro-4-chlorophenyl | —C(O)— | HO (stereo) | O | H | 1,5-dimethyl-3-cyclopropyl-1H-pyrazole | — |
| 161 | 3-chloro-4-fluorophenyl | —C(O)— | HO (stereo) | O | H | 1,5-dimethyl-3-cyclopropyl-1H-pyrazole | — |
| 162 | 3,4-difluorophenyl | —C(O)— | HO (stereo) | O | H | 1,5-dimethyl-3-cyclopropyl-1H-pyrazole | — |

-continued

| Ex. | Ar | X | R¹ | Y | R² | R³ | MS [M + H] |
|---|---|---|---|---|---|---|---|
| 163 | 4-Cl-3-F-phenyl | —C(O)— | HO (stereo) | O | H | 1-methyl-3-ethyl-5-methyl-pyrazole | — |
| 164 | 3-Cl-4-F-phenyl | —C(O)— | HO (stereo) | O | H | 1-methyl-3-ethyl-5-methyl-pyrazole | — |
| 165 | 3,4-di-F-phenyl | —C(O)— | HO (stereo) | O | H | 1-methyl-3-ethyl-5-methyl-pyrazole | — |
| 166 | 4-Cl-3-F-phenyl | —C(O)— | HO (stereo) | O | H | 2-ethyl-5-methyl-1,3,4-thiadiazole | — |
| 167 | 3-Cl-4-F-phenyl | —C(O)— | HO (stereo) | O | H | 2-ethyl-5-methyl-1,3,4-thiadiazole | — |
| 168 | 3,4-di-F-phenyl | —C(O)— | HO (stereo) | O | H | 2-ethyl-5-methyl-1,3,4-thiadiazole | — |
| 169 | phenyl | —O— | HO (stereo) | O | H | 2-ethyl-5-methyl-1,3,4-thiadiazole | 392.2 |
| 170 | 3-Cl-phenyl | —O— | HO (stereo) | O | H | 2-ethyl-5-methyl-1,3,4-thiadiazole | 426.2 |
| 171 | 3-F-phenyl | —O— | HO (stereo) | O | H | 2-ethyl-5-methyl-1,3,4-thiadiazole | — |
| 172 | 4-Cl-3-CH₃-phenyl | —O— | HO (stereo) | O | H | 1,5-dimethyl-3-cyclopropyl-pyrazole | — |

-continued

| Ex. | Ar | X | R¹ | Y | R² | R³ | MS [M + H] |
|---|---|---|---|---|---|---|---|
| 173 | H₃C-, F-phenyl (3-methyl-4-fluoro) | —O— | HO (stereo) | O | H | 1,5-dimethyl-3-cyclopropyl-pyrazole | — |
| 174 | H₃C-, Cl-phenyl (3-methyl-4-chloro) | —CH₂— | HO (stereo) | O | H | 1,5-dimethyl-3-cyclopropyl-pyrazole | — |
| 175 | H₃C-, F-phenyl (3-methyl-4-fluoro) | —CH₂— | HO (stereo) | O | H | 1,5-dimethyl-3-cyclopropyl-pyrazole | — |
| 176 | H₃C-, Cl-phenyl (3-methyl-4-chloro) | —C(O)— | HO (stereo) | O | H | 1,5-dimethyl-3-cyclopropyl-pyrazole | — |
| 177 | H₃C-, F-phenyl (3-methyl-4-fluoro) | —C(O)— | HO (stereo) | O | H | 1,5-dimethyl-3-cyclopropyl-pyrazole | — |
| 178 | H₃C-, Cl-phenyl (3-methyl-4-chloro) | —O— | HO (stereo) | O | H | 1-methyl-3-ethyl-5-methyl-pyrazole | — |
| 179 | H₃C-, F-phenyl (3-methyl-4-fluoro) | —O— | HO (stereo) | O | H | 1-methyl-3-ethyl-5-methyl-pyrazole | — |
| 180 | H₃C-, Cl-phenyl (3-methyl-4-chloro) | —CH₂— | HO (stereo) | O | H | 1-methyl-3-ethyl-5-methyl-pyrazole | — |

-continued

| Ex. | Ar | X | R¹ | Y | R² | R³ | MS [M + H] |
|---|---|---|---|---|---|---|---|
| 181 | 4-F, 3-CH₃ phenyl | —CH₂— | HO (wedge) | O | H | 1,5-dimethyl-3-ethyl-pyrazol-1-yl | — |
| 182 | 4-Cl, 3-CH₃ phenyl | —C(O)— | HO (wedge) | O | H | 1,5-dimethyl-3-ethyl-pyrazol-1-yl | — |
| 183 | 4-F, 3-CH₃ phenyl | —C(O)— | HO (wedge) | O | H | 1,5-dimethyl-3-ethyl-pyrazol-1-yl | — |
| 184 | 4-Cl, 3-CH₃ phenyl | —O— | HO (wedge) | O | H | 5-methyl-2-ethyl-1,3,4-thiadiazol-2-yl | — |
| 185 | 4-F, 3-CH₃ phenyl | —O— | HO (wedge) | O | H | 5-methyl-2-ethyl-1,3,4-thiadiazol-2-yl | — |
| 186 | 4-Cl, 3-CH₃ phenyl | —CH₂— | HO (wedge) | O | H | 5-methyl-2-ethyl-1,3,4-thiadiazol-2-yl | — |
| 187 | 4-F, 3-CH₃ phenyl | —CH₂— | HO (wedge) | O | H | 5-methyl-2-ethyl-1,3,4-thiadiazol-2-yl | — |
| 188 | 4-Cl, 3-CH₃ phenyl | —C(O)— | HO (wedge) | O | H | 5-methyl-2-ethyl-1,3,4-thiadiazol-2-yl | — |
| 189 | 4-F, 3-CH₃ phenyl | —C(O)— | HO (wedge) | O | H | 5-methyl-2-ethyl-1,3,4-thiadiazol-2-yl | — |
| 190 | 4-Cl phenyl | —CH₂— | H | O | H | 5-methyl-2-ethyl-1,3,4-thiadiazol-2-yl | 394.1 |
| 191 | 4-Cl phenyl | —CH₂— | —CH₃ | O | H | 5-methyl-2-ethyl-1,3,4-thiadiazol-2-yl | 394.1 |
| 192 | 4-Cl phenyl | —O— | HO (wedge) | O | H | 3-methyl-5-ethyl-isoxazol-yl | 409.2 |

| Ex. | Ar | X | R¹ | Y | R² | R³ | MS [M + H] |
|---|---|---|---|---|---|---|---|
| 193 | 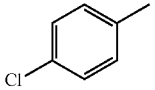 | —O— |  | O | H | 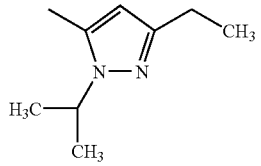 | 450.2 |
| 194 | 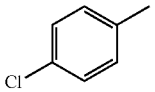 | —O— |  | O | H | 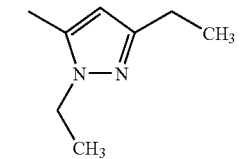 | 436.2 |
| 195 | 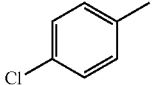 | —O— |  | O | H | 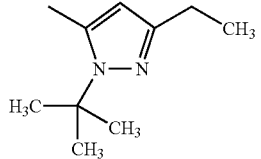 | 464.3 |
| 196 | 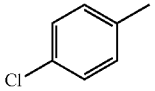 | —O— |  | O | H | 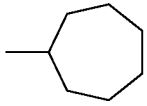 | 410.2 |
| 197 | 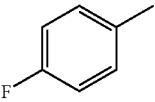 | —O— |  | O | H | 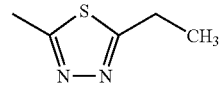 | 410.2 |
| 198 | 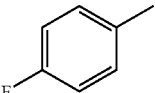 | —O— |  | O | H | 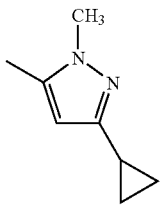 | — |
| 199 | 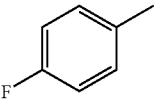 | —O— |  | O | H | 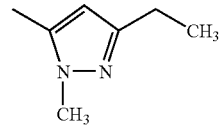 | — |
| 200 | 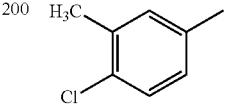 | —O— | H | O | H | 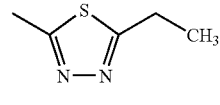 | 410.2 |
| 201 | 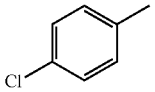 | —O— | H | O | H | 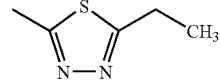 | 430.1 |
| 202 | 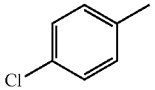 | —O— |  | O | H | 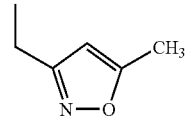 | 409.2 |

| Ex. | Ar | X | R¹ | Y | R² | R³ | MS [M + H] |
|---|---|---|---|---|---|---|---|
| 203 | 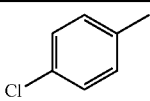 | —O— |  | O | H | 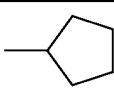 | 382.3 |

Preparation of Starting Compounds (S)-2-Amino-4-[3-(4-chloro-phenoxy)-azetidin-1-yl]-butan-1-ol A solution of {(S)-3-[3-(4-chloro-phenoxy)-azetidin-1-yl]-1-hydroxymethyl-propyl}-carbamic acid tert-butyl ester. (0.46 g, 1.24 mmol) in dichloromethane (6 ml) is treated with trifluoroacetic acid (2 ml) and the reaction mixture stirred for 1 hour at ambient temperature. The solvent is evaporated and the residue dissolved in water. The resulting aqueous solution is basified with saturated aqueous NaHCO₃ and extracted into dichloromethane. The dichloromethane is dried over MgSO₄ and evaporated to afford (S)-2-amino-4-[3-(4-chlorophenoxy)-azetidin-1-yl]-butan-1-ol as a clear oil. [MH]+ 271.0

{1-[(S)-3-Amino-4-(tert-butyl-diphenyl-silanyloxy)-butyl]-azetidin-3-yl}-(4-fluoro-phenyl)-methanone A solution of {(S)-1-(tert-butyl-diphenyl-silanyloxymethyl)-3-[3-(4-fluoro-benzoyl)-azetidin-1-yl]-propyl}-carbamic acid tert-butyl ester. (0.188 g, 0.321 mmol) in dichloromethane (5 ml) is treated with trifluoroacetic acid, and stirred at ambient temperature for 0.5 hour. The reaction mixture is diluted with dichloromethane and washed with water and saturated aqueous NaHCO₃. The organic phase is dried over MgSO₄ and evaporated to afford {1-[(S)-3-Amino-4-(tert-butyl-diphenyl-silanyloxy)-butyl]-azetidin-3-yl)-(4-fluoro-phenyl)-methanone. [MH]+ 505.2.

Azetidin-3-yl-(4-chloro-phenyl)-methanone hydrochloride

A solution of (1-Benzhydryl-azetidin-3-yl)-(4-chloro-phenyl)-methanone (19.8 g, 54.8 mmol) in dichloromethane (250 ml), cooled to −4° C., is treated with 1-chloroethyl-chloroformate (8.0 ml, 73.8 mmol) and allowed to warm to ambient temperature. The reaction mixture is stirred for 18 hours and then evaporated. The residue is dissolved in methanol (220 ml) and stirred at ambient temperature for 3.5 hours. The methanol solution is concentrated and the product precipitated by addition of diethylether. The precipitate is collected by filtration and dries under high vacuum to afford Azetidin-3-yl-(4-chloro-phenyl)-methanone hydrochloride. [MH]+ 195.95.

Other substituted benzoyl azetidine compounds are made analogously.

(1-Benzhydryl-azetidin-3-yl)-(4-chloro-phenyl)-methanone

A solution of 1-Benzhydryl-azetidine-3-carbonitrile (23.6 g, 95 mmol) in chlorobenzene (250 ml) under nitrogen is treated with a 1.0 M solution of 4-chlorophenylmagnesium bromide in diethylether (100 ml, 100 mmol) over one hour, ensuring the temperature does not exceed 30° C. The stirred reaction mixture is heated to 60° C. for 1 hour, then cooled back to ambient temperature and quenched with a saturated aqueous solution of ammonium chloride (250 ml). The organic phase is washed with brine, dried over magnesium sulphate, and evaporated to a yellow oil. The oil is dissolved in methanol (300 ml), treated with concentrated hydrochloric acid (25 ml), and stirred at ambient temperature for 18 hours. The solvent is evaporated and the residue partitioned between ethylacetate (250 ml) and saturated sodium bicarbonate solution (250 ml). The aqueous phase is extracted with more ethylacetate and the combined organic phases, treated with magnesium sulphate and charcoal, filtered and evaporated to afford (1-Benzhydryl-azetidin-3-yl)-(4-chloro-phenyl)-methanone. [MH]+ 361.99

1-Benzhydryl-3-(3,4-dichloro-phenoxy)-azetidine

A solution of 3,4 dichlorophenol (4.12 g, 25.3 mmol) in DMF (150 ml) under argon is treated with a 60% dispersion of sodium hydride in mineral oil (40.4 mmol) and the reaction mixture stirred for 10 minutes. A solution of Methanesulfonic acid 1-benzhydryl-azetidin-3-yl ester (7.27 g, 22.96 mmol) in DMF (50 ml) is added and the reaction mixture left to stir at 60° C. for 20 hours. The reaction mixture is partitioned between ethylacetate and water. The organic phase is washed with water (×2), dried over magnesium sulphate and evaporated. The crude product is purified by flash silica chromatography (elution with 1:4 ethylacetate/isohexane) to afford 1-Benzhydryl-3-(3,4-dichloro-phenoxy)-azetidine. [M+H] 383.8

N-(3-Bromo-propyl)-3-cyano-benzenesulfonamide

A suspension of bromopropylamine hydrogen bromide (0.219 g, 1 mmol) in dichloromethane (2 ml) is treated with a solution of dimethylaminopyridine (0.004 g) in dichloromethane (0.5 ml) followed by a solution of 3-cyano-benzenesulfonyl chloride (0.2 g, 1.0 mmol) in dichloromethane (0.5 ml). Triethylamine (0.3 ml, 2.16 mmol) is added and the reaction mixture stirred at ambient temperature for 2 hours, then quenched with water and saturated aqueous NaHCO₃, and extracted into dichloromethane. The organic phase is washed with aqueous 1M HCl solution and brine, dried over MgSO₄ and evaporated to afford crude N-(3-bromopropyl)-3-cyano-benzenesulfonamide. (¹³C NMR, 100 MHz, CDCl₃, 30.2, 32.6, 41.9, 114.3, 117.5, 130.7, 130.9, 131.1, 136.3, 142.1).

(S)-2-tert-Butoxycarbonylamino-4-[3-(4-chloro-phenoxy)-azetidin-1-yl]-4-oxo-butyric acid benzyl ester A solution of (S)-2-tert-butoxycarbonylamino-succinic acid 1-benzyl ester (5.0 g, 13.99 mmol) in dichloromethane (50 ml) is treated with diisopropylethylamine (7.51 ml, 41.97 mmol) and 2-(1H-benzotriazol-1-yl)-1,1,3,3-tetramethyl-uronium tetrafluoroborate (4.49 g, 13.99 mmol). To the reaction mixture is added 3-(4-chloro-phenoxy)-azetidine hydrochloride (3.06 g, 13.99 mmol) and stirring continued for 3 hours. The dichloromethane is evaporated and residue partitioned between ethylacetate and saturated NaHCO₃ solution. The ethylacetate phase is washed with 1M HCl solution and brine, dried over MgSO₄ and evaporated. The crude product is purified by flash silica chromatography (elution with 1:1 ethylacetate/hexane) to afford (S)-2-tert-butoxycarbonylamino-4-[3-(4-chloro-phenoxy)-azetidin-1-yl]4-oxo-butyric acid benzyl ester. [M-BOC] 389.0.

(S)-3-tert-Butoxycarbonylamino-4-iodo-butyric acid benzyl ester

A suspension of polymer bound triphenyl phosphine (18.25 g, 54.76 mmol) in DCM (100 ml) is treated with iodine (12.2 g, 48.1 mmol) and the reaction mixture stirred at ambient temperature for 15 minutes. Imidazole (3.72 g, 54.7 mmol) is added and the reaction mixture stirred for a further 15 minutes. A solution of (S)-3-tert-butoxycarbonylamino-4-hydroxy-butyric acid benzyl ester (6.76 g, 21.9 mmol) in DCM (100 ml) is added. The suspension is stirred at reflux for 1.5 hours, then filtered through Celite™ filter material, washing through with DCM. The combined organic phase is washed with an aqueous solution of 10% sodium thiosulphate, water and brine, then dried over magnesium sulphate and evaporated. The crude product is chromatographed over flash silica using 8% ethylacetate in iso-hexane as eluent to afford (S)-3-tert-butoxycarbonylamino-4-iodo-butyric acid benzyl ester. [M-BOC] 320.12

(S)-3-tert-Butoxycarbonylamino-4-methoxy-butyric acid benzyl ester

A solution of (S)-3-tert-butoxycarbonylamino-4-hydroxy-butyric acid benzyl ester (31.4 g, 101 mmol) (prepared using the method of Rodriguez, Marc; Linares, Muriel; Doulut, Sylvie; Heitz, Annie; Martinez, Jean; Tetrahedron Lett. (1991), 32(7), 923-6) in dichloromethane (280 ml) is cooled to −20° C. and a 48% aqueous solution of tetrafluoroboric acid (13.3 ml, 101 mmol) added. With vigorous stirring is added dropwise a 2.0 M solution of trimethylsilyl-diazomethane (50.8 ml, 101 mmol) in hexane over 35 minutes. After stirring for a further 30 minutes, a second aliquot of trimethylsilyldiazomethane is added (12.7 ml, 25 mmol) slowly over 10 minutes. After stirring for a further 30 minutes at −20° C. a further aliquot of trimethylsilyldiazomethane (12.7 ml, 25 mmol) is added over 10 minutes. This pattern is continued until a total of 127 ml of trimethylsilyldiazomethane solution (254 mmol) is added. After the last addition the reaction mixture is left to stir for 1.5 hours at −20° C. The reaction mixture is then quenched with water and extracted into dichloromethane. The organic phase is dried over magnesium sulphate and evaporated. The crude product is purified by flash silica chromatography (elution with 2:8 ethylacetate/hexane) to afford (S)-3-tert-Butoxycarbonyl-amino-4-methoxy-butyric acid benzyl ester as a clear oil. [M-BOC] 224.19.

(S)-3-tert-Butoxycarbonylamino-4-(tert-butyl-diphenyl-silanyloxy)-butyric acid benzyl ester A solution of (S)-3-tert-butoxycarbonylamino-4-hydroxy-butyric acid benzyl ester (1.34 g, 4.37 mmol) (prepared using the method of Rodriguez, Marc; Linares, Muriel; Doulut, Sylvie; Heitz, Annie; Martinez, Jean; Tetrahedron Lett. (1991), 32(7), 923-6) and imidazole (0.88 g, 13.01 mmol in dimethylformamide (7 ml) is treated with tertbutyldiphenylsilyl chloride (1.69 ml, 6.5 mmol). The reaction mixture is stirred together at room temperature for 1 hour, then diluted with water and extracted into ethylacetate. The ethylacetate phase is dried over MgSO₄ and evaporated. The crude product is purified by flash silica chromatography (elution with 1:1 ethylacetate/hexane) to afford (S)-3-tert-butoxycarbonylamino-4-(tert-butyl-diphenyl-silanyloxy)-butyric acid benzyl ester. [M-BOC] 448.0.

(S)-1-tert-Butoxymethyl-3-[3-(4-fluoro-phenoxy)-azetidin-1-yl]-propylamine

A solution of {(S)-1-tert-butoxymethyl-3-[3-(4-fluoro-phenoxy)-azetidin-1-yl]-propyl}-carbamic acid benzyl ester (0.2 g, 0.45 mmol) in methanol containing 10% palladium on carbon (66 mg) is stirred under an atmosphere of hydrogen for 3 hours, then filtered through a celite™ filter The filtrate is evaporated and the residue taken up in ethyl acetate, washed with aqueous NaHCO₃ solution and brine, dried over MgSO₄ and evaporated to afford (S)-1-tert-butoxymethyl-3-[3-(4-fluoro-phenoxy)-azetidin-1-yl]-propylamine.

{(S)-1-(tert-Butyl-diphenyl-silanyloxymethyl)-3-[3-(4-fluoro-benzoyl)-azetidin-1-yl-]-propyl}-carbamic acid tert-butyl ester A solution of 4-fluorobenzoyl-azetidine hydrochloride (0.192 g, 0.892 mmol), triethylamine (0.252 ml, 3.24 mmol) and [(S)-1-(tert-butyl-diphenyl-silanyloxymethyl)-3-iodo-propyl]-carbamic acid tert-butyl ester (0.448 g, 0.811 mmol) in dimethylformamide (3 ml) is stirred at ambient temperature for 18 hours, then partitioned between ethylacetate and water. The ethylacetate phase is dried over MgSO₄ and evaporated. The crude product is purified by flash silica chromatography (elution with a 1:99 methanol/dichloromethane) to afford {(S)-1-(tert-butyl-diphenyl-silanyloxymethyl)-3-[3-(4-fluoro-benzoyl)-azetidin-1-yl]-propyl}carbamic acid tert-butyl ester. [MH]+ 605.2.

1-{(S)-1-(tert-Butyl-diphenyl-silanyloxymethyl)-3-[3-(4-fluoro-benzoyl)-azetidin-1-yl-propyl}-3-(3,5-dimethoxy-phenyl)-urea A solution of 1-[(S)-3-amino-4-(tert-butyl-diphenyl-silanyloxy)-butyl]-azetidin-3-yl}-(4-fluorophenyl)-methanone (0.152 g, 0.301 mmol) and 3,5-dimethoxyphenylisocyanate (0.054 g, 0.301 mmol) in dichloromethane (3 ml) is stirred at ambient temperature for 18 hours. The solvent is evaporated and the crude product purified by flash silica chromatography (elution with a 2:98 methanol/dichloromethane) to afford 1-{(S)-1-(tert-butyl-diphenyl-silanyloxymethyl)-3-[3-(4-fluoro-benzoyl)-azetidin-1-yl]-propyl}-3-(3,5-dimethoxy-phenyl)-urea. [MH]+ 684.1.

[(S)-1-(tert-Butyl-diphenyl-silanyloxymethyl)-3-hydroxy-propyl]-carbamic acid tert-butyl ester A solution of (S)-3-tert-butoxycarbonylamino-4-(tert-butyl-diphenyl-silanyloxy)-butyric acid benzyl ester in (2.37 g, 4.33 mmol) in dry diethylether (25 ml) at 0° C. is treated with a 2 M solution of lithium borohydride in THF (4.33 ml). The reaction mixture is allowed to warm to ambient temperature and stirred for 3 hours under argon, then quenched by addition of water (10 ml) and 0.5 M aqueous citric acid solution (20 ml). The ether is separated, and the aqueous phase extracted with more ether. The combined ether phases are dried over MgSO$_4$ and evaporated. The crude product is purified by flash silica chromatography on a biotage column (90 g) (elution with a 1:3 ethylacetate/hexane then methanol) to afford [(S)-1-(tert-butyl-diphenyl-silanyloxymethyl)-3-hydroxy-propyl]-carbamic acid tert-butyl ester [M-BOC] 344.1.

[(S)-1-(tert-Butyl-diphenyl-silanyloxymethyl)-3-iodo-propyl]-carbamic acid tert-butyl ester A suspension of polystyrene resin-bound triphenylphosphine (2.33 g, 3 mmol/g in dry dichloromethane (25 ml) is treated with iodine (1.56 g, 6.16 mmol) and stirred for 15 minutes under argon. Imidazole (0.477 g, 7.0 mmol) is added and the reaction mixture stirred at room temperature for a further 15 minutes. The reaction mixture is then treated with a solution of [(S)-1-(tert-butyl-diphenyl-silanyloxymethyl)-3-hydroxy-propyl]carbamic acid tert-butyl ester (1.24 g, 2.8 mmol) in dichloromethane (5 ml). The reaction mixture is refluxed for 2 hours under argon, then filtered through a Celite™ filter pad, washing with dichloromethane. The filtrate is washed with 5% aqueous sodium thiosulphate solution and water, dried over MgSO$_4$ and evaporated. The crude product is purified by flash silica chromatography (elution with 1:99 methanol/dichloromethane) to afford [(S)-1-(tert-butyl-diphenyl-silanyloxymethyl)-3-iodo-propyl]-carbamic acid tert-butyl ester. [M-BOC] 453.9.

3-(4-Chloro-benzoyl)-azetidine-1-carboxylic acid tert-butyl ester

A solution of azetidin-3-yl-(4-chloro-phenyl)-methanone hydrochloride (50 g, 210 mmol) in dioxan:water 1:1 (800 ml) is added powdered sodium bicarbonate (61.7 g, 730 mmol) and the reaction mixture cooled to 10° C. Di-tbutyl-dicarbonate (52.6 g, 240 mmol) is added portion wise and the reaction mixture allowed to warm to room temperature with stirring for 1.5 hours. The reaction mixture is poured into water (1500 ml) and the resulting white precipitate filtered off and dried under vacuum to afford 3-(4-Chloro-benzoyl)-azetidine-1-carboxylic acid tert-butyl ester. $^1$H NMR 400 MHz, CDCl$_3$, δ 1.45 (9H), 4.10 (1H), 4.20 (4H), 7.47 (2H), 7.80 (2H)

3-(4-Chloro-benzyl)-azetidine-1-carboxylic acid tert-butyl ester

A solution of 3-[(4-Chloro-phenyl)-iodo-methyl]-azetidine-1-carboxylic acid tert-butyl ester (58 g, 140 mmol) in dimethylsulphoxide (450 ml) is treated with sodium borohydride with cooling. The reaction mixture was stirred at room temperature for 20 hours, then quenched by the slow addition of water (1000 ml). The aqueous mixture is extracted into ethylacetate, and the ethylacetate phase washed with saturated brine, dried over magnesium sulphate and evaporated. The crude product is purified by flash chromatography using a biotage 75 column (eluant gradient isohexane:ethylacetate 9:1 to 85:15) to afford 3-(4-Chloro-benzyl)-azetidine-1-carboxylic acid tert-butyl ester. $^1$H NMR 400 MHz, CDCl$_3$, δ 1.35 (9H), 2.70 (1H), 2.80 (2H), 3.55 (2H), 3.90 (2H), 6.97 (2H), 7.17 (2H).

{3-[3-(4-Chloro-benzyl)-azetidin-1-yl]-propyl}-carbamic acid tert-butyl ester

A solution of 3-(4-chloro-benzyl)-azetidine (1.0 g, 5.50 mmol), (3-bromo-propyl)-carbamic acid tert-butyl ester (1.31 g, 5.50 mmol) and diisopropylethylamine (1.91 ml, 11.0 mmol) in dry dimethylformamide (20 ml) is stirred at ambient temperature for 18 hours. The reaction mixture is partitioned between ethylacetate and water. The organic phase is washed with water and brine, dried over magnesium sulphate and evaporated. The crude product is purified by flash silica chromatography using 5% methanol in dichloromethane as eluent to afford {3-[3-(4-Chloro-benzyl)-azetidin-1-yl]-propyl}-carbamic acid tert-butyl ester. [M+H] 339.15

3-[3-(4-Chloro-benzyl)-azetidin-1-yl]-propylamine

A solution of {3-[3-(4-chloro-benzyl)-azetidin-1-yl]-propyl}-carbamic acid tert-butyl ester (0.48 g, 1.43 mmol) in DCM (5 ml) is treated with trifluoroacetic acid (2 ml) and the reaction mixture stirred for 1.25 hours. The solvent is evaporated and the crude product partitioned between 1 M sodium hydroxide solution and 20% isopropanol in DCM. The organic phase is evaporated to afford 3-[3-(4-chloro-benzyl)-azetidin-1-yl]-propylamine. [M+H] 239.13.

3-(4-Chloro-benzyl)-azetidinium trifluoroacetate salt

A solution of 3-(4-Chloro-benzyl)-azetidine-1-carboxylic acid tert-butyl ester (1.61 g, 5.71 mmol) in dichloromethane (20 ml) is treated with trifluoroacetic acid (20 ml) and stirred at ambient temperature for 1 hour. The reaction mixture is evaporated and then re-suspended in toluene and evaporated to dryness to afford 3-(4-Chloro-benzyl)-azetidinium trifluoroacetate salt. [MH]+ of free base 182.12.

All other substituted benzyl azetidine compounds are made analogously.

{(S)-3-[3-(4-Chloro-phenoxy)-azetidin-1-yl]-1-hydroxymethyl-propyl}-carbamic acid tert-butyl ester A solution of (S)-2-tert-butoxycarbonylamino-4-[3-(4-chloro-phenoxy)-azetidin-1-yl]4-oxo-butyric acid benzyl ester (1.0 g, 2.04 mmol) in dry THF (10 ml) is treated with a 1M solution of lithium aluminium hydride (5.1 ml) keeping the temperature between 20-30° C. using an ice-water bath. The reaction mixture is stirred at ambient temperature under argon for 2 hours, then quenched by addition of saturated aqueous Na$_2$SO$_4$ and filtered through a celite™ filter. The filtrate is partitioned between ethylacetate and saturated brine. The ethylacetate phase dried over MgSO$_4$ and evaporated. The crude product is purified by flash silica chromatography (elution with 5:95 methanol/dichloromethane) to afford {(S)-3-[3-(4-chloro-phenoxy)-azetidin-1-yl]-1-hydroxymethyl-propyl}-carbamic acid tert-butyl ester. [MH]+ 371.0.

(S)-3-[3-(4-Chloro-phenoxy)-azetidin-1-yl]-1-methoxymethyl-propyl}-carbamic acid tert-butyl ester A solution of 3-(4-Chloro-phenoxy)-azetidine hydrochloride (0.669 g, 3.04 mmol), triethylamine (1.7 ml, 12.16 mmol) and [(S)-3-Iodo-1-methoxymethyl-propyl)-carbamic acid tert-butyl ester (1.0 g, 3.04 mmol) in dimethylformamide (10 ml) is stirred at ambient temperature for 18 hours, then partitioned between ethylacetate and water. The ethylacetate phase is washed with saturated aqueous sodium bicarbonate solution and brine, dried over MgSO₄ and evaporated. The crude product is purified by flash silica chromatography (elution with a 5:95 methanol/dichloromethane) to afford {(S)-3-[3-(4-Chloro-phenoxy)-azetidin-1-yl]-1-methoxymethyl-propyl}-carbamic acid tert-butyl ester as a clear oil. [MH]+ 385.25.

(S)-3-[3-(Chloro-phenoxy)-azetidin-1-yl]-1-methoxymethyl-propylamine

A solution of {(S)-3-[3-(4-Chloro-phenoxy)-azetidin-1-yl]-1-methoxymethyl-propyl}-carbamic acid tert-butyl ester (0.87 g, 2.26 mmol) in dichloromethane (7 ml) is treated with trifluoroacetic acid (2 ml), and stirred at ambient temperature for 18 hours. The solvent is evaporated and the residue taken up in water, made alkali with 4.0 M aqueous sodium hydroxide solution and extracted into dichloromethane. The organic phase is dried over MgSO₄ and evaporated to afford (S)-3-[3-(4-Chloro-phenoxy)-azetidin-1-yl]-1-methoxymethyl-propylamine. [MH]+ 285.20

{(R)-3-[3-(4-Chloro-phenoxy)-azetidin-1-yl]-1-methyl-propyl}-carbamic acid tert-butyl ester A solution of ((R)-3-iodo-1-methyl-propyl)-carbamic acid tert-butyl ester (0.038 mg, 0.13 mmol), 3-(4-chloro-phenoxy)-azetidine hydrochloride (0.030 g, 0.13 mmol) and triethylamine (0.073 ml, 0.52 mmol) in DMF (1 ml) is stirred at room temperature for 18 hours. The reaction mixture is partitioned between ethylacetate and a saturated solution of sodium bicarbonate. The organic phase is washed with water and brine, dried over magnesium sulphate and evaporated. The crude product is purified by flash silica chromatography using 1:1 ethylacetate:hexane as eluent to afford {(R)-3-[3-(4-chloro-phenoxy)-azetidin-1-yl]-1-methyl-propyl}-carbamic acid tert-butyl ester. [M+H] 355.33

(R)-3-[3-(4-Chloro-phenoxy)-azetidin-1-yl]-1-methyl-propylamine

A solution of {(R)-3-[3-(4-chloro-phenoxy)-azetidin-1-yl]-1-methyl-propyl}-carbamic acid tert-butyl ester (0.019 mg, 0.053 mmol) in DCM (1 ml) is treated with trifluoroacetic acid (0.042 ml) and stirred at room temperature overnight. The solvent is evaporated and the residue partition between DCM and 1M sodium hydroxide solution. The aqueous phase is extracted with more DCM (×3) and the combined organic phases washed with brine, dried over magnesium sulphate and evaporated to afford (R)-3-[3-(4-chloro-phenoxy)-azetidin-1-yl]-1-methyl-propylamine. [M+H] 255.22

3-[(4-Chloro-phenyl)-hydroxy-methyl]-azetidine-1-carboxylic acid tert-butyl ester A solution of 3-(4-Chloro-benzoyl)-azetidine-1-carboxylic acid tert-butyl ester (62.5 g, 210 mmol) in ethanol (1000 ml) cooled to 10° C. is treated with sodium borohydride (9.5 g, 250 mmol). The reaction mixture is allowed to warm to room temperature and stirred for 2 hours. The reaction mixture is added to water and the precipitate collected by filtration, and dried under vacuum to afford 3-[(4-Chlorophenyl)-hydroxy-methyl]-azetidine-1-carboxylic acid tert-butyl ester. Mpt 123-125° C.

3-[(4-Chloro-phenyl)-iodo-methyl]-azetidine-1-carboxylic acid tert-butyl ester Polymer supported triphenylphosphine (125 g, 370 mmol) is suspended in tetrahydrofuran: acetonitrile 9:1 (1000 ml) and treated with Iodine (95.2 g, 370 mmol) followed by stirring for 15 minutes. Imidazole (25.5 g, 370 mmol) is added followed by a solution of 3-[(4-Chloro-phenyl)-hydroxy-methyl]-azetidine-1-carboxylic acid tert-butyl ester (44.7 g, 150 mmol) in tetrahydrofuran (150 ml) and the reaction mixture stirred at ambient temperature for 20 hours. The reaction mixture is filtered through celite™ filter material and the filtrate evaporated. The residue is taken up in chloroform and washed with sodium thiosulphate solution, water and brine. The solution is dried over magnesium sulphate and evaporated to provide 3-[(4-Chlorophenyl)-iodo-methyl]-azetidine-1-carboxylic acid tert-butyl ester. ¹H NMR 400 MHz, CDCl₃, δ 1.35 (9H), 3.21 (1H), 3.37 (1H), 3.60 (2H), 4.05 (1H), 5.12 (1H), 7.20 (4H).

(5-Cyclobutyl-2-methyl-2H-pyrazol-3-yl)-carbamic acid phenyl ester

A solution of 5-Cyclobutyl-2-methyl-2H-pyrazol-3-ylamine (0.156 g, 1.03 mmol) in dimethylformamide (3 ml) cooled to 0° C., is treated with phenylchloroformate (0.13 ml, 1.03 mmol) dropwise and left to stir at 0° C. for 1 hour. The reaction mixture is partitioned between ethylacetate and 1.0 M hydrochloric acid solution, and the organic phase washed with water, dried over magnesium sulphate and evaporated to yield (5-Cyclobutyl-2-methyl-2H-pyrazol-3-yl)-carbamic acid phenyl ester. [M+H] 272.22

(5-Ethyl-2-isopropyl-2H-pyrazol-3-yl)-carbamic acid phenyl ester, (2-tert-Butyl-5-ethyl-2H-pyrazol-3-yl)-carbamic acid phenyl ester and (2,5-Diethyl-2H-pyrazol-3-yl)-carbamic acid phenyl ester are prepared analogously using appropriate starting materials.

5-Cyclobutyl-2-methyl-2H-pyrazol-3-ylamine

This is synthesized in an analogous manner to 5-ethyl-2-methyl-2H-pyrazol-3-ylamine except using 3-cyclobutyl-3-oxopropionitrile instead of 3-oxo-pentanenitrile.

(5-Cyclopropyl-2-methyl-2H-pyrazol-3-yl)-carbamic acid phenyl ester

A solution of 5-Cyclopropyl-2-methyl-2H-pyrazol-3-ylamine (3.0 g, 22 mmol) (65 ml) and sodium bicarbonate (2 g, 24 mmol) in THF is cooled to 0° C. Phenylchloroformate (3.4 g, 22 mmol) is added dropwise over 15 minutes. The reaction mixture is allowed to warm to ambient temperature and stirred for 5 hours, then filtered and the filtrate partitioned between ethylacetate and water. The organic phase is washed with water, 5% aqueous citric acid solution and brine, dried over MgSO₄ and evaporated to afford (5-Cyclopropyl-2-methyl-2H-pyrazol-3-yl)-carbamic acid phenyl ester. [M+H] 258.17.

3-(3,4-Dichloro-phenoxy)-azetidine hydrochloride

A solution of 1-Benzhydryl-3-(3,4-dichloro-phenoxy)-azetidine (2.14 g, 6.4 mmol) in dry dichloromethane (20 ml) is treated with 1-chloroethylchloroformate (0.832 ml, 7.7 mmol) with stirring for 4 hours. The solvent is evaporated and the residue dissolved in methanol and refluxed for 18 hrs. The methanol is evaporated to a saturated solution, and then treated with diethylether. The resulting precipitate is filtered and dried under vacuum to afford 3-(3,4-Dichlorophenoxy)-azetidine hydrochloride. 1H NMR (D6 DMSO, 400 Mhz) δ 9.5 (2H, brS), 7.6 (1H, d), 7.2 (1H, s), 6.9 (1H, d), 5.1 (1H, m), 4.4 (2H, m), 3.95 (2H, m).

All other substituted phenoxy azetidine hydrochloride compounds are made analogously.

(3,5-Dimethoxy-phenyl)-methyl-carbamoyl chloride

A solution of phosgene (11.6 mmol) in toluene (6 ml) is diluted with dichloromethane (15 ml) and cooled to 0° C. To this is added a solution of (3,5-Dimethoxy-phenyl)-methylamine (1.67 g, 10 mmol) and triethylamine (1.78 ml, 14.0 mmol) in dichloromethane (5 ml) slowly over 30 minutes, and the reaction mixture allowed to warm to ambient temperature with stirring over 2 hours. After stirring at ambient temperature for a further 2 hours, the reaction mixture is partitioned between ether and 1M hydrochloric acid solution. The ether phase is washed with brine, dried over magnesium sulphate and evaporated to afford (3,5-Dimethoxy-phenyl)methyl-carbamoyl chloride as a white solid.

(2-Ethyl-[1,3]dioxolan-2-yl)-acetonitrile

A solution of 3-oxo-pentanenitrile (1.582 g, 16.49 mmol), ethylene glycol (1.026 ml, 84.59 mmol) and a catalytic amount of p-Toluene Sulphonic acid (8 mg) in Toluene (10 ml) is refluxed at 150° C. for 2 days using Dean-Stark apparatus. The reaction mixture is diluted with ethyl acetate and washed with saturated sodium bicarbonate solution. The organic phase is dried over $MgSO_4$, filtered, and the solvent evaporated to yield (2-ethyl-[1,3]dioxolan-2-yl)-acetonitrile. 1H NMR (400 MHz, CDCl3) d 4.15(2H,m), 4.05 (2H, m), 2.65 (2H, s), 1.80 (2H, q), 0.95 (3H, t)

2-(2-Ethyl[1,3]dioxolan-2-yl)-N-hydroxy-acetamidine

A solution of NaOH (1.17 g, 29.3 mmol) in water/methanol (1:1) (18 ml), cooled to 0° C. in an ice bath, is treated with hydroxylamine hydrochloride (1.58 g, 22.78 mmol), with stirring for 5 minutes. (2-Ethyl-[1,3]dioxolan-2-yl)-acetonitrile (1.42 g, 10.125 mmol) is added and the reaction mixture stirred at room temperature for 18 hours, then refluxed for a further 2 hours. The reaction mixture is cooled and partitioned between ethyl acetate and water. The organic phase is dried over $MgSO_4$, filtered, and the solvent evaporated to yield 2-(2-Ethyl [1,3]dioxolan-2-yl)-N-hydroxy-acetamidine. [M+H] 175.21

5-Ethyl-isoxazol-3-ylamine

A solution of 2-(2-ethyl[1,3]dioxolan-2-yl)-N-hydroxy-acetamidine (1.49 g 8.564 mmol) in ethanol (49 ml), acidified to pH 1 with concentrated hydrochloric acid solution, is refluxed at 50° C. for 3 days. The solvent is evaporated and the crude product dissolved in water and extracted into ethyl acetate (×2). The organic phase is dried over $MgSO_4$ and evaporated to afford 5-ethyl-isoxazol-3-ylamine. [M+H] 113.02

(5-Ethyl-2-methyl-2H-pyrazol-3-yl)-carbamic acid phenyl ester

A solution of 5-Ethyl-2-methyl-2H-pyrazol-3-ylamine (10 g, 79.8 mmol) (500 ml) and potassium carbonate in THF (12.14 g, 87.8 mmol) is cooled to 0° C. Phenylchloroformate (10.15 ml, 80.6 mmol) is added dropwise over 20 minutes. The reaction mixture is stirred for 40 minutes at 0° C. then allowed to warm to ambient temperature and stirred for a further 2.5 hours. The reaction mixture is partitioned between ethylacetate and water. The organic phase is washed with 5% aqueous citric acid solution and brine. The organic phase is treated with $MgSO_4$ and charcoal then filtered and evaporated to afford (5-Cyclopropyl-2-methyl-2H-pyrazol-3-yl)-carbamic acid phenyl ester. [M+H] 246.21

5-Ethyl-2-methyl-2H-pyrazol-3-ylamine

A solution of 3-Oxo-pentanenitrile (0.5 g, 5.15 mmol) and methylhydrazine (0.24 g, 5.15 mmol) in ethanol (5 ml) is heated to reflux for 1.5 hours. The solvent is evaporated and the residue partitioned between ethylacetate and brine. The organic phase is dried over $MgSO_4$ and evaporated to afford 5-Ethyl-2-methyl-2H-pyrazol-3-ylamine.

(2-Ethyl-2H-tetrazol-5-yl)-carbamic acid phenyl ester

A solution of 2-ethyl-2H-tetrazol-5-ylamine (0.1 g, 0.88 mmol) in dry THF (2 ml) is treated with pyridine (0.09 ml, 1.10 mmol) followed by a solution of phenylchloroformate (0.11 ml, 0.911 mmol) in THF (1 ml). The reaction mixture is stirred at ambient temperature for 1.5 hours, then partitioned between ethylacetate and water. The ethylacetate phase is dried over magnesium sulphate and evaporated to afford (2-Ethyl-2H-tetrazol-5-yl)-carbamic acid phenyl ester as a white solid. 1H NMR (CDCl3, 400 MHz) δ, 7.90 (1H, brs), 7.30 (2H, m), 7.15, (3H, m), 4.60 (2H, q) 1.60 (3H, t).

(3-Ethynyl-phenyl)-carbamic acid phenyl ester, (3-dimethylcarbamoyl-phenyl)-carbamic acid phenyl ester, (3-methylcarbamoyl-phenyl)-carbamic acid phenyl ester, benzothiazol-2-yl-carbamic acid phenyl ester, (4-methanesulfonyl-phenyl)-carbamic acid phenyl ester, (5-propyl-[1,3,4]thiadiazol-2-yl)carbamic acid phenyl ester, (2-ethyl-2H-tetrazol-5-yl)-carbamic acid phenyl ester, (3-sulfamoyl-phenyl)-carbamic acid phenyl ester, (1-methanesulfonyl-2,3-dihydro-1H-indol-5-yl)-carbamic acid phenyl ester, quinolin-6-yl-carbamic acid phenyl ester, (5-cyclopropyl-[1,3,4]thiadiazol-2-yl)-carbamic acid phenyl ester, (2,4-dimethoxy-phenyl)carbamic acid phenyl ester, (4-methoxymethyl-phenyl)-carbamic acid phenyl ester, (4-carbamoylphenyl)-carbamic acid phenyl ester, [4-(acetyl-methyl-amino)-phenyl]carbamic acid phenyl ester, (3-isopropyl-[1,2,4]thiadiazol-5-yl)-carbamic acid phenyl ester, (3-tert-butyl-isoxazol-5-yl)carbamic acid phenyl ester, (5-methyl-isoxazol-3-yl)-carbamic acid phenyl ester, (3-methyl-[1,2,4]thiadiazol-5-yl)-carbamic acid phenyl ester, (2-cyano-4,5-dimethoxy-phenyl)-carbamic acid phenyl ester, (4-fluoro-2-methoxy-phenyl)-carbamic acid phenyl ester and (2-Fluoro-4-methoxy-phenyl)-carbamic acid phenyl ester are all made analogously using appropriate starting materials.

(5-Ethyl-[1,3,4]thiadiazol-2-yl)-carbamic acid phenyl ester

A solution of 5-Ethyl-[1,3,4]thiadiazol-2-ylamine (2.5 g, 19.4 mmol) and pyridine (1.72 ml, 21.3 mmol) in dichloromethane (70 ml) is cooled to −70° C. and treated with a solution of phenylchloroformate (2.45 ml, 19.6 mmol) in dichloromethane (10 ml) dropwise. The reaction mixture is allowed to warm to ambient temperature and stirred for 3 hours during which a precipitate forms. The precipitate is collected by filtration, and dried under vacuum to afford (5-Ethyl-[1,3,4]thiadiazol-2-yl)-carbamic acid phenyl ester as white solid. [M+H] 250.15

{3-[3-(4-fluoro-phenoxy)-azetidin-1-yl]-propyl}-carbamic acid phenyl ester

A solution of 3-[3-(4-fluoro-phenoxy)-azetidin-1-yl]-propylamine (0.05 g, 0.223 mmol), phenylchloroformate (0.056 ml, 0.446 mmol) and dimethylaminopyridine (0.027 g, 0.223 mmol) in dichloromethane (4 ml) is stirred at ambient temperature for 24 hours. The reaction mixture is evaporated and the crude product purified by flash silica chromatography (elution 5:95 methanol/dichloromethane) to afford 3-[3-(4-Fluoro-phenoxy)-azetidin-1-yl]-propyl)-carbamic acid phenyl ester. [MH]+ 344.9.

{3-[3-(4-Fluoro-phenoxy)-azetidin-1-yl]-propyl}-carbamic acid tert-butyl ester A solution of 3-(4-fluoro-phenoxy)-azetidine hydrochloride (2.0 g, 9.85 mmol) and diisopropylethylamine (4.28 ml, 24 mmol) and (3-bromo-propyl)-carbamic acid tert-butyl ester (2.84 g, 12 mmol) in acetonitrile (20 ml) is stirred at ambient temperature for 3 days. The reaction mixture is partitioned between dichloromethane and water, the organic phase dried over $MgSO_4$ and evaporated. The crude product is purified by flash silica chromatography (elution with a 5:95 methanol/dichloromethane) to afford 3-[3-(4-fluoro-phenoxy)-azetidin-1-yl]-propyl)-carbamic acid tert-butyl ester [MH]+ 325.1.

3-[3-(4-Fluoro-phenoxy)-azetidin-1-yl]-propylamine

A solution of 3-[3-(4-fluoro-phenoxy)-azetidin-1-yl]-propyl}-carbamic acid tert-butyl ester (2.4 g, 7.4 mmol) in dichloromethane (10 ml) is treated with 4M HCl in dioxane (5.7 ml), with stirring at ambient temperature. The solvent is evaporated and the residue partitioned between dichloromethane and 4M NaOH solution. The dichloromethane phase is dried over $MgSO_4$ and evaporated to afford 3-[3-(4-fluoro-phenoxy)-azetidin-1-yl]-propylamine. [MH]+ 225.0.

((S)-3-Hydroxy-1-methoxymethyl-propyl)-carbamic acid tert-butyl ester

A solution of (S)-3-tert-Butoxycarbonylamino-4-methoxy-butyric acid benzyl ester (10.4 g, 32.3 mmol) in dry diethylether (70 ml) cooled to 0° C. is treated slowly with a 2.0 M solution of $LiBH_4$ in THF (32.2 ml, 64.4 mmol). The reaction mixture is allowed to warm to ambient temperature and then left to stir. After 6 hours the reaction mixture is quenched slowly with 0.5 M aqueous solution of citric acid and extracted with ether. The ether phase is dried over magnesium sulphate and evaporated. The crude product is purified by flash silica chromatography (elution with a gradient 3:7 to 6:4 ethylacetate/hexane) to afford ((S)-3-Hydroxy-1-methoxymethyl-propyl)-carbamic acid tert-butyl ester as a clear oil. [M-BOC] 120.13

((R)-3-Hydroxy-1-methyl-propyl)-carbamic acid tert-butyl ester

A solution of (S)-3-tert-butoxycarbonylamino-4-iodo-butyric acid benzyl ester (0.2 g, 0.477 mmol) in dry diethyl-ether (3 ml) cooled to 0° C. under argon, is treated with a 2.0 M solution of lithium borohydride in THF (0.95 ml, 1.9 mmol). The reaction mixture is allowed to warm to ambient temperature with stirring for 18 hours. The reaction is quenched by addition of water and partitioned between ethylacetate and 10% citric acid solution. The organic phase is washed with brine, dried over magnesium sulphate and evaporated. The crude product is purified by flash silica chromatography using 1% methanol in DCM as eluent to afford ((R)-3-hydroxy-1-methyl-propyl)-carbamic acid tert-butyl ester.

((S)-3-Iodo-1-methoxymethyl-propyl)-carbamic acid tert-butyl ester

A suspension of polystyrene resin-bound triphenylphosphine (18.645 g, 3 mmol/g) in dry dichloromethane (250 ml) is treated with iodine (12.5 g, 49.22 mmol) and stirred for 15 minutes under argon. Imidazole (3.87 g, 55.94 mmol) is added and the reaction mixture stirred at room temperature for a further 15 minutes. The reaction mixture is then treated with a solution of ((S)-3-Hydroxy-1-methoxymethyl-propyl)-carbamic acid tert-butyl ester (4.9 g, 22.37 mmol) in dichloromethane (30 ml), and refluxed for 1.5 hours under argon. The resin is removed by filtration through a celite pad, washing with dichloromethane. The filtrate is washed with 5% aqueous sodium thiosulphate solution and water, dried over $MgSO_4$ and evaporated to afford ((S)-3-Iodo-1-methoxymethyl-propyl)-carbamic acid tert-butyl ester as a crude oil. [M-BOC] 230.06.

((R)-3-Iodo-1-methyl-propyl)-carbamic acid tert-butyl ester

A suspension of polymer bound triphenyl phosphine (0.200 g, 0.595 mmol) in DCM (2 ml) is treated with iodine (0.133 g, 0.523 mmol) and the reaction mixture stirred at ambient temperature for 15 minutes. Imidazole (39 mg, 0.57 mmol) is added and the reaction mixture stirred for a further 15 minutes. A solution of ((R)-3-Hydroxy-1-methyl-propyl)-carbamic acid tert-butyl ester (0.045 g, 0.238 mmol) in DCM (2 ml) is added. The suspension is stirred at reflux for 2.5 hours, then filtered through Celite™ filter material, washing through with DCM.

The combined organic phase is washed with an aqueous solution of 10% sodium thiosulphate, water and brine, then dried over magnesium sulphate and evaporated to afford ((R)-3-iodo-1-methyl-propyl)-carbamic acid tert-butyl ester. [M+H] 285.05

Pyridin-4-yl-carbamic acid phenyl ester

A solution of 4 aminopyridine (0.6 g, 6.37 mmol) in dichloromethane (15 ml) is treated with triethylamine (0.89 ml, 6.37 mmol) followed by phenylchloroformate (0.80 ml, 6.37 mmol) and then stirred at room temperature for 3 days. The reaction mixture is partitioned between dichloromethane and aqueous sodium bicarbonate. The organic phase is dried over magnesium sulphate and evaporated to afford pyridin-4-yl-carbamic acid phenyl ester.

(5-Methyl-[1,3,4]thiadiazol-2-yl)-carbamic acid phenyl ester, (2-methyl-thiazol-5-yl)-carbamic acid phenyl ester, (3-methyl-isoxazol-5-yl)-carbamic acid phenyl ester, pyridin-3-yl-carbamic acid phenyl ester and (3-isopropyl-isoxazol-5-yl)-carbamic acid phenyl ester are all made analogously using appropriate starting materials.

Quinoline-3-carboxylic acid (3-bromo-propyl)-amide

A suspension of quinoline-3-carboxylic acid (0.1 g, 0.57 mmol) in dichloromethane (1.5 ml) is treated with dimethylformamide (0.02 ml) and then oxalylchloride (0.1 ml, 1.15 mmol). The reaction mixture is stirred under argon at ambient temperature for 1.6 hours, then evaporated to afford quinoline-3-carbonyl chloride as a crude pale yellow solid. The crude material is suspended in dichloromethane (2.0 ml) and treated with bromopropylamine hydrobromide (0.125 g, 0.57 mmol) and triethylamine (0.42 ml, 3 mmol). The reaction mixture is stirred at ambient temperature for 3.25 hours, then quenched with water and partitioned between aqueous NaHCO$_3$ solution and dichloromethane. The organic phase is washed with NaHCO$_3$ solution and brine, dried over MgSO$_4$ and evaporated. The crude product is purified by flash silica chromatography (elution ethyl acetate) to afford quinoline-3-carboxylic acid (3-bromopropyl)-amide. [MH]+ 292.9.

Preparation of Final Compounds

N-{(S)-1-tert-Butoxymethyl-3-[3-(4-fluoro-phenoxy)-azetidin-1-yl]-propyl}-3,4,5-trimethoxy-benzamide—Example 1

A solution of 3,4,5-trimethoxy-benzoic acid (0.246 g, 1.16 mmol) and diisopropylethylamine (0.62 ml, 3.47 mmol) in dry dimethylformamide (10 ml) is treated with [(benzotriazol-1-yloxy)-dimethylamino methylene]-dimethyl-ammonium; tetrafluoro borate (0.32 g, 1.0 mmol). The reaction mixture is stirred at ambient temperature for 5 minutes, then (S)-1-tert-butoxymethyl-3-[3-(4-fluoro-phenoxy)-azetidin-1-yl]-propylamine (0.968 mmol) is added and the reaction mixture stirred for 20 hours. The dimethylformamide is evaporated and the residue partitioned between ethylacetate and saturated aqueous NaHCO$_3$. The ethylacetate phase is washed with brine, dried over MgSO$_4$ and evaporated. The crude product is purified by flash silica chromatography (elution 50% ethylacetate/hexane to 100% ethylacetate) to afford N-{(S)-1-tert-butoxymethyl-3-[3-(4-fluoro-phenoxy)-azetidin-1-yl]-propyl}-3,4,5-trimethoxy-benzamide [MH]+ 505.3.

N-{(S)-3-[3-(4-Fluoro-phenoxy)-azetidin-1-yl]-1-hydroxymethyl-propyl}-3,4,5-trimethoxy-benzamide—Example 2

A solution of N-{(S)-1-tert-butoxymethyl-3-[3-(4-fluoro-phenoxy)-azetidin-1-yl]-propyl}-3,4,5-trimethoxy-benzamide (Example 1, 0.066 g, 0.130 mmol) in dichloromethane (2 ml) is treated with trifluoroacetic acid (0.11 ml, 0.65 mmol) and the reaction mixture stirred for 20 hours. The solvent is evaporated and the residue partitioned between ethylacetate and saturated aqueous NaHCO$_3$. The ethylacetate phase is washed with brine, dried over magnesium sulphate and evaporated. The crude product is purified by flash silica chromatography (elution 100% ethylacetate then 5:95 methanol/dichloromethane) to afford N-{(S)-3-[3-(4-fluorophenoxy)-azetidin-1-yl]-1-hydroxymethyl-propyl}-3,4,5-trimethoxy-benzamide [MH]+ 449.1.

Example 3 is prepared in analogously.

The compounds of Examples 14, 15, 17 and 18 are prepared analogously except the hydroxy chain is not protected and for Examples 17 and 18 the resulting ester is cleaved with treatment with alkali, e.g. sodium hydroxide solution.

Quinoline-3-carboxylic acid {3-[3-(4-fluoro-phenoxy)-azetidin-1-yl]-propyl}-amide—Example 5

This is prepared analogously to Example 10 below, using quinoline-3-carboxylic acid (3-bromo-propyl)-amide in place of 2-(3-acetyl-phenoxy)-N-(3-bromopropyl)-acetamide.

2-(3-Acetyl-phenoxy)-N-[3-[3-(4-fluoro-phenoxy)-azetidin-1-yl]-propyl]-acetamide—Example 10

A solution of (3-acetyl-phenoxy)-acetic acid (0.194 g, 1.0 mmol) and diisopropylethylamine (0.38 g, 3 mmol) in dry DMF (3 ml) is treated with [dimethylamino-([1,2,3]triazolo[4,5-b]pyridin-3-yloxy)-methylene]-dimethyl-ammonium hexafluoro phosphate (0.38 g, 1.0 mmol). After stirring for 5 minutes 3-bromo-propylamine hydrobromide (0.26 g, 1.2 mmol) is added and stirring continued for a further 40 minutes. The solvent is evaporated and the crude mixture partitioned between ethylacetate and saturated aqueous NaHCO$_3$. The ethyl acetate phase is dried over MgSO$_4$ and evaporated to afford 2-(3-acetyl-phenoxy)-N-(3-bromopropyl)-acetamide. This crude material is taken up in acetonitrile (3 ml) and treated with triethylamine (0.38 g, 3 mmol) and 3-(4-fluoro-phenoxy)-azetidine hydrochloride (0.11 g, 1.2 mmol). The reaction mixture is stirred at ambient temperature for 20 hours, the solvent evaporated and the crude product purified by flash silica chromatography (elution 10:90 methanol/dichloromethane) to afford 2-(3-acetyl-phenoxy)-N-{3-[3-(4-fluoro-phenoxy)-azetidin-1-yl]-propyl}-acetamide. [MH]+ 401.14.

Examples 4, 6 to 13, 16 and 19 are prepared analogously.

1-3,4-Difluoro-phenyl)-3-{3-[3-(4-fluoro-phenoxy)-azetidin-1-yl]-propyl}-urea—Example 23

A solution of 3-[3-(4-fluoro-phenoxy)-azetidin-1-yl]-propylamine (0.04 g, 0.178 mmol) and 3,4-difluorophenylisocyanate (0.020 ml, 0.178 mmol) in dichloromethane (1 ml) is stirred at room temperature for 5 hours. The solvent is evaporated and the crude product purified by flash silica chromatography (elution gradient a 3:97 to 5:95 methanol/dichloromethane) to afford 1-(3,4-difluoro-phenyl)-3-{3-[3-(4-fluoro-phenoxy)-azetidin-1-yl]-propyl}-urea. [MH]+ 379.9.

Example 22 is prepared analogously.

1-{(S)-3-[3-(4-Chloro-phenoxy)-azetidin-1-yl]-1-hydroxymethyl-propyl}-3-(3,5-dimethoxy-phenyl)-urea—Example 26

A solution of (S)-2-amino-4-[3-(4-chloro-phenoxy)-azetidin-1-yl]-butan-1-ol (0.2 g, 0.74 mmol) in dichloromethane (6 ml) is treated with 3,5-dimethoxy-phenyl-isocyanate (0.12 g, 0.667 mmol). The reaction mixture is stirred at ambient temperature for 24 hours and then evaporated. The crude product is purified by flash silica chromatography (elution gradient 3:97 to 7:93 methanol/dichloromethane) to afford 1-{(S)-3-[3-(4-chloro-phenoxy)-azetidin-1-yl]-1-hydroxymethyl-propyl}-3-(3,5-dimethoxy-phenyl)-urea. [MH]+ 449.9.

Examples 21, 24, 25, 27 to 33, 36, 38 to 42, 44 to 48, 50 to 53, 57, 96, 101, 105, 112, 196 and 203 are prepared analogously. Example 43 is made analogously except the benzyl group is deprotected.

1-(3,5-Dimethoxy-phenyl)-3-{(S)-3-[3-(4-fluoro-benzoyl)-azetidin-1-yl]-1-hydroxymethyl-propyl}-urea—Example 34

A solution of 1-{(S)-1-(tert-butyl-diphenyl-silanyloxymethyl)-3-[3-(4-fluoro-benzoyl)-azetidin-1-yl]-propyl}-3-(3,5-dimethoxy-phenyl)-urea (0.862 g, 0.126 mmol) in THF (3 ml) is treated with a 1 M solution of tetrabutyl ammonium fluoride (TBAF, 0.126 ml), and the reaction mixture stirred at ambient temperature for 2 hours. The reaction mixture is partitioned between ethylacetate and saturated $NaHCO_3$ solution. The ethylacetate phase is washed with water and brine, dried over $MgSO_4$ and evaporated. The crude product is purified by flash silica chromatography (elution with a 5:95 methanol/dichloromethane) to afford 1-(3,5-dimethoxy-phenyl)-3-{(S)-3-[3-(4-fluoro-benzoyl)-azetidin-1-yl]-1-hydroxymethyl-propyl}-urea.

Examples 35, 37, 49, 90, 114 and 120 are prepared analogously.

1-Cyclohexyl-3-{3-[3-(4-fluoro-phenoxy)-azetidin-1-yl]-propyl}-1-methyl-urea—Example 54

A solution of 3-[3-(4-fluoro-phenoxy)-azetidin-1-yl]-propyl)-carbamic acid phenyl ester (0.035 g, 0.101 mmol) and N-methylcyclohexylamine (0.02 ml, 0.15 mmol) in dimethylsulphoxide (1 ml) is stirred at ambient temperature for 2 days. The reaction mixture is partitioned between ethylacetate and water, the organic phase dried over $MgSO_4$ and evaporated. The crude product is purified by flash silica chromatography (elution 5:95 methanol/dichloromethane) to afford 1-cyclohexyl-3-{3-[3-(4-fluoro-phenoxy)-azetidin-1-yl]-propyl)-1-methyl-urea.

3,4-Dihydro-2H-quinoline-1-carboxylic acid {3-[3-(4-fluorophenoxy)-azetidin-1-yl]-propyl}-amide—Example 55

A solution of 1-Bromo-3-isocyanato-propane (0.164 g, 1.0 mmol) in acetonitrile is stirred with 1,2,3,4-Tetrahydroquinoline (0.133 g, 1.0 mmol) and diisopropylethylamine (0.2 ml, 1.2 mmol). The reaction mixture is stirred for 2 hours at ambient temperature and then the solvent removed. The crude product is taken-up in acetonitrile (4 ml) and diisopropylethylamine (0.2 ml, 1.2 mmol) and 3-(4-Fluoro-phenoxy)-azetidine hydrochloride (0.11 g, 1.0 mmol) added. The reaction mixture is stirred at ambient temperature for 18 hours, the solvent evaporated and the crude partitioned between ethylacetate and saturated sodium bicarbonate solution. The organic phase is washed with brine, dried over magnesium sulphate and evaporated. The crude product is purified by flash silica chromatography (elution gradient ethylacetate then 5:95 methanol/dichloromethane) to afford 3,4-Dihydro-2H-quinoline-1-carboxylic acid {3-[3-(4-fluoro-phenoxy)-azetidin-1-yl]-propyl}-amide. [MH]+ 444.2

1-{3-[3-(4-Fluoro-phenoxy)-azetidin-1-yl]-propyl}-3-(3-methoxy-phenyl)-urea—Example 56

A solution of 3-[3-(4-fluoro-phenoxy)-azetidin-1-yl]-propylamine (0.07 g, 0.31 mmol) and 1-isocyanato-3-methoxybenzene (0.041 g, 0.31 mmol) in dioxane (15 ml) is heated to 100° C. for 3 hours. The reaction mixture is evaporated and the crude product purified by flash silica chromatography (elution with a 1:9 methanol/dichloromethane) to afford 1-{3-[3-(4-fluoro-phenoxy)-azetidin-1-yl]-propyl}-3-(3methoxy-phenyl)-urea. [MH]+ 374.0.

Examples 20 is are prepared analogously.

3-Cyano-N-{3-[3-(4-fluoro-phenoxy)-azetidin-4-yl]-propyl}-benzenesulfonamide—Example 58

A suspension of 3-(4-fluoro-phenoxy)-azetidine hydrochloride (0.049 g, 0.24 mmol) in acetonitrile (1.0 ml) is treated with the crude N-(3-bromo-propyl)-3-cyano-benzenesulfonamide (0.072 g) in acetonitrile (1.0 ml) and triethylamine (0.1 ml, 0.72 mmol). The resulting homogenous reaction mixture is stirred at ambient temperature for 70 hours, the solvent evaporated and the residue partitioned between ethylacetate and aqueous $NaHCO_3$ solution. The ethylacetate phase is washed with brine, dried over $MgSO_4$ and evaporated. The crude product is purified by flash silica chromatography (elution ethylacetate) to afford 3-cyano-N-{3-[3-(4-fluoro-phenoxy)-azetidin-1-yl]-propyl}-benzenesulfonamide. [MH]+ 390.

Examples 59 to 65 are prepared analogously.

1-{(S)-3-[3-(4-Chloro-phenoxy)-azetidin-1-yl]-1-methoxyethyl-propyl}-3-(5-ethyl-2-methyl-2H-pyrazol-3-yl)-urea—Example 78

A solution of (S)-3-[3-(4-Chloro-phenoxy)-azetidin-1-yl]-1-methoxymethyl-propylamine (1.6 g, 5.6 mmol) and (5-Ethyl-2-methyl-2H-pyrazol-3-yl)-carbamic acid phenyl ester (1.65 g, 6.7 mmol, see preparation below) in DMSO (7 ml) is stirred at ambient temperature for 4 hours, then partitioned between water and ethylacetate. The organic phase is washed again with water, dried over MgSO4 and evaporated. The crude product is purified by flash silica chromatography (elution with a 5:95 methanol/dichloromethane) to afford 1-{(S)-3-[3-(4-Chloro-phenoxy)-azetidin-1-yl]-1-methoxymethyl-propyl}-3-(5-ethyl-2-methyl-2H-pyrazol-3-yl)-urea. [M+H] 436.37.

Examples 69, 70, 75, 76, 80, 89, 93 and 116 are prepared analogously

1-{(S)-3-[3-(4-Chloro-phenoxy)-azetidin-1-yl]-1-hydroxymethyl-propyl}-3-(5-cyclopropyl-2-methyl-2H-pyrazol-3-yl)-urea—Example 83

A solution of (S)-2-amino-4-[3-(4-chloro-phenoxy)-azetidin-1-yl]-butan-1-ol (0.158 g, 0.58 mmol) and (5-Cyclopropyl-2-methyl-2H-pyrazol-3-yl)-carbamic acid phenyl ester (0.150 g, 0.58 mmol) in DMSO (3 ml) is stirred at ambient temperature for 6 hours, then partitioned between water and ethylacetate. The organic phase is washed again with water, dried over $MgSO_4$ and evaporated. The crude product is purified by flash silica chromatography (elution with a 10:90 methanol/dichloromethane) to afford 1-{(S)-3-[3-(4-Chloro-phenoxy)-azetidin-1-yl]-1-hydroxymethyl-propyl}-3-(5-cyclopropyl-2-methyl-2H-pyrazol-3-yl)-urea. [M+H] 434.33.

The compounds of Examples 66, 67, 71 to 74, 77, 79, 81 to 88, 91, 92, 94, 95, 97, 98, 100, 102, 103, 104, 106 to 111, 113, 115, 117 to 119, 121 and 123 to 128 are prepared analogously using an appropriate carbamic acid phenyl ester.

1-{(S)-3-[3-(4-Chloro-phenoxy)-azetidin-1-yl]-1-hydroxymethyl-propyl}-3-(5-ethyl-2-methyl-2H-pyrazol-3-yl)-urea—Example 88

A solution of (S)-2-amino-4-[3-(4-chloro-phenoxy)-azetidin-1-yl]-butan-1-ol (0.45 g, 2 mmol) and (5-Ethyl-2-methyl-2H-pyrazol-3-yl)-carbamic acid phenyl ester (0.49 g, 1.66 mmol) in DMSO (5 ml) is stirred at ambient temperature for 1 hour, then partitioned between water and ethylacetate. The organic phase is dried over $MgSO_4$ and evaporated. The crude product is purified by recrystallisation from hot ethylacetate to afford 1-{(S)-3-[3-(4-Chloro-phenoxy)-azetidin-1-yl]-1-hydroxymethyl-propyl}-3-(5-ethyl-2-methyl-2H-pyrazol-3-yl)-urea.

1-{(S)-3-[3-(4-Chloro-phenoxy)-azetidin-1-yl]-1-hydroxymethyl-propyl}-3-(5-ethyl-[1,3,4]thiadiazol-2-yl)-urea—Example 99

A solution of (S)-2-amino-4-[3-(4-chloro-phenoxy)-azetidin-1-yl]-butan-1-ol hydrochloride (1.04 g, 2.82 mmol), (5-Ethyl-[1,3,4]thiadiazol-2-yl)-carbamic acid phenyl ester (0.70 g, 2.82 mmol) and triethylamine (1.6 ml, 11.28 mmol) in DMSO (70 ml) is stirred at ambient temperature for 18 hour, then partitioned between ethylacetate and saturated aqueous sodium bicarbonate solution. The organic phase is washed with brine, dried over $MgSO_4$ and evaporated. The crude product is purified by recrystallisation from hot ethylacetate to afford 1-{(S)-3-[3-(4-Chloro-phenoxy)-azetidin-1-yl]-1-hydroxymethyl-propyl}-3-(5-ethyl-[1,3,4]-thiadiazol-2-yl)-urea. [M+H] 426.18.

The compound of Example 129 is prepared analogously using (S)-2-amino-4-[3-(4-chlorophenoxy)-azetidin-1-yl]-propan-1-ol instead of (S)-2-amino-4-[3-(4-chloro-phenoxy)-azetidin-1-yl]-butan-1-ol. Where (S)-2-Amino-4-[3-(4-chloro-phenoxy)-azetidin-1-yl]-propan-1-ol is prepared analogously to (S)-2-amino-4-[3-(4-chloro-phenoxy)-azetidin-1-yl]-butan-1-ol except using NBOC-D serine instead of (S)-2-tert-butoxycarbonylamino-succinic acid.

Acetic acid (S)-4-[3-(4-chloro-phenoxy)-azetidin-1-yl]-2-[3-(3,5-dimethoxy-phenyl)-ureido]-butyl ester—Example 122

A solution of 1-{(S)-3-[3-(4-chloro-phenoxy)-azetidin-1-yl]-1-hydroxymethyl-propyl}-3-(3,5-dimethoxy-phenyl)-urea (0.05 g, 0.111 mmol) and triethylamine (0.031 ml, 0.222 mmol) in DCM (3 ml) is treated with acetic anhydride and left to stir at room temperature for 3 hours. The reaction mixture is partitioned between DCM and water. The organic phase is washed with sodium bicarbonate solution, dried over magnesium sulphate and evaporated to afford acetic acid (S)-4-[3-(4-chloro-phenoxy)-azetidin-1-yl]-2-[3-(3,5-dimethoxy-phenyl)-ureido]-butyl ester. [M+H] 492.08

3-{(S)-3-[3-(4-Chloro-phenoxy)-azetidin-1-yl]-1-hydroxmethyl-propyl}-1-(3,5-dimethoxy-phenyl)-1-methyl-urea—Example 130

1-{(S)-1-(tert-Butyl-diphenyl-silanyloxymethyl)-3-[3-(4-chloro-phenoxy)-azetidin-1-yl]-propyl}-3-(3,5-dimethoxy-phenyl)-1-methyl-urea A solution of (S)-1-(tert-Butyl-diphenyl-silanyloxymethyl)-3-[3-(4-chloro-phenoxy)-azetidin-1-yl]-propylamine (0.1 g, 0.196 mmol), (3,5-Dimethoxy-phenyl)-methyl-carbamoyl Chloride (45 mg, 0.19 mmol) and triethylamine (0.027 ml, 0.19 mmol) in dichloromethane (2 ml) is stirred at room temperature for 2 days. The reaction mixture is washed with water, dried over magnesium sulphate and evaporated. The crude product is chromatographed over flash silica using ethyl acetate as eluent to afford 1-{(S)-1-(tert-Butyl-diphenyl-silanyloxymethyl)-3-[3-(4-chloro-phenoxy)-azetidin-1-yl]-propyl}-3-(3,5-dimethoxy-phenyl)-]-methyl-urea. [M+H] 702.3

3-{(S)-3-[3-(4-Chloro-phenoxy)-azetidin-1-yl]-1-hydroxyethyl-propyl}-1-(3,5-dimethoxy-phenyl)-1-methyl-urea 1-{(S)-1-(tert-Butyl-diphenyl-silanyloxymethyl)-3-[3-(4-chloro-phenoxy)-azetidin-1-yl]-propyl}-3-(3,5-dimethoxy-phenyl)-1-methyl-urea is deprotected in the same manner as 1-(3,5-Dimethoxy-phenyl)-3-{(S)-3-[3-(4-fluoro-benzoyl)-azetidin-1-yl]-1-hydroxymethyl-propyl}-urea in Example 34 to afford 3-{(S)-3-[3-(4-Chloro-phenoxy)-azetidin-1-yl]-1-hydroxymethyl-propyl}-1-(3,5-dimethoxy-phenyl)-1-methyl-urea. [M+H] 463.5

1-{(S)-3-[3-(4-Chloro-phenoxy)-azetidin-1-yl]-1-hydroxymethyl-propyl}-3-(3-methoxy-phenyl)-thio-urea—Example 131

This compound is prepared in a manner analogous to that used to prepare 1-{(S)-3-[3-(4-Chloro-phenoxy)-azetidin-1-yl]-1-hydroxymethyl-propyl}-3-(3,5-dimethoxy-phenyl)-urea in Example 26 except in the final step the isocyanate is replaced with the appropriate isothiocyanate.

The compounds of Examples 132 and 133 are prepared analogously.

1-{(S)-3-[3-(3,4-dichloro-phenoxy)-azetidin-1-yl]-1-hydroxyethyl-propyl}-3-(5-cycle-propyl-2-methyl-2H-pyrazol-3-yl)-urea—Example 134

This compound is prepared analogously to 1-{(S)-3-[3-(4-chloro-phenoxy)-azetidin-1-yl]-1-hydroxymethyl-propyl}-3-(5-cyclopropyl-2-methyl-2H-pyrazol-3-yl)-urea in Example 83 except using (S)-2-amino-4-[3-(3,4-dichloro-phenoxy)-azetidin-1-yl]-butan-1-ol in place of (S)-2-amino-4-[3-(4-chloro-phenoxy)-azetidin-1-yl]-butan-1-ol.

The compounds of Examples 135 to 137 are prepared analogously using the appropriate halo-substituted phenoxy-azetidine compound.

1-{(S)-3-[3-(3,4-dichloro-phenoxy)-azetidin-1-yl]-1-hydroxymethyl-propyl}-3-(5-ethyl-2-methyl-2H-pyrazol-3-yl)-urea—Example 138

This compound is prepared in a manner analogous to that used to prepare 1-{(S)-3-[3-(4-chloro-phenoxy)-azetidin-1-yl]-1-hydroxymethyl-propyl}-3-(5-ethyl-2-methyl-2H-pyrazol-3-yl)-urea in Example 88 except using (S)-2-amino-4-[3-(3,4-dichloro-phenoxy)-azetidin-1-yl]-butan-1-ol hydrochloride in place of (S)-2-amino-4-[3-(4-chloro-phenoxy)-azetidin-1-yl]-butan-1-ol hydrochloride.

The compounds of Examples 139 to 141 are prepared analogously using the appropriate halo-substituted phenoxy-azetidine compound.

1-{(S)-3-[3-(4-chloro-3-fluoro-phenoxy)-azetidin-1-yl]-1-hydroxymethyl-propyl}-3-(5-ethyl-[1,3,4]thiadiazol-2-yl)-urea—Example 142

This compound is prepared analogously to 1-{(S)-3-[3-(4-chloro-phenoxy)-azetidin-1-yl]-1-hydroxymethyl-propyl}-3-(5-ethyl-[1,3,4-thiadiazol-2-yl)-urea in Example 99 except using (S)-2-amino-4-[3-(4-chloro-3-fluoro-phenoxy)-azetidin-1-yl]-butan-1-ol hydrochloride in place of (S)-2-amino-4-[3-(4-chloro-phenoxy)-azetidin-1-yl]-butan-1-ol hydrochloride.

The compounds of Examples 143 and 144 are prepared analogously using the appropriate halo-substituted phenoxy-azetidine compound.

1-{(S)-3-[3-(4-fluoro-benzyl)-azetidin-1-yl]-1-hydroxymethyl-propyl}-3-(5-cyclo-propyl-2-methyl-2H-pyrazol-3-yl)-urea—Example 145

This compound is prepared in a manner analogous to that used to prepare 1-{(S)-3-[3-(4-Chloro-phenoxy)-azetidin-1-yl]-1-hydroxymethyl-propyl}-3-(5-cyclopropyl-2-methyl-2H-pyrazol-3-yl)-urea in Example 83 except using (S)-2-amino-4-[3-(4-fluoro-benzyl)-azetidin-1-yl]-butan-1-ol in place of (S)-2-amino-4-[3-(4-chloro-phenoxy)-azetidin-1-yl]-butan-1-ol.

The compounds of Examples 146 to 149 are prepared analogously using the appropriate halo-substituted benzyl-azetidine compound.

1-{(S)-3-[3-(4-fluoro-benzyl)-azetidin-1-yl]-1-hydroxymethyl-propyl}-3-(5-ethyl-2-methyl-2H-pyrazol-3-yl)-urea—Example 150

This compound is prepared analogously to 1-{(S)-3-[3-(4-Chloro-phenoxy)-azetidin-1-yl]-1-hydroxymethyl-propyl}-3-(5-ethyl-2-methyl-2H-pyrazol-3-yl)-urea in Example 88 except using (S)-2-amino-4-[3-(4-fluoro-benzyl)-azetidin-1-yl]-butan-1-ol hydrochloride in place of (S)-2-amino-4-[3-(4-chloro-phenoxy)-azetidin-1-yl]-butan-1-ol hydrochloride.

The compounds of Examples 151 to 154 are prepared analogously using the appropriate halo-substituted benzyl-azetidine compound.

1-{(S)-3-[3-(4-fluoro-benzyl)-azetidin-1-yl]-1-hydroxymethyl-propyl}-3-(5-ethyl-[1,3,4]thiadiazol-2-yl)-urea—Example 155

This compound is prepared analogously to 1-{(S)-3-[3-(4-chloro-phenoxy)-azetidin-1-yl]-1-hydroxymethyl-propyl}-3-(5-ethyl-[1,3,4]-thiadiazol-2-yl)-urea in Example 99 except using (S)-2-amino-4-[3-(4-fluoro-benzyl)-azetidin-1-yl]-butan-1-ol hydrochloride in place of (S)-2-amino-4-[3-(4-chloro-phenoxy)-azetidin-1-yl]-butan-1-ol hydrochloride.

The compounds of Examples 156 to 159 are prepared analogously using the appropriate halo-substituted benzyl-azetidine compound.

1-{(S)-3-[3-(4-chloro-3-fluoro-benzol)-azetidin-1-yl]-1-hydroxymethyl-propyl}-3-(5-cyclo-propyl-2-methyl-2H-pyrazol-3-yl)-urea—Example 160

This compound is prepared analogously to 1-{(S)-3-[3-(4-Chloro-phenoxy)-azetidin-1-yl]-1-hydroxymethyl-propyl}-3-(5-cyclopropyl-2-methyl-2H-pyrazol-3-yl)-urea in Example 83 except using (S)-2-amino-4-[3-(4-chloro-3-fluoro-benzyl)-azetidin-1-yl]-butan-1-ol in place of (S)-2-amino-4-[3-(4-chloro-phenoxy)-azetidin-1-yl]-butan-1-ol.

The compounds of Examples 161 and 162 are prepared analogously using the appropriate halo-substituted benzoyl-azetidine compound.

1-{(S)-3-[3-(4-chloro-3-fluoro-benzoyl)-azetidin-1-yl]-1-hydroxymethyl-propyl}-3-(5-ethyl-2-methyl-2H-pyrazol-3-yl)-urea—Example 163

This compound is prepared analogously to 1-{(S)-3-[3-(4-Chloro-phenoxy)-azetidin-1-yl]-1-hydroxymethyl-propyl}-3-(5-ethyl-2-methyl-2H-pyrazol-3-yl)-urea in Example 88 except using (S)-2-amino-4-[3-(4-chloro-3-fluoro-benzoyl)-azetidin-1-yl]-butan-1-ol hydrochloride in place of (S)-2-amino-4-[3-(4-chloro-phenoxy)-azetidin-1-yl]-butan-1-ol hydrochloride.

The compounds of Examples 164 and 165 are prepared analogously using the appropriate halo-substituted benzoyl-azetidine compound.

1-{(S)-3-[3-(4-chloro-3-fluoro-benzoyl)-azetidin-1-yl]-1-hydroxymethyl-propyl}-3-(5-ethyl-[1,3,4]thiadiazol-2-yl)-urea—Example 166

This compound is prepared analogously to 1-{(S)-3-[3-(4-chloro-phenoxy)-azetidin-1-yl]-1-hydroxymethyl-propyl}-3-(5-ethyl-[1,3,4]-thiadiazol-2-yl)-urea in Example 99 except using (S)-2-amino-4-[3-(4-chloro-3-fluoro-benzoyl)-azetidin-1-yl]-butan-1-ol hydrochloride in place of (S)-2-amino-4-[3-(4-chloro-phenoxy)-azetidin-1-yl]-butan-1-ol hydrochloride.

The compounds of Examples 167 and 168 are prepared analogously using the appropriate halo-substituted benzoyl-azetidine compound.

1-{(S)-3-[3-phenoxy-azetidin-1-yl]-1-hydroxymethyl-propyl}-3-(5-ethyl-[1,3,4]thiadiazol-2-yl)-urea—Example 169

This compound is prepared analogously to 1-{(S)-3-[3-(4-chloro-phenoxy)-azetidin-1-yl]-1-hydroxymethyl-propyl}-3-(5-ethyl-[1,3,4]-thiadiazol-2-yl)-urea in Example 99 except using (S)-2-amino-4-[3-phenoxy-azetidin-1-yl]-butan-1-ol hydrochloride in place of (S)-2-amino-4-[3-(4-chloro-phenoxy)-azetidin-1-yl]-butan-1-ol hydrochloride.

1-{(S)-3-[3-(3-chloro-phenoxy)-azetidin-1-yl]-1-hydroxymethyl-propyl}-3-(5-ethyl-[1,3,4]thiadiazol-2-yl)-urea—Example 170

This compound is prepared analogously to 1-{(S)-3-[3-(4-chloro-phenoxy)-azetidin-1-yl]-1-hydroxymethyl-propyl}-3-(5-ethyl-[1,3,4]-thiadiazol-2-yl)-urea in Example 99 except using (S)-2-amino-4-[3-(3-chloro-phenoxy)-azetidin-1-yl]-butan-1-ol hydrochloride in place of (S)-2-amino-4-[3-(4-chloro-phenoxy)-azetidin-1-yl]-butan-1-ol hydrochloride.

The compound of Example 171 is prepared analogously using (S)-2-amino-4-[3-(3-fluoro-phenoxy)-azetidin-1-yl]-butan-1-ol hydrochloride in place of (S)-2-amino-4-[3-(4-chloro-phenoxy)-azetidin-1-yl]-butan-1-ol hydrochloride.

1-{(S)-3-[3-(4 chloro-3-methyl-phenoxy)-azetidin-1-yl]-1-hydroxymethyl-propyl}-3-(5-cyclo-propyl-2-methyl-2H-pyrazol-3-yl)-urea—Example 172

This compound is prepared analogously to 1-{(S)-3-[3-(4-Chloro-phenoxy)-azetidin-1-yl]-1-hydroxymethyl-propyl}-3-(5-cyclopropyl-2-methyl-2H-pyrazol-3-yl)-urea in Example 83 except using (S)-2-amino-4-[3-(4-chloro-3-methyl-phenoxy)-azetidin-1-yl]-butan-1-ol in place of (S)-2-amino-4-[3-(4-chloro-phenoxy)-azetidin-1-yl]-butan-1-ol.

The compounds of Examples 173 to 177 are prepared analogously using the appropriate methyl and halo-substituted phenoxy/benzyl/benzoyl-azetidine compound.

1-{(S)-3-[3-(4-chloro-3-methyl-phenoxy)-azetidin-1-yl]-1-hydroxymethyl-propyl}-3-(5-ethyl-2-methyl-2H-pyrazol-3-yl)-urea—Example 178

This compound is prepared analogously to 1-{(S)-3-[3-(4-chloro-phenoxy)-azetidin-1-yl]-1-hydroxymethyl-propyl}-3-(5-ethyl-2-methyl-2H-pyrazol-3-yl)-urea in Example 88 except using (S)-2-amino-4-[3-(4-chloro-3-methyl-phenoxy)-azetidin-1-yl]-butan-1-ol hydrochloride in place of (S)-2-amino-4-[3-(4-chloro-phenoxy)-azetidin-1-yl]-butan-1-ol hydrochloride.

The compounds of Examples 179 and 183 are prepared analogously using the appropriate methyl and halo-substituted phenoxy/benzyl/benzoyl-azetidine compound.

1-{(S)-3-[3-(4-chloro-3-methyl-phenoxy)-azetidin-1-yl]-1-hydroxymethyl-propyl}-3-(5-ethyl-[1,3,4]thiadiazol-2-yl]-urea—Example 184

This compound is prepared analogously to 1-{(S)-3-[3-(4-chloro-phenoxy)-azetidin-1-yl]-1-hydroxymethyl-propyl}-3-(5-ethyl-[1,3,4]-thiadiazol-2-yl)-urea in Example 99 except using (S)-2-amino-4-[3-(4-chloro-3-methyl-phenoxy)-azetidin-1-yl]-butan-1-ol hydrochloride in place of (S)-2-amino-4-[3-(4-chloro-phenoxy)-azetidin-1-yl]-butan-1-ol hydrochloride.

The compounds of Examples 185 to 189 are prepared analogously using the appropriate methyl and halo-substituted phenoxy/benzyl/benzoyl-azetidine compound.

1-{(S)-3-[3-(4-chloro-benzyl)-azetidin-yl]-propyl}-3-(5-ethyl-[1,3,4]thiadiazol-yl)-urea—Example 190

A solution of 3-[3-(4 chloro-benzyl)-azetidin-1-yl]-propylamine (0.100 mg, 0.418 mmol) and (5-ethyl-[1,3,4]thiadiazol-2-yl)-carbamic acid phenyl ester (0.11 mg, 0.439 mmol) in DMSO is stirred at room temperature for 18 hours then partitioned between ethylacetate and water. The organic phase is washed with brine and dried over magnesium sulphate and evaporated. The crude product is purified by flash silica chromatography using 5% methanol in DCM as eluent to afford 1-{3-[3-(4-chloro-benzyl)-azetidin-1-yl]-propyl}-3-(5-ethyl-[1,3,4]thiadiazol-2-yl)-urea. [M+H] 394.1

1-{(R)-3-[3-(4-Chloro-phenoxy)-azetidin-1-yl]-1-methyl-propyl}-3-(5-ethyl-[1,3,4]thiadiazol-2-yl)-urea—Example 191

A solution of (R)-3-[3-(4-chloro-phenoxy)-azetidin-1-yl]-1-methyl-propylamine (0.145 mg, 0.569 mmol) and (5-ethyl-[1,3,4]thiadiazol-2-yl)-carbamic acid phenyl ester (0.142 mg, 0.569 mmol) in DMSO is stirred at room temperature for 4 hours then partitioned between ethylacetate and water. The organic phase is washed with brine and dried over magnesium sulphate and evaporated. The crude product is recrystallised from hot ethylacetate to afford 1-{(R)-3-[3-(4-Chloro-phenoxy)-azetidin-1-yl]-1-methyl-propyl}-3-(5-ethyl-[1,3,4]thiadiazol-2-yl)-urea. [M+H] 410.14.

1-{(S)-3-[3-(4-Chloro-phenoxy)-azetidin-1-yl]-1-hydroxymethyl-propyl}-3-(5-ethyl-isoxazol-3-yl)-urea—Example 192

This compound is prepared analogously to Example 88 but using (5-ethyl-isoxazol-3-yl)-carbamic acid phenyl ester in place of (5-ethyl-2-methyl-2H-pyrazol-3-yl))-carbamic acid phenyl ester.

The compounds of Examples 193 to 195 are prepared analogously using the appropriate carbamic acid phenyl ester. In each case the relevant heterocycle is made in a manner analogous to that used to prepare 5-ethyl-2-methyl-2H-pyrazol-3-ylamine except methyl hydrazine is replaced with the appropriate alkyl-hydrazine.

1-{(S)-3-[3-(4-Chloro-phenoxy)-azetidin-1-yl]-1-hydroxmethyl-propyl}-3-cycloheptyl-urea—Example 196

This compound is prepared analogously to Example 26.

1-{(S)-3-[3-(4-fluoro-phenoxy)-azetidin-1-yl]-1-hydroxymethyl-propyl}-3-(5-ethyl-[1,3,4]thiadiazol-2-yl)-urea—Example 197

This compound is prepared analogously to 1-{(S)-3-[3-(4-chloro-phenoxy)-azetidin-1-yl]-1-hydroxymethyl-propyl}-3-(5-ethyl-[1,3,4]-thiadiazol-2-yl)-urea in Example 99 except using (S)-2-amino-4-[3-(4-fluoro-phenoxy)-azetidin-1-yl]-butan-1-ol hydrochloride in place of (S)-2-amino-4-[3-(4-chloro-phenoxy)-azetidin-1-yl]-butan-1-ol hydrochloride.

1-{(S)-3-[3-(4-fluoro-phenoxy)-azetidin-1-yl]-1-hydroxymethyl-propyl}-3-(5-cyclo-propyl-2-methyl-2H-pyrazol-3-yl)-urea—Example 198

This compound is prepared analogously to 1-{(S)-3-[3-(4-chloro-phenoxy)-azetidin-1-yl]-1-hydroxymethyl-propyl}-3-(5-cyclopropyl-2-methyl-2H-pyrazol-3-yl)-urea in Example 83 except using (S)-2-amino-4-[3-(4-fluoro-phenoxy)-azetidin-1-yl]-butan-1-ol in place of (S)-2-amino-4-[3-(4-chloro-phenoxy)-azetidin-1-yl]-butan-1-ol.

1-{(S)-3-[3-(4-fluoro-phenoxy)-azetidin-1-yl]-1-hydroxymethyl-propyl}-3-(5-ethyl-2-methyl-2H-pyrazol-3-yl)-urea—Example 199

This compound is prepared analogously to 1-{(S)-3-[3-(4-chloro-phenoxy)-azetidin-1-yl]-1-hydroxymethyl-propyl}-3-(5-ethyl-2-methyl-2H-pyrazol-3-yl)-urea in Example 88 except using (S)-2-amino-4-[3-(4-fluoro-phenoxy)-azetidin-1-yl]-butan-1-ol hydrochloride in place of (S)-2-amino-4-[3-(4-chloro-phenoxy)-azetidin-1-yl]-butan-1-ol hydrochloride.

1-{(S)-3-[3-(4-chloro-3-methyl-phenoxy)-azetidin-1-yl-propyl}-3-(5-ethyl-(1,3,4]thiadiazol-2-yl)-urea—Example 200

The compound of this Example is made in a manner analogous to that used to prepare 1-{(S)-3-[3-(4-chloro-benzyl)-azetidin-1-yl]-propyl}-3-(5-ethyl-[1,3,4]thiadiazol-2-yl)-urea in Example 192 but using 3-[3-(4-chloro-3-methyl-phenoxy)-azetidin-1-yl]-propylamine in place of 3-[3-(4-chloro-benzyl)-azetidin-1-yl]-propylamine. [M+H] 410.2

1-{(S)-3-[3-(3,4-dichloro-phenoxy)-azetidin-1-yl]-propyl}-3-(5-ethyl-[1,3,4]thiadiazol-2-yl)-urea—Example 201

This compound is prepared analogously to {(S)-3-[3-(4-chloro-benzyl)-azetidin-1-yl]-propyl}-3-(5-ethyl-[1,3,4]thiadiazol-2-yl)-urea in Example 192 but using 3-[3-(3,4-dichloro-phenoxy)-azetidin-1-yl]-propylamine in place of 3-[3-(4-chloro-benzyl)-azetidin-1-yl]-propylamine. [M+H] 430.1

1-{(S)-3-[3-(4-Chloro-phenoxy)-azetidin-1-yl]-1-hydroxymethyl-propyl}-3-(5-methyl-isoxazol-3-yl-methyl)-urea—Example 202

This compound is prepared analogously to Example 88 but using (5-methyl-isoxazol-3-yl-methyl)-carbamic acid phenyl ester in place of (5-ethyl-2-methyl-2H-pyrazol-3-yl))-carbamic acid phenyl ester.

1-{(S)-3-[3-(4-Chloro-phenoxy)-azetidin-1-yl]-1-hydroxymethyl-propyl}-3-cyclopentyl-urea—Example 203

This compound is prepared analogously to Example 26.

The invention claimed is:

1. A compound of formula I

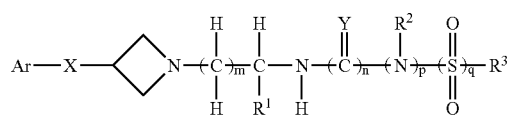

in free or salt form, where
Ar is phenyl optionally substituted by one or more substituents selected from halogen, $C_1$-$C_8$-alkyl, cyano or nitro;
$R^1$ is hydrogen or $C_1$-$C_8$-alkyl optionally substituted by hydroxy, $C_1$-$C_8$-alkoxy, acyloxy, halogen, carboxy, $C_1$-$C_8$-alkoxycarbonyl, —N($R^4$)$R^5$, —CON($R^6$)$R^7$ or by a monovalent cyclic organic group having 3 to 15 atoms in the ring system;
$R^2$ is hydrogen, $C_1$-$C_8$-alkyl or $C_3$-$C_{10}$-cycloalkyl;
$R^3$ is a heterocyclic group having 5 to 11 ring atoms of which 1 to 4 are hetero atoms selected from nitrogen, oxygen and sulphur atoms;
$R^4$ and $R^5$ are each independently hydrogen or $C_1$-$C_8$-alkyl, or $R^4$ is hydrogen and $R^5$ is hydroxy-$C_1$-$C_8$-alkyl, acyl, —SO$_2$$R^8$ or —CON($R^6$)$R^7$, or $R^4$ and $R^5$ together with the nitrogen atom to which they are attached denote a 5-or 6-membered heterocyclic group;

$R^6$ and $R^7$ are each independently hydrogen or $C_1$-$C_8$-alkyl, or $R^6$ and $R^7$ together with the nitrogen atom to which they are attached denote a 5- or 6-membered heterocyclic group;
$R^8$ is $C_1$-$C_8$-alkyl, $C_1$-$C_8$-haloalkyl, or phenyl optionally substituted by $C_1$-$C_8$-alkyl;
X is —C(=O)—, —O—, —CH$_2$—, or CH(OH);
Y is oxygen or sulfur;
m is 1, 2, 3 or 4; and
n, p and q are each 0 or 1, n+p+q=1 or 2, n+q=1, p+q=1, and when n is 0, p is 0.

2. A compound according to claim 1, in which
Ar is phenyl substituted by one or two substituents selected from halogen and $C_1$-$C_8$-alkyl;
$R^1$ is hydrogen, $C_1$-$C_4$-alkyl optionally substituted by hydroxy or $C_1$-$C_8$-alkoxy, acyloxy, $C_1$-$C_8$-alkyl substituted by benzoyloxy or phenoxy-$C_1$-$C_4$-alkylcarbonyloxy which are optionally substituted in the benzene ring by at least one substituent selected from $C_1$-$C_8$-alkoxy, $C_1$-$C_8$-alkylcarbonyl and aminosulfonyl, or $C_1$-$C_8$-alkyl substituted by naphthyl;
$R^2$ is hydrogen or $C_1$-$C_8$-alkyl,
$R^3$ is a heterocyclic group having 5 to 11 ring atoms of which 1 to 4 are hetero atoms selected from nitrogen, oxygen and sulphur atoms;
X is —O—, —C(=O)— or —CH$_2$—;
Y is oxygen or sulfur; and
m is 1, 2, 3 or 4.

3. A compound according to claim 1, in which
Ar is phenyl substituted by one or two substituents selected from halogen and $C_1$-$C_4$-alkyl;
$R^1$ is hydrogen, $C_1$-$C_4$-alkyl optionally substituted by hydroxy or $C_1$-$C_4$-alkoxy, acyloxy, $C_1$-$C_4$-alkyl substituted by benzoyloxy or phenoxy-$C_1$-$C_4$-alkylcarbonyloxy which are optionally substituted in the benzene ring by at least one substituent selected from $C_1$-$C_4$-alkoxy, $C_1$-$C_4$-alkylcarbonyl and aminosulfonyl, or $C_1$-$C_4$-alkyl substituted by naphthyl;
$R^2$ is hydrogen or $C_1$-$C_4$-alkyl,
$R^3$ is a heterocyclic group having 5 to 11 ring atoms of which 1 to 4 are hetero atoms selected from nitrogen, oxygen and sulphur atoms;
X is —O—, —C(=O)— or —CH$_2$—;
Y is oxygen or sulfur; and
m is 1, 2, 3 or 4.

4. A compound according to claim 1, which is of formula II

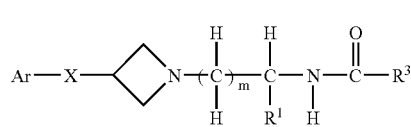

where
Ar is phenyl substituted by one or two substituents selected from fluorine and chlorine, one of said substituents being para to the indicated group X,
$R^1$ is hydrogen, $C_1$-$C_4$-alkyl substituted by hydroxy or $C_1$-$C_4$-alkoxy, $C_1$-$C_4$-alkyl substituted by benzoyloxy or phenoxy-$C_1$-$C_4$-alkylcarbonyloxy which are optionally substituted in the benzene ring by at least one substituent selected from $C_1$-$C_4$-alkoxy, $C_1$-$C_4$-alkylcarbonyl and aminosulfonyl, or $C_1$-$C_4$-alkyl substituted by naphthyl, R³ is a heterocyclic group having 5 to 11 ring atoms of which 1 to 4 are hetero atoms selected from nitrogen, oxygen and sulphur atoms;

X is —O—, and m is 2 or 3.

5. A compound according to claim 1, which is of formula III

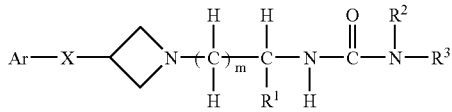

where

Ar is phenyl substituted by one or two substituents selected from fluorine and chlorine, one of said substituents being para to the indicated group X, R¹ is hydrogen, $C_1$-$C_4$-alkyl substituted by hydroxy or $C_1$-$C_4$-alkoxy, R² is hydrogen or $C_1$-$C_4$-alkyl R³ is a heterocyclic group having 5 to 11 ring atoms of which 1 to 4 are hetero atoms selected from nitrogen, oxygen and sulphur atoms;

X is —O— or —C(=O)—, and m is 2 or 3.

6. A compound according to claim 1, which is also of formula III,

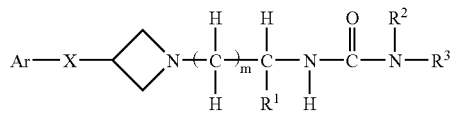

where

Ar is phenyl substituted by chlorine para to the indicated group X and optionally also substituted by chlorine meta to the indicated group X, R¹ is hydrogen or $C_1$-$C_4$-alkyl substituted by hydroxy, $C_1$-$C_4$-alkoxy or $C_1$-$C_4$-acyloxy, R² is hydrogen, R³ is a heterocyclic group having 5 to 11 ring atoms of which 1 to 4 are hetero atoms selected from nitrogen, oxygen and sulphur atoms X is —O—, —CH₂— or —C(=O)—, and m is 2.

7. A compound according to claim 1, which is also of formula IIIa

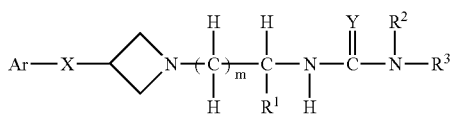

where

Ar is phenyl optionally substituted by fluoro or chloro para to the indicated group X and/or optionally substituted by fluoro, chloro or $C_1$-$C_4$-alkyl meta to the indicated group X;

R¹ is hydrogen or $C_1$-$C_4$-alkyl optionally substituted by hydroxy;

R² is hydrogen or $C_1$-$C_4$-alkyl;

R³ is a heterocyclic group having 5 to 11 ring atoms of which 1 to 4 are hetero atoms selected from nitrogen, oxygen and sulphur;

X is —O—, —CH₂— or —C(=O)—;

Y is O or S; and m is 1 or 2.

8. A compound according to claim 1, which is of formula IV

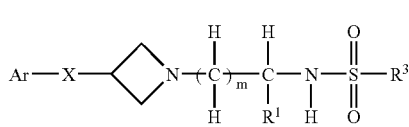

where

Ar is phenyl substituted by one or two substituents selected from fluorine and chlorine, one of said substituents being para to the indicated group X, R¹ is hydrogen or $C_1$-$C_4$-alkyl substituted by hydroxy or $C_1$-$C_4$-alkoxy, R³ is R³ is an aromatic N-or S-heterocyclic group having 5 to 10 ring atoms;

X is —O— and m is 2 or 3.

9. A compound according to claim 1, where

Ar is phenyl optionally substituted by one or more substituents selected from halogen, $C_1$-$C_8$-alkyl, cyano or nitro, R¹ is hydrogen or $C_1$-$C_8$-alkyl optionally substituted by hydroxy, $C_1$-$C_8$-alkoxy, acyloxy, halogen, carboxy, $C_1$-$C_8$-alkoxycarbonyl, —N(R⁴)R⁵, —CON(R⁶)R⁷ or by a monovalent cyclic organic group having 3 to 15 atoms in the ring system, R² is hydrogen or $C_1$-$C_8$-alkyl and R³ is $C_1$-$C_8$-alkyl substituted by phenyl, phenoxy, acyloxy or naphthyl, R³ is a heterocyclic group having 5 to 11 ring atoms of which 1 to 4 are hetero atoms selected from nitrogen, oxygen and sulphur atoms;

R⁴ and R⁵ are each independently hydrogen or $C_1$-$C_8$-alkyl, or R⁴ is hydrogen and R⁵ is hydroxy-$C_1$-$C_8$-alkyl, acyl, —SO₂R⁸ or —CON(R⁶)R⁷, or R⁴ and R⁵ together with the nitrogen atom to which they are attached denote a 5-or 6-membered heterocyclic group, R⁶ and R⁷ are each independently hydrogen or $C_1$-$C_8$-alkyl, or R⁶ and R⁷ together with the nitrogen atom to which they are attached denote a 5- or 6-membered heterocyclic group, R⁸ is $C_1$-$C_8$-alkyl, $C_1$-$C_8$-haloalkyl, or phenyl optionally substituted by $C_1$-$C_8$-alkyl, X is —C(=O)—, —O—, —CH₂—, or CH(OH), Y is oxygen or sulfur, m is 1, 2, 3 or 4, and n, p and q are each 0 or 1, n+p+q=1 or 2, n+q=1, p+q=1, and when n is 0, p is 0.

10. A compound according to claim 1, where

Ar is phenyl optionally substituted by one or more substituents selected from halogen, $C_1$-$C_8$-alkyl, cyano or nitro, R¹ is hydrogen or $C_1$-$C_8$-alkyl optionally substituted by hydroxy, $C_1$-$C_8$-alkoxy, acyloxy, halogen, carboxy, $C_1$-$C_8$-alkoxycarbonyl, —N(R⁴)R⁵, —CON(R⁶)R⁷ or by a monovalent cyclic organic group having 3 to 15 atoms in the ring system, $R^2$ is hydrogen or $C_1$-$C_8$-alkyl $R^3$ is a heterocyclic group having 5 to 11 ring atoms of which 1 to 4 are hetero atoms selected from nitrogen, oxygen and sulphur atoms;

$R^4$ and $R^5$ are each independently hydrogen or $C_1$-$C_8$-alkyl, or $R^4$ is hydrogen and $R^5$ is hydroxy-$C_1$-$C_8$-alkyl, acyl, —$SO_2R^8$ or —$CON(R^6)R^7$, or $R^4$ and $R^5$ together with the nitrogen atom to which they are attached denote a 5- or 6-membered heterocyclic group, $R^6$ and $R^7$ are each independently hydrogen or $C_1$-$C_8$-alkyl, or $R^6$ and $R^7$ together with the nitrogen atom to which they are attached denote a 5- or 6-membered heterocyclic group, $R^8$ is $C_1$-$C_8$-alkyl, $C_1$-$C_8$-haloalkyl, or phenyl optionally substituted by $C_1$-$C_8$-alkyl, X is —C(=O)—, —O—, —$CH_2$—, or CH(OH), Y is oxygen or sulfur, m is 1, 2, 3 or 4, and n, p and q are each 0 or 1, n+p+q=1 or 2, n+q=1, p+q=1, and when n is 0, p is 0.

11. A compound according to claim 1 that is also a compound of formula II

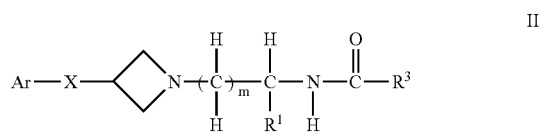

where m is 2 and Ar, X, $R^1$ and $R^3$ are as shown in the following table

| Ar | X | $R^1$ | $R^3$ |
|---|---|---|---|
|  | —O— | H | 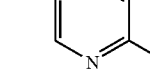 |
|  | —O— | H | 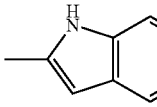 |
|  | —O— | H |  |
|  | —O— | H | 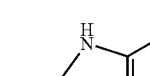 |
|  | —O— | H | 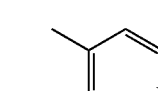 |
|  | —O— | H | 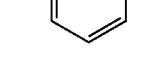 |

-continued

| Ar | X | R¹ | R³ |
|---|---|---|---|
| 4-F-phenyl | —O— | HOCH₂— | 7-methoxy-2-methylbenzofuran-4-yl |
| 4-F-phenyl | —O— | H | 7-ethoxy-2-methylbenzofuran-4-yl |

12. A compound of claim 1 that is also a compound of formula III

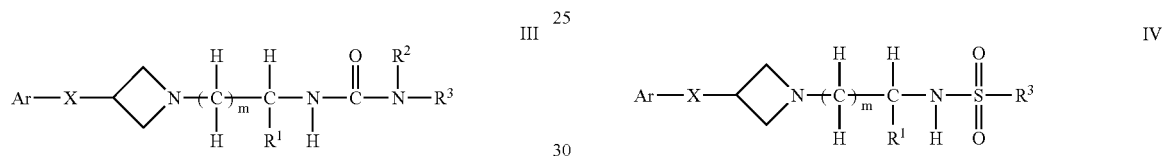

where Ar, X, m, R¹, R² and R³ are as shown in the following table

| Ar | X | m | R¹ | R² | R³ |
|---|---|---|---|---|---|
| 4-F-phenyl | —O— | 2 | H | —H | 5-methyl-2,3-dihydrobenzofuran-4-yl |

13. A compound of claim 1 that is also a compound of formula

Ar—X—azetidinyl—N—(C)ₘ—C(R¹)H—N(H)—C(O)—N(1,2,3,4-tetrahydroquinolinyl)

where Ar, X, m, and R1 are as shown in the following table

| Ar | X | m | R¹ |
|---|---|---|---|
| 4-F-phenyl | —O— | 2 | H |

14. A compound of claim 1 that is also of a compound of formula IV

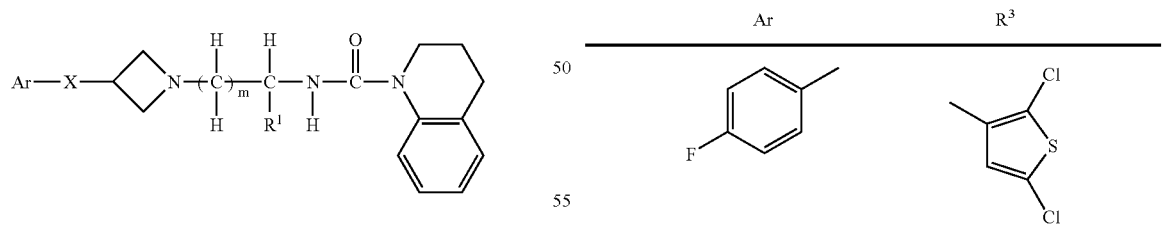

where m is 2, X is O, R¹ is hydrogen, and Ar and R³ are as shown in the following table

| Ar | R³ |
|---|---|
| 4-F-phenyl | 2,5-dichloro-4-methylthiophen-3-yl |
| 4-F-phenyl | 8-methylquinolin-5-yl |

15. A compound of claim 1 that is also a compound of formula III

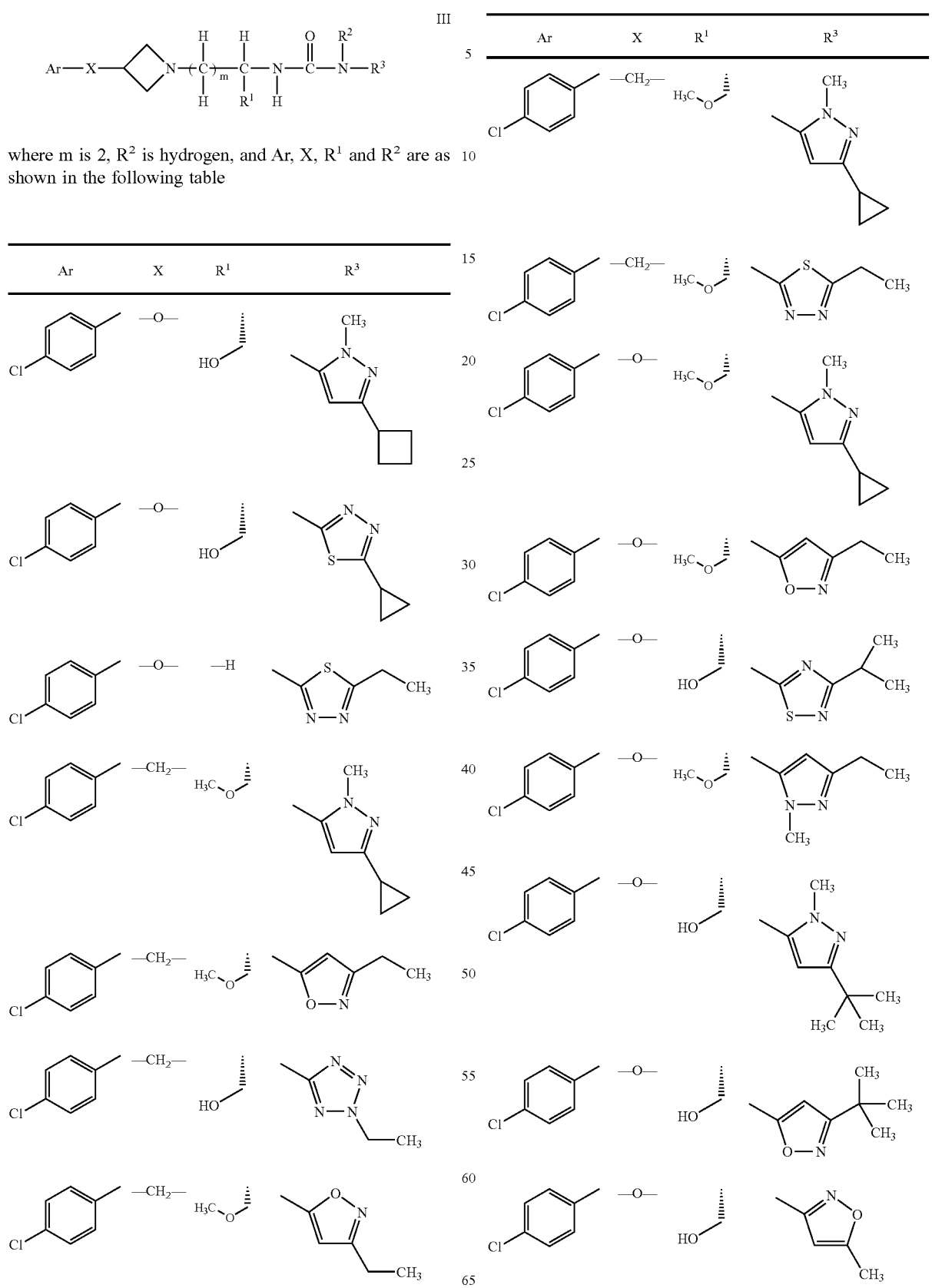

-continued

16. A compound of claim 1 that is also a compound of formula IIIa
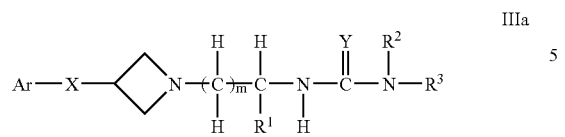
where Ar, X, m, R¹, Y, R² and R³ are as shown in the following table -continued
| Ar | X | m | R¹ | Y | R² | R³ |
|---|---|---|---|---|---|---|
| 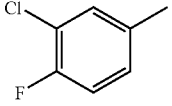 | —O— | 2 | 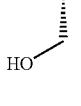 | O | H | 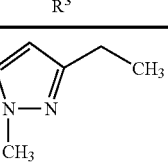 |
| 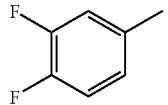 | —O— | 2 | 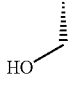 | O | H | 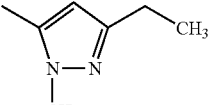 |
| 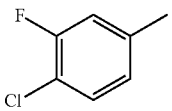 | —O— | 2 | 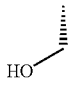 | O | H | 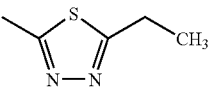 |
| 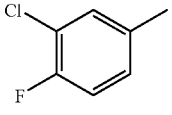 | —O— | 2 | 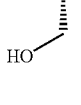 | O | H | 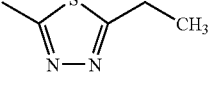 |
| 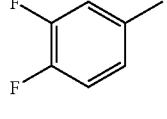 | —O— | 2 | 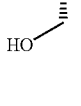 | O | H | 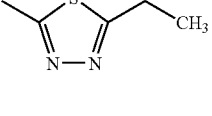 |
| 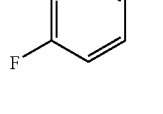 | —CH₂— | 2 | 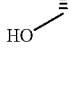 | O | H | 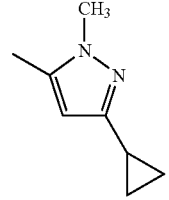 |
| 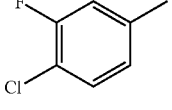 | —CH₂— | 2 | 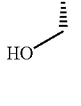 | O | H | 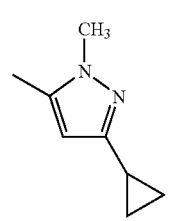 |
| 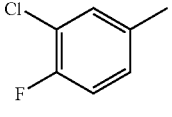 | —CH₂— | 2 | 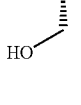 | O | H | 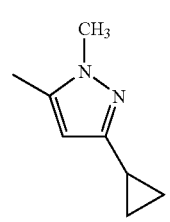 |
| 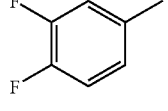 | —CH₂— | 2 | 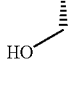 | O | H | 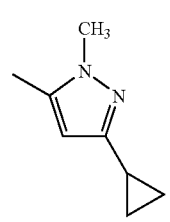 |

-continued
| Ar | X | m | R¹ | Y | R² | R³ |
|---|---|---|---|---|---|---|
| 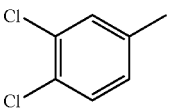 | —CH₂— | 2 |  | O | H | 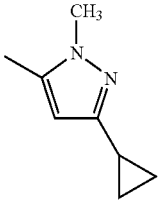 |
| 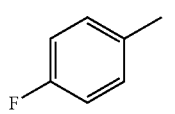 | —CH₂— | 2 |  | O | H | 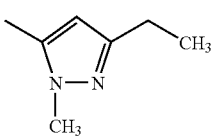 |
| 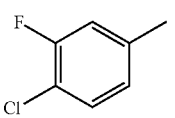 | —CH₂— | 2 |  | O | H | 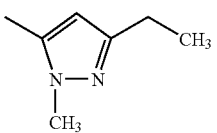 |
| 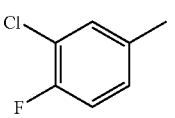 | —CH₂— | 2 |  | O | H | 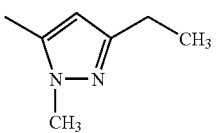 |
| 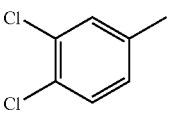 | —CH₂— | 2 |  | O | H | 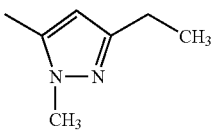 |
| 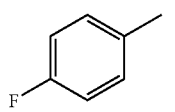 | —CH₂— | 2 |  | O | H | 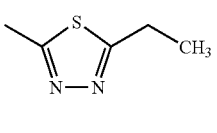 |
| 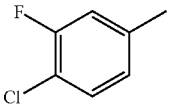 | —CH₂— | 2 |  | O | H | 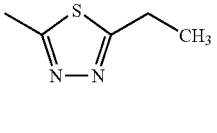 |
| 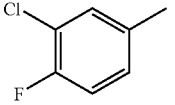 | —CH₂— | 2 |  | O | H | 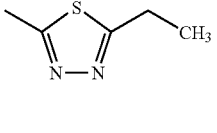 |
| 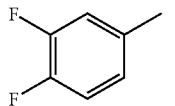 | —CH₂— | 2 |  | O | H | 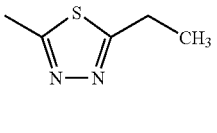 |
| 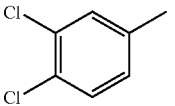 | —CH₂— | 2 |  | O | H | 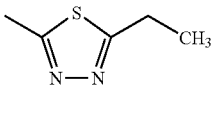 |
|  | —CH₂— | 2 |  | O | H |  |

-continued

| Ar | X | m | R¹ | Y | R² | R³ |
|---|---|---|---|---|---|---|
| 3-F,4-Cl-phenyl | —C(=O)— | 2 | HO (wedge) | O | H | 1,5-dimethyl-3-cyclopropyl-pyrazol-3-yl |
| 3-Cl,4-F-phenyl | —C(=O)— | 2 | HO (wedge) | O | H | 1,5-dimethyl-3-cyclopropyl-pyrazol-3-yl |
| 3,4-diF-phenyl | —C(=O)— | 2 | HO (wedge) | O | H | 1,5-dimethyl-3-cyclopropyl-pyrazol-3-yl |
| 3-F,4-Cl-phenyl | —C(=O)— | 2 | HO (wedge) | O | H | 1,5-dimethyl-3-ethyl-pyrazol-4-yl |
| 3-Cl,4-F-phenyl | —C(=O)— | 2 | HO (wedge) | O | H | 1,5-dimethyl-3-ethyl-pyrazol-4-yl |
| 3,4-diF-phenyl | —C(=O)— | 2 | HO (wedge) | O | H | 1,5-dimethyl-3-ethyl-pyrazol-4-yl |
| 3-F,4-Cl-phenyl | —C(=O)— | 2 | HO (wedge) | O | H | 2-methyl-5-ethyl-1,3,4-thiadiazol-yl |
| 3-Cl,4-F-phenyl | —C(=O)— | 2 | HO (wedge) | O | H | 2-methyl-5-ethyl-1,3,4-thiadiazol-yl |
| 3,4-diF-phenyl | —C(=O)— | 2 | HO (wedge) | O | H | 2-methyl-5-ethyl-1,3,4-thiadiazol-yl |
| phenyl | —O— | 2 | HO (wedge) | O | H | 2-methyl-5-ethyl-1,3,4-thiadiazol-yl |

| Ar | X | m | R¹ | Y | R² | R³ |
|---|---|---|---|---|---|---|
| 3-Cl-phenyl | —O— | 2 | ⋮ HO | O | H | 2-ethyl-1,3,4-thiadiazol-5-yl |
| 3-F-phenyl | —O— | 2 | ⋮ HO | O | H | 2-ethyl-1,3,4-thiadiazol-5-yl |
| 4-Cl-3-CH₃-phenyl | —O— | 2 | ⋮ HO | O | H | 3-cyclopropyl-1,5-dimethyl-1H-pyrazol-5-yl |
| 4-F-3-CH₃-phenyl | —O— | 2 | ⋮ HO | O | H | 3-cyclopropyl-1,5-dimethyl-1H-pyrazol-5-yl |
| 4-Cl-3-CH₃-phenyl | —CH₂— | 2 | ⋮ HO | O | H | 3-cyclopropyl-1,5-dimethyl-1H-pyrazol-5-yl |
| 4-F-3-CH₃-phenyl | —CH₂— | 2 | ⋮ HO | O | H | 3-cyclopropyl-1,5-dimethyl-1H-pyrazol-5-yl |
| 4-Cl-3-CH₃-phenyl | —C(O)— | 2 | ⋮ HO | O | H | 3-cyclopropyl-1,5-dimethyl-1H-pyrazol-5-yl |
| 4-F-3-CH₃-phenyl | —C(O)— | 2 | ⋮ HO | O | H | 3-cyclopropyl-1,5-dimethyl-1H-pyrazol-5-yl |

-continued
| Ar | X | m | R¹ | Y | R² | R³ |
|---|---|---|---|---|---|---|
| 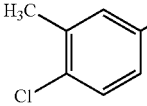 | —O— | 2 |  | O | H | 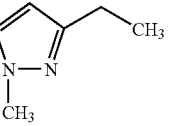 |
| 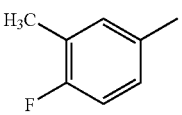 | —O— | 2 |  | O | H | 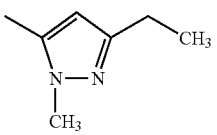 |
| 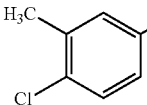 | —CH₂— | 2 |  | O | H | 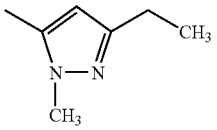 |
| 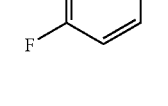 | —CH₂— | 2 |  | O | H | 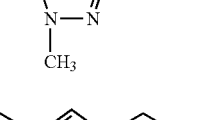 |
| 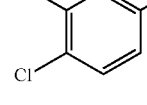 |  | 2 | 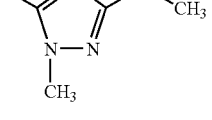 | O | H | 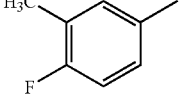 |
|  | 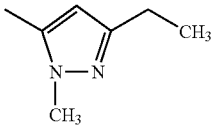 | 2 | 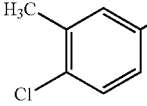 | O | H |  |
| 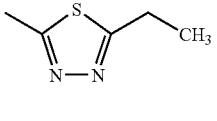 | —O— | 2 | 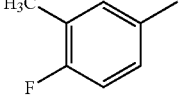 | O | H |  |
| 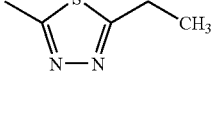 | —O— | 2 | 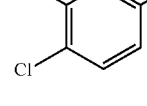 | O | H |  |
| 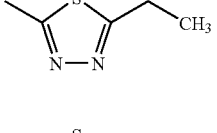 | —CH₂— | 2 | 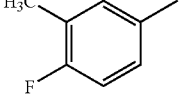 | O | H |  |
| 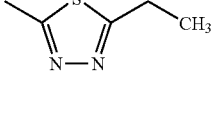 | —CH₂— | 2 | | O | H | |
| 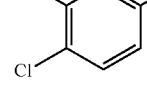 |  | 2 | | O | H | 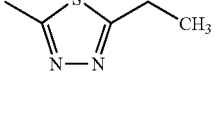 |

-continued

| Ar | X | m | R¹ | Y | R² | R³ |
|---|---|---|---|---|---|---|
| 4-F-3-methylphenyl | —C(O)— | 2 | HO⋯ (OH) | O | H | 2-methyl-5-ethyl-1,3,4-thiadiazole |
| 4-Cl-phenyl | —CH₂— | 2 | HO⋯ (OH) | O | H | 2-methyl-5-ethyl-1,3,4-thiadiazole |
| 4-Cl-phenyl | —CH₂— | 2 | —CH₃ | O | H | 2-methyl-5-ethyl-1,3,4-thiadiazole |
| 4-Cl-phenyl | —O— | 2 | HO⋯ (OH) | O | H | 3-methyl-5-ethyl-isoxazole |
| 4-Cl-phenyl | —O— | 2 | HO⋯ (OH) | O | H | 5-methyl-3-ethyl-1-isopropyl-pyrazole |
| 4-Cl-phenyl | —O— | 2 | HO⋯ (OH) | O | H | 5-methyl-3-ethyl-1-ethyl-pyrazole |
| 4-Cl-phenyl | —O— | 2 | HO⋯ (OH) | O | H | 5-methyl-3-ethyl-1-tert-butyl-pyrazole |
| 4-F-phenyl | —O— | 2 | HO⋯ (OH) | O | H | 2-methyl-5-ethyl-1,3,4-thiadiazole |
| 4-F-phenyl | —O— | 2 | HO⋯ (OH) | O | H | 1,5-dimethyl-3-cyclopropyl-pyrazole |
| 4-F-phenyl | —O— | 2 | HO⋯ (OH) | O | H | 5-methyl-3-ethyl-1-methyl-pyrazole |

-continued

| Ar | X | m | R¹ | Y | R² | R³ |
|---|---|---|---|---|---|---|
| 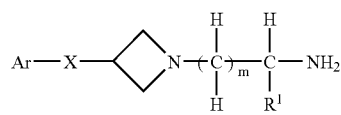 | —O— | 2 | H | O | H | (5-ethyl-1,3,4-thiadiazol-2-yl, methyl) |
| (4-chlorophenyl) | —O— | 2 | H | O | H | (5-ethyl-1,3,4-thiadiazol-2-yl, methyl) |
| (4-chlorophenyl) | —O— | 2 |  | O | H | (3-ethyl-5-methylisoxazol) |

17. A pharmaceutical composition comprising as active ingredient a compound of formula I as defined in claim 1.

18. A pharmaceutical composition comprising a compound of formula I as defined in claim 1 in combination with another drug substance which is an anti-inflammatory, a bronchodilator or an antihistamine.

19. A process for the preparation of a compound of formula I as defined in claim 1 which comprises (i) (A) for the preparation of compounds of formula I where n is 1, p is 1, q is 0 and R² is hydrogen, reacting a compound of formula V

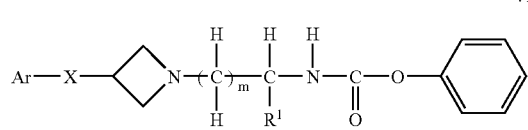

where Ar, X, m and R¹ are as defined in claim 1, with a compound of formula VI

Y=C=N—R³      VI where Y and R³ are as defined in claim 1, with the proviso that when R¹ contains a reactive functional group it may be in protected form, and, where R¹ in the product contains a protected functional group, replacing the protecting group by hydrogen;

(B) for the preparation of compounds of formula I where n is 1, p is 1, q is 0 and R² is hydrogen or $C_1$-$C_8$-alkyl, reacting a compound of formula VII

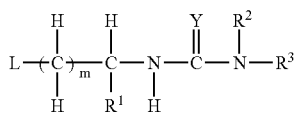

where Ar, X, m and R¹ are as defined in claim 1, with a compound of formula VIII

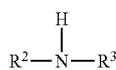

where R² and R³ are as defined in claim 1, or and, where R¹ in the product contains a protected functional group, replacing the protecting group by hydrogen;

(C) for the preparation of compounds of formula I where n is 1, p is 1, q is 0 and R² and R³ together with the nitrogen atom to which they are attached denote a heterocyclic group, reacting a compound of formula IX

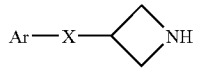

where Ar and X are as defined in claim 1, with a compound of formula X

X $$L\!-\!(CH_2)_m\!-\!CHR^1\!-\!NH\!-\!C(=Y)\!-\!NR^2R^3$$

where m, R¹ and Y are as defined in claim 1, R² and R³ together with the nitrogen atom to which they are attached denote a heterocyclic group having 5 to 10 ring atoms of which one, two or three are hetero atoms, and L is halogen;

(D) for the preparation of compounds of formula I when n is 1, p is 0, q is 0 and Y is oxygen, reacting a compound of formula IX where Ar and X are as defined in claim 1, with a compound of formula XI

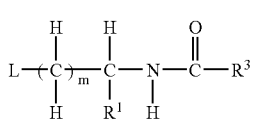
XI where L, m, $R^1$ and $R^3$ are as defined in claim 1;

(E) for the preparation of compounds of formula I where n is 1, p is 0, q is 0 and Y is oxygen, reacting a compound of formula V where Ar, X, m and $R^1$ are as defined in claim 1, with a compound of formula XII

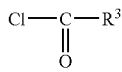
XII where $R^3$ is as defined in claim 1, and, where $R^1$ in the product contains a protected functional group, replacing the protecting group by hydrogen;

(F) for the preparation of compounds of formula I where n is 1, p is 0, q is 0, $R^2$ is hydrogen and Y is oxygen, reacting a compound of formula V where Ar, X, m and $R^1$ are as defined in claim 1, with a compound of formula XIII

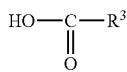
XIII where $R^3$ is as defined in claim 1, and, where $R^1$ in the product contains a protected functional group, replacing the protecting group by hydrogen;

(G) for the preparation of compounds of formula I where n is 0, p is 0, and q is 1, reacting a compound of formula IX where Ar and X are as defined in claim 1 in the form of a hydrohalide salt with a compound of formula XIV

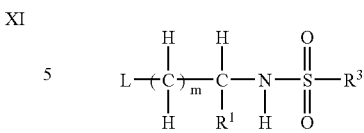
XIV where L, m, $R^1$ and $R^3$ are as defined in claim 1;

(H) for the preparation of compounds of formula I where n is 1, p is 1, q is 0 and Y is oxygen, reacting a compound of formula V where Ar, X, m and $R^1$ are as defined in claim 1, with a compound of formula XV

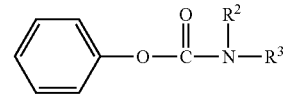
XV where $R^2$ and $R^3$ are defined in claim 1; or for the preparation on compounds of formula I where n is 1, p is 0, q is 0, Y is oxygen and $R^2$ is $C_1$-$C_8$-alkyl or $C_3$-$C_{10}$-cycloalkyl, reacting a compound of formula V where Ar, X, m and $R^1$ are as defined in claim 1, with a compound of formula XVI

XVI where $R^2$ is $C_1$-$C_8$-alkyl or $C_3$-$C_{10}$-cycloalkyl, $R^3$ is as defined in claim 1 and Z is a halogen, with the proviso that when $R^1$ contains a reactive functional group it may be in protected form, and, where $R^1$ in the product contains a protected functional group, replacing the protecting group by hydrogen; and (ii) recovering the product in free or salt form.

\* \* \* \* \*